US007812016B2

(12) United States Patent
Johns

(10) Patent No.: US 7,812,016 B2
(45) Date of Patent: Oct. 12, 2010

(54) NAPHTHYRIDINE INTEGRASE INHIBITORS

(75) Inventor: Brian A. Johns, Durham, NC (US)

(73) Assignee: SmithKline Beecham Corporation, Philadelphia, PA (US)

(*) Notice: Subject to any disclaimer, the term of this patent is extended or adjusted under 35 U.S.C. 154(b) by 1222 days.

(21) Appl. No.: 10/556,311

(22) PCT Filed: May 12, 2004

(86) PCT No.: PCT/US2004/014814

§ 371 (c)(1),
(2), (4) Date: Nov. 10, 2005

(87) PCT Pub. No.: WO2004/101512

PCT Pub. Date: Nov. 25, 2004

(65) Prior Publication Data

US 2007/0142365 A1    Jun. 21, 2007

Related U.S. Application Data

(60) Provisional application No. 60/470,059, filed on May 13, 2003.

(51) Int. Cl.
*A61K 31/541* (2006.01)
*C07D 471/04* (2006.01)
(52) U.S. Cl. ........................ 514/222.2; 544/3
(58) Field of Classification Search ............ 544/3; 514/222.2
See application file for complete search history.

(56) References Cited

U.S. PATENT DOCUMENTS 5,466,697 A   11/1995  Wilhelm et al.
7,148,237 B2  12/2006  Fuji et al.

FOREIGN PATENT DOCUMENTS

| WO | WO 02/30426  | 4/2002 |
| WO | WO 02/30930  | 4/2002 |
| WO | WO 02/30931  | 4/2002 |
| WO | WO 02/36734  | 5/2002 |
| WO | WO 02/055079 | 7/2002 |
| WO | WO 02/070486 | 9/2002 |

OTHER PUBLICATIONS

Montgomery et al., "1-B-D-Arabinofuranosyl, etc.," J. Med. Chem., 1982, 25, 96-98.*
Siddiqui et al., "3-Deaza- and, etc.," J. Med. Chem., 1995, 38, 1035-1038.*
Paeshuyse et al., "A Novel, Highly Selective, etc.," J of Virology, Jan. 2006, 80(1), 149-160.*

* cited by examiner

*Primary Examiner*—Patricia L Morris
(74) *Attorney, Agent, or Firm*—Karen L. Prus

(57) ABSTRACT

The present invention features compounds that are HIV integrase inhibitors and therefore are useful in the inhibition of HIV replication, the prevention and/or treatment of infection by HIV, and in the treatment of AIDS and/or ARC.

10 Claims, No Drawings

NAPHTHYRIDINE INTEGRASE INHIBITORS

This application is filed pursuant to 35 U.S.C. §371 as a United States National Phase Application of International Application No. PCT/US2004/014814 filed May 12, 2004 which claims priority from U.S. 60/470,059 filed May 13, 2003

BACKGROUND OF THE INVENTION

The human immunodeficiency virus ("HIV") is the causative agent for acquired immunodeficiency syndrome ("AIDS"), a disease characterized by the destruction of the immune system, particularly of CD4$^+$ T-cells, with attendant susceptibility to opportunistic infections, and its precursor AIDS-related complex ("ARC"), a syndrome characterized by symptoms such as persistent generalized lymphadenopathy, fever and weight loss. HIV is a retrovirus; the conversion of its RNA to DNA is accomplished through the action of the enzyme reverse transcriptase. Compounds that inhibit the function of reverse transcriptase inhibit replication of HIV in infected cells. Such compounds are useful in the prevention or treatment of HIV infection in humans.

A required step in HIV replication in human T-cells is the insertion by virally-encoded integrase of proviral DNA into the host cell genome. Integration is believed to be mediated by integrase in a process involving assembly of a stable nucleoprotein complex with viral DNA sequences, cleavage of two nucleotides from the 3' termini of the linear proviral DNA and covalent joining of the recessed 3' OH termini of the proviral DNA at a staggered cut made at the host target site. The repair synthesis of the resultant gap may be accomplished by cellular enzymes.

There is continued need to find new therapeutic agents to treat human diseases. HIV integrase is an attractive target for the discovery of new therapeutics due to its important role in viral infections, particularly HIV infections. Integrase inhibitors are disclosed in WO02/70486. The compounds of the present invention exhibit advantages over previously disclosed integrase inhibitors, for example increased potency, metabolic stability, increased therapeutic index, or other pharmaceutical properties.

SUMMARY OF THE INVENTION

The present invention features compounds that are HIV integrase inhibitors and therefore are useful in the inhibition of HIV replication, the prevention and/or treatment of infection by HIV, and in the treatment of AIDS and/or ARC. Accordingly, the present invention features compounds of formula (I):

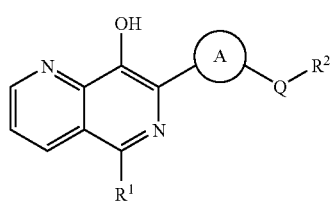

(I)

wherein:
$R^1$ is hydrogen, halogen, $C_{1-8}$alkyl, $C_{3-6}$cycloalkyl, $C_{1-8}$haloalkyl, $C_{6-14}$aralkyl, $C_{2-6}$alkenyl, $C_{3-6}$cycloalkenyl, $C_{3-6}$alkynyl, $C_{1-8}$alkoxy, —CN, —R$^3$OR$^4$, —R$^3$C(O)R$^4$, —C(O)R$^4$, —R$^3$C(O)OR$^4$, —R$^3$COR$^4$, —C(O)OR$^4$, —R$^3$SR$^4$, —SR$^4$, —N(R$^4$)$_2$, —R$^3$N(R$^4$)$_2$, —R$^3$C(O)N(R$^4$)$_2$, —NC(O)N(R$^4$)$_2$, —C(O)N(R$^4$)$_2$, —R$^3$N(R$^4$)C(R$^4$)(O), —N(R$^4$)C(O)R$^4$, —N(R$^4$)C(O)OR$^4$, —N(R$^4$)C(O)C(O)N(R$^4$)$_2$, —N(R$^4$)C(R$^4$)(O), —N(R$^4$)C(R$^4$)(O), —R$^3$S(O)$_2$R$^4$, —NS(O)$_2$NR$^4$, —S(O)$_2$R$^4$, —S(O)$_2$N(R$^4$)$_2$, —R$^3$N(R$^4$)S(O)$_2$R$^4$, —N(R$^4$)S(O)$_2$R$^4$, —R$^3$S(O)$_2$NR$^4$, —N(R$^4$)R$^3$SR$^4$, —N(R$^4$)R$^3$OR$^4$, —N(R$^4$)R$^3$N(R$^4$)$_2$, —N(R$^4$)R$^3$N(R$^4$)C(R$^4$)(O), $C_{6-14}$aryl wherein said $C_{6-14}$aryl is optionally substituted with one or more substituents independently selected from the group consisting of halogen, hydroxy, $C_{1-8}$alkyl, $C_{1-8}$haloalkyl, —OR$^3$, —SR$^3$, —CN, hydroxy, —R$^3$C(O)N(R$^4$)$_2$, —C(O)N(R$^4$)$_2$, —R$^3$C(O)R$^4$, —R$^3$OR$^3$OH, —C(O)R$^4$, —N(R$^4$)C(O)R$^4$, —N(R$^4$)C(O)R$^4$, —N(R$^4$)C(O)OR$^4$, —S(O)$_2$N(R$^4$)$_2$, —S(O)$_2$R$^4$, —R$^3$N(R$^4$)C(O)OR$^4$, —R$^3$N(R$^4$)C(O)R$^4$, —N(R$^4$)$_2$, —R$^3$N(R$^4$)$_2$, $C^{6-14}$aryl, $C^{6-14}$aryloxy, heterocycle, and R$^3$ optionally substituted with $C_{6-14}$aryl, heterocycle wherein said heterocycle is optionally substituted with one or more substituents independently selected from the group consisting of halogen, hydroxy, $C_{1-8}$alkyl, $C_{1-8}$haloalkyl, —OR$^3$, —SR$^3$, —CN, hydroxy, oxo, —R$^3$C(O)N(R$^4$)$_2$, —C(O)N(R$^4$)$_2$, —R$^3$C(O)R$^4$, —R$^3$OR$^3$OH, —C(O)R$^4$, —N(R$^4$)C(O)R$^4$, —C(O)R$^3$N(R$^4$)$_2$, —N(R$^4$)C(O)R$^4$, —R$^3$N(R$^4$)C(O)R$^4$, —N(R$^4$)$_2$, —R$^3$N(R$^4$)$_2$, $C_{6-14}$aryl, $C_{6-14}$aryloxy, heterocycle, and R$^3$ optionally substituted with $C_{6-14}$aryl, Y wherein said Y is optionally substituted with one or more substituents independently selected from the group consisting of —OR$^5$, —NR$^5$R$^6$, —N(R$^5$)YNR$^6$, —C(O)$_m$R$^5$, —C(O)NR$^5$R$^6$, —N(R$^5$)C(O)$_m$R$^5$, —N(R$^5$)Y$_p$C(O)NR$^5$R$^6$, —N(R$^5$)Y$_p$C(O)$_m$heterocycle, —O(Y)C(O)NR$^5$R$^6$, —S(O)$_n$Y$_p$C(O)NR$^5$R$^6$, —S(O)$_n$R$^5$R$^6$, —S(O)$_n$NR$^5$, —S(O)$_n$heterocycle, —N(R$^5$)Y$_p$S(O)$_n$NR$^5$R$^6$, —C(O)$_m$heterocycle, —S(O)$_n$heterocycle, —C(O)C(O)NR$^5$R$^6$, —N(R$^5$)C(O)C(O)NR$^5$R$^6$, —N(R$^5$)Y$_p$C(O)C(O)NR$^5$R$^6$, —C(O)C(O)$_m$heterocycle, —C(O)NR$^5$Y$_p$C(O)NR$^5$R$^6$, -heterocycle, —OY$_p$NR$^5$R$^6$, —O(Y)$_p$C(O)NR$^5$R$^6$, —O(Y)$_p$N(R$^5$)C(O)$_m$R$^5$, —O(Y)$_p$C(O)$_m$R$^5$, —C$_{6-14}$aryl, —N(C=NR$^5$)NR$^5$R$^6$, —C(R$^5$)(C=NR$^5$)NR$^5$R$^6$, and-(C=NR$^5$)NR$^5$R$^6$;

$R^2$ is $C_{3-6}$cycloalkyl, $C_{6-14}$aryl optionally substituted with one or more substituents independently selected from the group consisting of hydrogen, halogen, hydroxy, $C_{1-8}$alkyl, —OR$^5$, and NR$^5$R$^6$, or heterocycle optionally substituted with one or more substituents selected from the group consisting of hydrogen, halogen, $C_{1-8}$alkyl, —OR$^5$, and NR$^5$R$^6$;

$R^3$ is $C_{1-8}$alkyl, $C_{3-6}$cycloalkyl, haloC$_{1-8}$alkyl, $C_{2-6}$alkenyl, $C_{3-6}$cycloalkenyl, or $C_{3-6}$alkenyl, or heterocycle;

$R^4$ is hydrogen, $C_{1-8}$alkyl, $C_{3-6}$cycloalkyl, $C_{1-8}$haloalkyl, $C_{6-14}$aryl, $C_{6-14}$aralkyl, $C_{2-6}$alkenyl, or $C_{3-6}$cycloalkenyl, $C_{3-6}$alkynyl, or heterocycle;

$R^5$ and $R^6$ are independently selected from the group consisting of hydrogen, $C_{1-8}$haloalkyl, $C_{1-8}$alkylC$_{3-6}$cycloalkyl, $C_{6-14}$aryl, $C_{6-14}$aralkyl, —C(O)$_m$R$^7$, —C(O)C(O)$_m$R$^7$, —C(O)$_m$heterocycle, —C(O)C(O)$_m$heterocycle, —S(O)$_n$heterocycle, -heterocycle, and Y optionally substituted with one or more —OR$^7$, —C(O)$_m$R$^7$, —S(O)$_n$R$^7$, —S(O)$_n$R$^7$, —C(O)$_m$heterocycle, —S(O)$_n$heterocycle, —C(O)C(O)$_m$R$^7$, —C(O)C(O)$_m$heterocycle, -heterocycle, —Oheterocycle;

$R^7$ is hydrogen, $C_{1-8}$alkyl, $C_{3-6}$cycloalkyl, —Ycycloalkyl, —YOH, —Y(OY)$_w$ where w is 1-10;

m is 1 or 2;
n is 0, 1, or 2;
p is 0, or 1;

A is heterocycle;

Q is $C_{1-3}$alkyl, —$NR^4$, —O—, —C(O), —C(O$R^4$)—, $S(O)_2$, or —$CF_2$;

Y is a $C_{1-5}$ alkylene chain, wherein said $C_{1-5}$ alkylene chain is optionally substituted by one or more groups independently selected from =O, =S, and halo, and wherein said $C_{1-5}$ alkylene chain optionally contains 1-3 heteroatoms selected from oxygen, sulfur, and nitrogen;

or a pharmaceutically acceptable derivative thereof.

DETAILED DESCRIPTION OF THE INVENTION

The present invention includes the compounds of Formula (I) above, useful in treating or preventing viral infections, particularly HIV infections, pharmaceutical compositions comprising compounds of Formula (I), and processes for preparing the compounds.

The present invention also features a compound of Formula (I) wherein $R^1$ is hydrogen, halogen, $C_{1-8}$alkyl, $C_{3-6}$cycloalkyl, $C_{1-8}$haloalkyl, $C_{6-14}$aralkyl, $C_{2-6}$alkenyl, $C_{3-6}$cycloalkenyl, $C_{3-6}$alkynyl, $C_{1-8}$alkoxy, —CN, —$R^3OR^4$, —$R^3C(O)R^4$, —$C(O)R^4$, —$R^3C(O)OR^4$, —$R^3COR^4$, —$C(O)OR^4$, —$R^3SR^4$, —$SR^4$, —$N(R^4)_2$, —$R^3N(R^4)_2$, —$R^3C(O)N(R^4)_2$, —$NC(O)N(R^4)_2$, —$C(O)N(R^4)_2$, —$R^3N(R^4)C(R^4)(O)$, —$N(R^4)C(O)R^4$, —$N(R^4)C(O)OR^4$, —$N(R^4)C(O)C(O)N(R^4)_2$, —$N(R^4)C(R^4)(O)$, —$N(R^4)C(R^4)(O)$, —$R^3S(O)_2R^4$, —$NS(O)_2NR^4$, —$S(O)_2R^4$, —$S(O)_2N(R^4)_2$, —$R^3N(R^4)S(O)_2R^4$, —$N(R^4)S(O)_2R^4$, —$R^3S(O)_2NR^4$, —$N(R^4)R^3SR^4$, —$N(R^4)R^3OR^4$, —$N(R^4)R^3N(R^4)_2$, —$N(R^4)R^3N(R^4)C(R^4)(O)$, $C_{6-14}$aryl wherein said $C_{6-14}$aryl is optionally substituted with one or more substituents independently selected from the group consisting of halogen, hydroxy, $C_{1-8}$alkyl, $C_{1-8}$haloalkyl, —$OR^3$, —$SR^3$, —CN, hydroxy, —$R^3C(O)N(R^4)_2$, —$C(O)N(R^4)_2$, —$R^3C(O)R^4$, —$R^3OR^3OH$, —$C(O)R^4$, —$N(R^4)C(O)R^4$, —$N(R^4)C(O)R^4$, —$N(R^4)C(O)OR^4$, —$S(O)_2N(R^4)_2$, —$S(O)_2R^4$, —$R^3N(R^4)C(O)OR^4$, —$R^3N(R^4)C(O)R^4$, —$N(R^4)_2$, —$R^3N(R^4)_2$, $C_{6-14}$aryl, $C_{6-14}$aryloxy, heterocycle, and $R^3$ optionally substituted with $C_{6-14}$aryl, heterocycle wherein said heterocycle is optionally substituted with one or more substituents independently selected from the group consisting of halogen, hydroxy, $C_{1-8}$alkyl, $C_{1-8}$haloalkyl, —$OR^3$, —$SR^3$, —CN, hydroxy, oxo, —$R^3C(O)N(R^4)_2$, —$C(O)N(R^4)_2$, —$R^3C(O)R^4$, —$R^3OR^3OH$, —$C(O)R^4$, —$N(R^4)C(O)R^4$, —$C(O)R^3N(R^4)_2$, —$N(R^4)C(O)R^4$, —$R^3N(R^4)C(O)R^4$, —$N(R^4)_2$, —$R^3N(R^4)_2$, $C_{6-14}$aryl, $C_{6-14}$aryloxy, heterocycle, and $R^3$ optionally substituted with $C_{6-14}$aryl, Y wherein said Y is optionally substituted with one or more substituents independently selected from the group consisting of —$OR^5$, —$NR^5R^6$, —$N(R^5)YNR^6$, —$C(O)_mR^5$, —$C(O)NR^5R^6$, —$N(R^5)C(O)_mR^5$, —$N(R^5)Y_pC(O)NR^5R^6$, —$N(R^5)Y_pC(O)_m$heterocycle, —$O(Y)C(O)NR^5R^6$, —$S(O)_nY_pC(O)NR^5R^6$, —$S(O)_nR^5R^6$, —$S(O)_nNR^5$, —$S(O)_n$heterocycle, —$N(R^5)Y_pS(O)_nNR^5R^6$, —$C(O)_m$heterocycle, —$S(O)_n$heterocycle, —$C(O)C(O)NR^5R^6$, —$N(R^5)C(O)C(O)NR^5R^6$, —$N(R^5)Y_pC(O)C(O)NR^5R^6$, —$C(O)C(O)_m$heterocycle, —$C(O)NR^5Y_pC(O)NR^5R^6$, -heterocycle, —$OY_pNR^5R^6$, —$O(Y)_pC(O)NR^5R^6$, —$O(Y)_pN(R^5)C(O)_mR^5$, —$O(Y)_pC(O)_mR^5$, —$C_{6-14}$aryl, —$N(C=NR^5)NR^5R^6$, —$C(R^5)(C=NR^5)NR^5R^6$, and -$(C=NR^5)NR^5R^6$, and all other substituents are as described above, or a pharmaceutically acceptable derivative thereof.

The present invention features a compound of Formula (I) wherein $R^1$ is $C_{6-14}$aryl optionally substituted with one or more substituents independently selected from the group consisting of halogen, hydroxy, $C_{1-8}$alkyl, $C_{1-8}$haloalkyl, —$OR^3$, —$SR^3$, —CN, hydroxy, —$R^3C(O)N(R^4)_2$, —$C(O)N(R^4)_2$, —$R^3C(O)R^4$, —$R^3OR^3OH$, —$C(O)R^4$, —$N(R^4)C(O)R^4$, —$N(R^4)C(O)R^4$; and all other substituents are as defined above, or a pharmaceutically acceptable derivative thereof.

The present invention features a compound of Formula (I) wherein $R^1$ is —$N(R^4)_2$, —$NC(O)N(R^4)_2$, —$N(R^4)C(O)R^4$, —$N(R^4)C(O)OR^4$, —$N(R^4)C(O)C(O)N(R^4)_2$, —$N(R^4)C(R^4)(O)$, —$N(R^4)C(R^4)(O-NS(O)_2NR^4$, —$N(R^4)S(O)_2R^4$, —$N(R^4)R^3SR^4$, —$N(R^4)R^3OR^4$, —$N(R^4)R^3N(R^4)_2$, —$N(R^4)R^3N(R^4)C(R^4)(O)$; and all other substituents are as defined above, or a pharmaceutically acceptable derivative thereof. The present invention features a compound of Formula (I) wherein $R^1$ is —$C(O)R^4$, —$C(O)OR^4$, —$C(O)N(R^4)_2$; and all other substituents are as defined above, or a pharmaceutically acceptable derivative thereof.

The present invention features a compound of Formula (I) wherein $R^1$ is Y optionally substituted with one or more substituents independently selected from the group consisting of —$OR^5$, —$NR^5R^6$, —$N(R^5)YNR^6$, —$C(O)_mR^5$, —$C(O)NR^5R^6$, —$N(R^5)C(O)_mR^5$, —$N(R^5)Y_pC(O)NR^5R^6$, —$N(R^5)Y_pC(O)_m$heterocycle, —$O(Y)C(O)NR^5R^6$, —$S(O)_nY_pC(O)NR^5R^6$, —$S(O)_nR^5R^6$, —$S(O)_nNR^5$, —$S(O)_n$heterocycle, —$N(R^5)Y_pS(O)_nNR^5R^6$, —$C(O)_m$heterocycle, —$S(O)_n$heterocycle, —$C(O)C(O)NR^5R^6$, —$N(R^5)C(O)C(O)NR^5R^6$, —$N(R^5)Y_pC(O)C(O)NR^5R^6$, —$C(O)C(O)_m$heterocycle, —$C(O)NR^5Y_pC(O)NR^5R^6$, -heterocycle, —$OY_pNR^5R^6$, —$O(Y)_pC(O)NR^5R^6$, —$O(Y)_pN(R^5)C(O)_mR^5$, —$O(Y)_pC(O)_mR^5$, —$C_{6-14}$aryl, —$N(C=NR^5)NR^5R^6$, —$C(R^5)(C=NR^5)NR^5R^6$, and-$(C=NR^5)NR^5R^6$; and all other substituents are as defined above or a pharmaceutically acceptable derivative thereof.

The present invention features a compound of Formula (I) wherein $R^1$ is $C_{6-14}$aryl optionally substituted with one or more substituents independently selected from the group consisting of halogen, hydroxy, $C_{1-8}$alkyl, $C_{1-8}$haloalkyl, —$OR^3$, —$SR^3$, —CN, hydroxy, —$R^3C(O)N(R^4)_2$, —$C(O)N(R^4)_2$, —$R^3C(O)R^4$, —$R^3OR^3OH$, —$C(O)R^4$, —$N(R^4)C(O)R^4$, —$N(R^4)C(O)R^4$; A is oxadiazolyl, triazolyl, thiadazolyl, oxazolyl, $R^2$ is $C_{6-14}$aryl optionally substituted with one or more substituents selected from the group consisting of hydrogen, halogen, hydroxy, $C_{1-8}$alkyl, —$OR^5$, and $NR^5R^6$; Q is $C_{1-3}$alkyl; or a pharmaceutically acceptable derivative thereof.

The present invention features a compound of Formula (I) wherein $R^1$ is —$N(R^4)_2$, —$NC(O)N(R^4)_2$, —$N(R^4)C(O)R^4$, —$N(R^4)C(O)OR^4$, —$N(R^4)C(O)C(O)N(R^4)_2$, —$N(R^4)C(R^4)(O)$, —$N(R^4)C(R^4)(O-NS(O)_2NR^4$, —$N(R^4)S(O)_2R^4$, —$N(R^4)R^3SR^4$, —$N(R^4)R^3OR^4$, —$N(R^4)R^3N(R^4)_2$, —$N(R^4)R^3N(R^4)C(R^4)(O)$, A is oxadiazolyl, triazolyl, thiadazolyl, oxazolyl; $R^2$ is $C_{6-14}$aryl optionally substituted with one or more substituents selected from the group consisting of hydrogen, halogen, hydroxy, $C_{1-8}$alkyl, —$OR^5$, and $NR^5R^6$; Q is $C_{1-3}$alkyl; or a pharmaceutically acceptable derivative thereof.

The present invention features a compound of Formula (I) wherein $R^1$ is —$C(O)R^4$, —$C(O)OR^4$, —$C(O)N(R^4)_2$; A is oxadiazolyl, triazolyl, thiadazolyl, oxazolyl; $R^2$ is $C_{6-14}$aryl optionally substituted with one or more substituents selected from the group consisting of hydrogen, halogen, hydroxy, $C_{1-8}$alkyl, —$OR^5$, and $NR^5R^6$; Q is $C_{1-3}$alkyl; or pharmaceutically acceptable derivative thereof.

The present invention features a compound of Formula (I) wherein $R^1$ is Y optionally substituted with one or more substituents independently selected from the group consisting of —$OR^5$, —$NR^5R^6$, —$N(R^5)YNR^6$, —$C(O)_mR^5$, —$C(O)NR^5R^6$, —$N(R^5)C(O)_mR^5$, —$N(R^5)Y_pC(O)NR^5R^6$, —$N(R^5)Y_pC(O)_m$heterocycle, —$O(Y)C(O)NR^5R^6$, —$S(O)_nY_pC(O)NR^5R^6$, —$S(O)_nR^5R^6$, —$S(O)_nNR^5$, —S(O)$_n$heterocycle, —N(R$^5$)Y$_p$S(O)$_n$NR$^5$R$^6$, —C(O)$_m$heterocycle, —S(O)$_n$heterocycle, —C(O)C(O)NR$^5$R$^6$, —N(R$^5$)C(O)C(O)NR$^5$R$^6$, —N(R$^5$)Y$_p$C(O)C(O)NR$^5$R$^6$, —C(O)C(O)$_m$heterocycle, —C(O)NR$^5$Y$_p$C(O)NR$^5$R$^6$, -heterocycle, —OY$_p$NR$^5$R$^6$, —O(Y)$_p$C(O)NR$^5$R$^6$, —O(Y)$_p$N(R$^5$)C(O)$_m$R$^5$, —O(Y)$_p$C(O)$_m$R$^5$, —C$_{6-14}$aryl, —N(C═NR$^5$)NR$^5$R$^6$, —C(R$^5$)(C═NR$^5$)NR$^5$R$^6$, and —(C═NR$^5$)NR$^5$R$^6$; A is oxadiazolyl, triazolyl, thiadiazolyl, oxazolyl; R$^2$ is C$_{6-14}$aryl optionally substituted with one or more substituents selected from the group consisting of hydrogen, halogen, hydroxy, C$_{1-8}$alkyl, —OR$^5$, and NR$^5$R$^6$; Q is C$_{1-3}$alkyl; or pharmaceutically acceptable derivative thereof.

The present invention also features a compound of formula (I) wherein R$^1$ is selected from heterocycle optionally substituted with one or more substituents independently selected from group consisting of halogen, hydroxy, C$_{1-8}$alkyl, C$_{1-8}$haloalkyl, —OR$^3$, —SR$^3$, —CN, hydroxy, oxo, —R$^3$C(O)N(R$^4$)$_2$, —C(O)N(R$^4$)$_2$, —R$^3$C(O)R$^4$, —R$^3$OR$^3$OH, —C(O)R$^4$, —N(R$^4$)C(O)R$^4$, —N(R$^4$)C(O)R$^4$, —R$^3$N(R$^4$)C(O)R$^4$, —N(R$^4$)$_2$, —R$^3$N(R$^4$)$_2$, C$_{6-14}$aryl, C$_{6-14}$aryloxy, heterocycle, and R$^3$ optionally substituted with C$_{6-14}$aryl; A is oxadiazolyl, triazolyl, thiadiazolyl, oxazolyl; R$^2$ is C$_{6-14}$aryl optionally substituted with one or more substituents selected from the group consisting of hydrogen, halogen, hydroxy, C$_{1-8}$alkyl, —OR$^5$, and NR$^5$R$^6$; Q is C$_{1-3}$alkyl; or pharmaceutically acceptable derivative thereof.

The term "alkyl", alone or in combination with any other term, refers to a straight-chain or branched-chain saturated aliphatic hydrocarbon radical containing the specified number of carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "cycloalkyl" refers to a saturated or partially saturated carbocyclic ring composed of 3-6 carbons in any chemically stable configuration. Examples of suitable carbocyclic groups include cyclopropyl cyclobutyl, cyclopentyl, cyclohexyl, and cyclohexenyl.

The term "alkenyl," alone or in combination with any other term, refers to a straight-chain or branched-chain alkyl group with at least one carbon-carbon double bond. Examples of alkenyl radicals include, but are not limited to, ethenyl, propenyl, isopropenyl, butenyl, isobutenyl, pentenyl, hexenyl, hexadienyl and the like.

The term "alkynyl" refers to hydrocarbon groups of either a straight or branched configuration with one or more carbon-carbon triple bonds which may occur in any stable point along the chain, such as ethynyl, propynyl, butynyl, pentynyl, and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "alkylene chain" refers to a straight or branched hydrocarbon chain that may be fully saturated or have one or more units of unsaturation. The unsaturation may occur in any stable point along the chain. The double bond(s) in the unsaturated alkylene chain may be in either the cis or trans configuration.

The term "halogen" refers fluorine (F), chlorine (Cl), bromine (Br), or iodine (I).

The term "aryl" alone or in combination with any other term, refers to a carbocyclic aromatic moiety (such as phenyl or naphthyl) containing the specified number of carbon atoms, preferably from 6-14 carbon atoms, and more preferably from 6-10 carbon atoms. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. The term "aralkyl" refers to an alkyl group substituted by an aryl. Examples of aralkyl groups include, but are not limited to, benzyl and phenethyl.

The term "heterocycle," "heterocyclic," and "heterocyclyl" as used herein, refer to a 3- to 7-membered monocyclic heterocyclic ring or 8-to 11-membered bicyclic heterocyclic ring system any ring of which is either saturated, partially saturated or unsaturated, and which may be optionally benzo-fused if monocyclic. Each heterocycle consists of one or more carbon atoms and from one to four heteroatoms selected from the group consisting of N, O and S, and wherein the nitrogen and sulfur heteroatoms may optionally be oxidized, and the nitrogen atom may optionally be quaternized, and including any bicyclic group in which any of the above-defined heterocyclic rings is fused to a benzene ring. The heterocyclic ring may be attached at any carbon or heteroatom, provided that the attachment results in the creation of a stable structure. Preferred heterocycles include 5-7 membered monocyclic heterocycles and 8-10 membered bicyclic heterocycles. When the heterocyclic ring has substituents, it is understood that the substituents may be attached to any atom in the ring, whether a heteroatom or a carbon atom, provided that a stable chemical structure results. "Heteroaromatics" or "heteroaryl" are included within the heterocycles as defined above and generally refers to a heterocycle in which the ring system is an aromatic monocyclic or polycyclic ring radical containing five to twenty carbon atoms, preferably five to ten carbon atoms, in which one or more ring carbons, preferably one to four, are each replaced by a heteroatom such as N, O, S and P. Preferred heteroaryl groups include 5-6 membered monocyclic heteroaryls and 8-10 membered bicyclic heteroaryls. Also included within the scope of the term "heterocycle, "heterocyclic" or "heterocyclyl" is a group in which a non-aromatic heteroatom-containing ring is fused to one or more aromatic rings, such as in an indolinyl, chromanyl, phenanthridinyl or tetrahydro-quinolinyl, where the radical or point of attachment is on the non-aromatic heteroatom-containing ring. Unless otherwise indicated, the term "heterocycle, "heterocyclic" or "heterocyclyl" also included each possible positional isomer of a heterocyclic radical, such as in 1-indolinyl, 2-indolinyl, 3-indolinyl. Examples of heterocycles include imidazolyl, imidazolinoyl, imidazolidinyl, quinolyl, isoquinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, carbolinyl, tetrazolyl, thiazolidinyl, benzofluranoyl, thiamorpholinyl sulfone, oxazolyl, oxadiazolyl, benzoxazolyl, oxopiperidinyl, oxopyrrolidinyl, oxoazepinyl, azepinyl, isoxozolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetrahydrofurodihydrofuranyl, tetrahydropyranodihydrofuranyl, dihydropyranyl, tetradyrofurofuranyl and tetrahydropyranofuranyl.

The term "heteroatom" means nitrogen, oxygen, or sulfur and includes any oxidized form of nitrogen, such as N(O) {$N^+$—$O^-$} and sulfur such as S(O) and S(O)$_2$, and the quaternized form of any basic nitrogen.

A combination of substituents or variables is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all stereochemical forms of the structure, i.e., the R and S configurations for each asymmetric center. Therefore, racemates and racemic mixtures, single enantiomers, diastereomeric mixtures and individual diastereoisomers of the present compounds are expressly included within the scope of the invention. Although the specific compounds exemplified herein may be depicted in a particular stereochemical configuration, compounds having either the opposite stereochemistry at any given chiral center or mixtures thereof are also envisioned.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C— or $^{14}$C-enriched carbon are also within the scope of this invention.

It will be apparent to one skilled in the art that certain compounds of this invention may exist in alternative tautomeric forms. All such tautomeric forms of the present compounds are within the scope of the invention. Unless otherwise indicated, the representation of either tautomer is meant to include the other.

The term "pharmaceutically effective amount" refers to an amount effective in treating a virus infection, for example an HIV infection, in a patient either as monotherapy or in combination with other agents. The term "treating" as used herein refers to the alleviation of symptoms of a particular disorder in a patient, or the improvement of an ascertainable measurement associated with a particular disorder, and may include the suppression of symptom recurrence in an asymptomatic patient such as a patient in whom a viral infection has become latent. The term "prophylactically effective amount" refers to an amount effective in preventing a virus infection, for example an HIV infection, or preventing the occurrence of symptoms of such an infection, in a patient. As used herein, the term "patient" refers to a mammal, including a human.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the antiviral agent.

The term "treatment" as used herein refers to the alleviation of symptoms of a particular disorder in a patient, or the improvement of an ascertainable measurement associated with a particular disorder, and may include the suppression of symptom recurrence in an asymptomatic patient such as a patient in whom a viral infection has become latent. The term "prophylaxis" refers to preventing a disease or condition or preventing the occurrence of symptoms of such a disease or condition, in a patient. As used herein, the term "patient" refers to a mammal, including a human.

As used herein, the term "subject" refers to a patient, animal or a biological sample. The term "biological sample", as used herein, includes, without limitation, cell cultures or extracts thereof; preparations of an enzyme suitable for in vitro assay; biopsied material obtained from a mammal or extracts thereof; and blood, saliva, urine, feces, semen, tears, or other body fluids or extracts thereof.

Throughout this specification, the word "comprise" or variations such as "comprises" or "comprising" will be understood to imply the inclusion of a stated integer or groups of integers but not the exclusion of any other integer or group of integers.

As used herein, the compounds according to the invention are defined to include pharmaceutically acceptable derivatives thereof. A "pharmaceutically acceptable derivative" means any pharmaceutically acceptable salt, ester, salt of an ester, ether, or other derivative of a compound of this invention which, upon administration to a recipient, is capable of providing directly or indirectly a compound of this invention or an inhibitorily active metabolite or residue thereof. Particularly favored derivatives and prodrugs are those that increase the bioavailability of the compounds of this invention when such compounds are administered to a mammal, for example, by allowing an orally administered compound to be more readily absorbed into the blood, or which enhance delivery of the parent compound to a biological compartment, for example, the brain or lymphatic system, relative to the parent species.

Pharmaceutically acceptable salts of the compounds according to the invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g. sodium), alkaline earth metal (e.g., magnesium), ammonium, $NW_4^+$ (wherein W is $C_{1-4}$ alkyl) and other amine salts. Physiologically acceptable salts of a hydrogen atom or an amino group include salts or organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as $Na^+$, $NH_4^+$, and $NW_4^+$ (wherein W is a $C_{1-4}$alkyl group). Preferred salts include sodium, calcium, potassium, choline, meglumine, and quaternary ammonium.

Other compounds of this invention may be prepared by one skilled in the art following the teachings of the specification coupled with knowledge in the art using reagents that are readily synthesized or commercially available.

Any reference to any of the above compounds also includes a reference to a pharmaceutically acceptable salt thereof.

Salts of the compounds of the present invention may be made by methods known to a person skilled in the art. For example, treatment of a compound of the present invention with an appropriate base or acid in an appropriate solvent will yield the corresponding salt.

Esters of the compounds of the present invention are independently selected from the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

In such esters, unless otherwise specified, any alkyl moiety present advantageously contains from 1 to 18 carbon atoms, particularly from 1 to 6 carbon atoms, more particularly from 1 to 4 carbon atoms, Any cycloalkyl moiety present in such esters advantageously contains from 3 to 6 carbon atoms. Any aryl moiety present in such esters advantageously comprises a phenyl group.

Ethers of the compounds of the present invention include, but are not limited to methyl, ethyl, butyl and the like.

The present invention features a compound selected from the group consisting of:

7-(5-benzyl-4H-1,2,4-triazol-3-yl)-1,6-naphthyridin-8-ol;
7-[5-(4-fluorobenzyl)-4H-1,2,4-triazol-3-yl]-1,6-naphthyridin-8-ol;
7-(5-benzyl-4H-1,2,4-triazol-3-yl)-5-(1,1-dioxido-1,2-thiazinan-2-yl)1,6-naphthyridin-8-ol;
7-[5-(3-chlorobenzyl)-4H-1,2,4-triazol-3-yl]-1,6-naphthyridin-8-ol;
7-[5-(3-methoxybenzyl)-4H-1,2,4-triazol-3-yl]-1,6-naphthyridin-8-ol;
7-[5-(3,4-dimethoxybenzyl)-4H-1,2,4-triazol-3-yl]-1,6-naphthyridin-8-ol;
1-[7-(5-benzyl-4H-1,2,4-triazol-3-yl)-8-hydroxy-1,6-naphthyridin-5-yl]pyrrolidin-2-one;
1-{7-[5-(4-fluorobenzyl)-4H-1,2,4-triazol-3-yl]-8-hydroxy-1,6-naphthyridin-5-yl}pyrrolidin-2-one;
1-{7-[5-(4-fluorobenzyl)-4H-1,2,4-triazol-3-yl]-8-hydroxy-1,6-naphthyridin-5-yl}piperidin-2-one;
7-(5-benzyl-4H-1,2,4-triazol-3-yl)-5-bromo-1,6-naphthyridin-8-ol;
7-(5-benzyl-4H-1,2,4-oxadiazol-3-yl)-1,6-naphthyridin-8-ol;
5-(1,1-dioxido-1,2-thiazinan-2-yl)-7-[5-(4-fluorobenzyl)-4H-1,2,4-triazol-3-yl]-1,6-naphthyridin-8-ol;
7-[5-(4-chlorobenzyl)-4H-1,2,4,-triazol-3-yl]-5-(1,1-dioxido-1,2-thiazinan-2-yl)-1,6-naphthyridin-8-ol;
5-bromo-7-[5-(4-fluorobenzyl)-4H-1,2,4,-triazol-3-yl]-1,6-naphthyridin-8-ol;
7-[5-(4-fluorobenzyl)-4H-1,2,4,-triazol-3-yl]-5-(methylsulfonyl)-1,6-naphthyridin-8-ol;
7-[5-(4-fluorobenzyl)-4H-1,2,4,-triazol-3-yl]-5-(methylspiperazin-1-yl)-1,6-naphthyridin-8-ol;
7-[5-(4-fluorobenzyl)-4H-1,2,4,-triazol-3-yl]-5-(morpholin-4-yl)-1,6-naphthyridin-8-ol;
4-{7-[5-(4-fluorobenzyl)-4H-1,2,4-triazol-3-yl]-8-hydroxy-1,6-naphthyridin-5-yl}piperizin-2-one;
7-(5-benzyl-4H-1,3,4-oxadiazol-2-yl)-1,6-naphthyridin-8-ol;
7-[5-(4-fluorobenzyl-1,3,4-oxadiazol-2-yl]-1,6-naphthyridin-8-ol;
5-(1,1-dioxido-1,2-thiazinan-2-yl)-7-[5-(4-fluorobenzyl)-1,3,4-oxadiazol-2-yl]-1,6-naphthyridin-8-ol;
7-(5-benzyl-1H-1,2,4-triazol-3-yl)-5-(1-pyrrolindinyl-1,6-naphthyridin-8-ol;
7-[5-(4-fluorobenzyl)-1,2,4-oxodiazol-3-yl]-1,6-naphthyridin-8-ol;
1-{7-[5-(4-fluorobenzyl)-1,2,4-oxadiazol-3-yl]-8-hydroxy-1,6-naphthyridin-5-yl}-2-pyrrolidinone;
1-[7-(5-benzyl-1,3,4-oxadiazol-2-yl)-8-hydroxy-1,6-naphthyridin-5-yl]-2-pyrrolidinone;
4-[7-(5-benzyl-1,3,4-oxadiazol-2-yl)-8-hydroxy-1,6-naphthyridin-5-yl]-2-piperazinone;
2-{4-[7-(5-benzyl-1,3,4-oxadiazol-2-yl)-8-hydroxy-1,6-naphthyridin-5-yl]-1-piperazinyl}-N,N-dimethylacetamide;
7-(5-benzyl-1,3,4-oxadiazol-2-yl)-5-[4-(2-pyrazinyl)-1-piperazinyl]-1,6-naphthyridin-8-ol;
7-(5-benzyl-1,3,4-oxadiazol-2-yl)-5-[4-(methoxyanilino)-1,6-naphthyridin-8-ol;
7-[5-(4-chlorobenzyl)-4H-1,2,4-triazol-3-yl]-1,6-naphthyridin-8-ol;
7-[5-(2-phenylethyl)-4H-1,2,4-triazol-3-yl]-1,6-naphthyridin-8-ol;
7-[5-(1-naphthylmethyl)-4H-1,2,4-triazol-3-yl]-1,6-naphthyridin-8-ol;
5-(1,1-dioxido-1,2-thiazinan-2-yl)-7-[5-(2-phenylethyl)-4H-1,2,4-triazol-3-yl]-1,6-naphthyridin-8-ol;
7-[5-(pyridin-4-ylmethyl)-4H-1,2,4-triazol-3-yl]-1,6-naphthyridin-8-ol;
7-[5-(pyridin-3-ylmethyl)-4H-1,2,4-triazol-3-yl]-1,6-naphthyridin-8-ol;
5-(1,1-dioxido-1,2-thiazinan-2-yl)-7-[5-(3-methoxybenzyl)-4H-1,2,4-triazol-3-yl]-1,6-naphthyridin-8-ol;
5-(1,1-dioxido-1,2-thiazinan-2-yl)-7-[5-(pyridin-3-ylmethyl)-4H-1,2,4-triazol-3-yl]-1,6-naphthyridin-8-ol;
5-(1,1-dioxido-1,2-thiazinan-2-yl)-7-[5-(pyridin-4-ylmethyl)-4H-1,2,4-triazol-3-yl]-1,6-naphthyridin-8-ol;
5-(1,1-dioxido-1,2-thiazinan-2-yl)-7-[5-(pyridin-2-ylmethyl)-4H-1,2,4-triazol-3-yl]-1,6-naphthyridin-8-ol;
7-[5-(3,5-difluorobenzyl)-4H-1,2,4-triazol-3-yl]-5-(1,1-dioxido-1,2-thiazinan-2-yl)-1,6-naphthyridin-8-ol;
5-(1,1-dioxido-1,2-thiazinan-2-yl)-7-[5-(thien-2-ylmethyl)-4H-1,2,4-triazol-3-yl]-1,6-naphthyridin-8-ol;
5-(1,1-dioxido-1,2-thiazinan-2-yl)-7-[5-(3-fluorobenzyl)-4H-1,2,4-triazol-3-yl]-1,6-naphthyridin-8-ol;
7-[5-(3,4-difluorobenzyl)-4H-1,2,4-triazol-3-yl]-5-(1,1-dioxido-1,2-thiazinan-2-yl)-1,6-naphthyridin-8-ol;
7-[5-(2,3-difluorobenzyl)-4H-1,2,4-triazol-3-yl]-5-(1,1-dioxido-1,2-thiazinan-2-yl)-1,6-naphthyridin-8-ol;
7-[5-(cyclopentylmethyl)-4H-1,2,4-triazol-3-yl]-5-(1,1-dioxido-1,2-thiazinan-2-yl)-1,6-naphthyridin-8-ol;
7-[5-(4-fluorobenzyl)-4H-1,2,4-triazol-3-yl]-5-thiomorpholin-4-yl-1,6-naphthyridin-8-ol;
7-[5-(4-fluorobenzyl)-4H-1,2,4-triazol-3-yl]-5-piperidin-1-yl-1,6-naphthyridin-8-ol;
7-[5-(4-fluorobenzyl)-4H-1,2,4-triazol-3-yl]-5-piperizin-1-yl-1,6-naphthyridin-8-ol;
5-(1,1-dioxidothiomorpholin-4-yl)-7-[5-(4-fluorobenzyl)-4H-1,2,4-triazol-3-yl]-1,6-naphthyridin-8-ol;
7-[5-(4-fluorobenzyl)-4H-1,2,4-triazol-3-yl]-5-(4-hydroxypiperidin-1-yl)-1,6-naphthyridin-8-ol;
7-[5-(4-fluorobenzyl)-4H-1,2,4-triazol-3-yl]-5-(4-pyridin-2-ylpiperazin-1-yl)-1,6-naphthyridin-8-ol;
7-[5-(4-fluorobenzyl)-4H-1,2,4-triazol-3-yl]-5-{[2-(2-hydroxyethoxy)ethyl]piperazin-1-yl}-1,6-naphthyridin-8-ol;

5-(4-acetylpiperazin-1-yl)-7-[5-(4-fluorobenzyl)-4H-1,2,4-triazol-3-yl]-1,6-naphthyridin-8-ol;

7-[5-(4-fluorobenzyl)-4H-1,2,4-triazol-3-yl]-5-(4-pyrazin-2-ylpiperazin-1-yl)-1,6-naphthyridin-8-ol;

7-[5-(4-fluorobenzyl)-4H-1,2,4-triazol-3-yl]-5-[4-(2-morpholin-4-yl-2-oxoethyl)piperazin-1-yl]-1,6-naphthyridin-8-ol;

2-(4-{7-[5-(4-fluorobenzyl)-4H-1,2,4-triazol-3-yl]-8-hydroxy-1,6-naphthyridin-5-yl}piperazin-1-yl)-N-isopropylacetamide;

4-{7-[5-(4-fluorobenzyl)-1,3,4-oxadiazol-2-yl]-8-hydroxy-1,6-naphthyridin-5-yl}benzoic acid;

3-{7-[5-(4-fluorobenzyl)-1,3,4-oxadiazol-2yl]-8-hydroxy-1,6-naphthyridin-5-yl}-1,3-oxazolidin-2-one;

N-{7-[5-(4-fluorobenzyl)-1,3,4-oxadiazol-2-yl]-8-hydroxy-1,6-naphthyridin-5-yl}-5-methylpyridine-2-sulfonamide;

7-[5-(4-fluorobenzyl)-1,3,4-oxadiazol-2-yl]-5-(3-furyl)-1,6-naphthyridin-8-ol;

4-{7-[5-(4-fluorobenzyl)-1,3,4-oxadiazol-2-yl]-8-hydroxy-1,6-naphthyridin-5-yl}-N,N-dimethylbenzamide;

4-{7-[5-(4-fluorobenzyl)-1,3,4-oxadiazol-2-yl]-8-hydroxy-1,6-naphthyridin-5-yl}-N,N-dimethyl-3-oxopiperazine-1-carboxamide;

4-{7-[5-(4-fluorobenzyl)-1,3,4-oxadiazol-2-yl]-8-hydroxy-1,6-naphthyridin-5-yl}-N-isopropylbenzamide;

4-acetyl-1-{7-[5-(4-fluorobenzyl)-1,3,4-oxadiazol-2-yl]-8-hydroxy-1,6-naphthyridin-5-yl}piperazin-2-one;

7-[5-(4-fluorobenzyl)-1,3,4-oxadiazol-2-yl]-5-(1H-pyrazol-4-yl)-1,6-naphthyridin-8-ol;

5-(3,5-dimethylisoxazol-4-yl)-7-[5-(4-fluorobenzyl)-1,3,4-oxadiazol-2-yl]-1,6-naphthyridin-8-ol;

7-[5-(4-fluorobenzyl)-1,3,4-oxadiazol-2-yl]-5-pyridin-2-yl-1,6-naphthyridin-8-ol;

1-{7-[5-(4-fluorobenzyl)-1,3,4-oxadiazol-2-yl]-8-hydroxy-1,6-naphthyridin-5-yl}piperazin-2-one;

N-(3-{7-[5-(4-fluorobenzyl)-1,3,4-oxadiazol-2-yl]-8-hydroxy-1,6-naphthyridin-5-yl}phenyl)methanesulfonamide;

N-(3-{7-[5-(4-fluorobenzyl)-1,3,4-oxadiazol-2-yl]-8-hydroxy-1,6-naphthyridin-5-yl}phenyl)urea;

N-{7-[5-(4-fluorobenzyl)-1,3,4-oxadiazol-2-yl]-8-hydroxy-1,6-naphthyridin-5-yl}pentanamide;

7-[5-(4-fluorobenzyl)-1,3,4-oxadiazol-2-yl]-5-(1H-pyrrol-2-yl)-1,6-naphthyridin-8-ol;

1-{7-[5-(4-fluorobenzyl)-1,3,4-oxadiazol-2-yl])-8-hydroxy-1,6-naphthyridin-5-yl}-4-(methylsulfonyl)piperazin-2-one;

7-[5-(4-fluorobenzyl)-1,3,4-oxadiazol-2-yl]-5-pyrazin-2-yl-1,6-naphthyridin-8-ol;

7-[5-(4-fluorobenzyl)-1,3,4-oxadiazol-2-yl]-5-(1,3-thiazol-2-yl)-1,6-naphthyridin-8-ol;

N-(3-{7-[5-(4-fluorobenzyl)-1,3,4-oxadiazol-2-yl]-8-hydroxy-1,6-naphthyridin-5-yl}phenyl)-N'-isopropylurea;

N-(4-{7-[5-(4-fluorobenzyl)-1,3,4-oxadiazol-2-yl]-8-hydroxy-1,6-naphthyridin-5-yl}phenyl)acetamide;

N~2~-acetyl-N~1~-(1-(N-acetylglycyl)-4-{7-[5-(4-fluorobenzyl)-1,3,4-oxadiazol-2-yl]-8-hydroxy-1,6-naphthyridin-5-yl}-3-oxopiperazin-2-yl)-N~1~-(1-(N-acetylglycyl)-4-{7-[5-(4-fluorobenzyl)-1,3,4-oxadiazol-2-yl]-8-hydroxy-1,6-naphthyridin-5-yl}-5-oxopiperazin-2-yl)glycinamide;

methyl 3-(acetylamino)-5-{7-[5-(4-fluorobenzyl)-1,3,4-oxadiazol-2-yl]-8-hydroxy-1,6-naphthyridin-5-yl}benzoate;

1-{7-[5-(4-fluorobenzyl)-1,3,4-oxadiazol-2-yl]-8-hydroxy-1,6-naphthyridin-5-yl}tetrahydropyrimidin-2(1H)-one;

N'-{7-[5-(4-fluorobenzyl)-1,3,4-oxadiazol-2-yl]-8-hydroxy-1,6-naphthyridin-5-yl}-N,N-dimethylsulfamide;

1-{7-[5-(4-fluorobenzyl)-1,3,4-oxadiazol-2-yl]-8-hydroxy-1,6-naphthyridin-5-yl}imidazolidin-2-one;

1-(3-{7-[5-(4-fluorobenzyl)-1,3,4-oxadiazol-2-yl]-8-hydroxy-1,6-naphthyridin-5-yl}phenyl)ethanone;

7-[5-(4-fluorobenzyl)-1,3,4-oxadiazol-2-yl]-5-(6-methyl-1,1-dioxido-1,2,6-thiadiazinan-2-yl)-1,6-naphthyridin-8-ol;

7-[5-(4-fluorobenzyl)-1,3,4-oxadiazol-2-yl]-5-(5-methyl-1,1-dioxido-1,2,5-thiadiazolidin-2-yl)-1,6-naphthyridin-8-ol;

7-[5-(4-fluorobenzyl)-1,3,4-oxadiazol-2-yl]-5-[4-(methylthio)phenyl]-1,6-naphthyridin-8-ol;

7-[5-(4-fluorobenzyl)-1,3,4-oxadiazol-2-yl]-5-[2-(methylsulfonyl)phenyl]-1,6-naphthyridin-8-ol;

7-[5-(4-fluorobenzyl)-1,3,4-oxadiazol-2-yl]-5-[3-(methylsulfonyl)phenyl]-1,6-naphthyridin-8-ol;

7-[5-(4-fluorobenzyl)-1,3,4-oxadiazol-2-yl]-5-[4-(methylsulfonyl)phenyl]-1,6-naphthyridin-8-ol;

1-{7-[5-(4-fluorobenzyl)-1,3,4-oxadiazol-2-yl]-8-hydroxy-1,6-naphthyridin-5-yl}-3-(2-hydroxyethyl)imidazolidin-2-one;

7-[5-(4-fluorobenzyl)-1,3,4-oxadiazol-2-yl]-5-[3-(methylthio)phenyl]-1,6-naphthyridin-8-ol;

7-[5-(4-fluorobenzyl)-1,3,4-oxadiazol-2-yl]-5-[2-(methylthio)phenyl]-1,6-naphthyridin-8-ol;

7-[5-(4-fluorobenzyl)-1,3,4-oxadiazol-2-yl]-5-(1H-pyrrol-1-yl)-1,6-naphthyridin-8-ol;

N-(4-{7-[5-(4-fluorobenzyl)-1,3,4oxadiazol-2-yl]-8-hydroxy-1,6-naphthyridin-5-yl}phenyl)methanesulfonamide;

4-{7-[5-(4-fluorobenzyl)-1,3,4-oxadiazol-2-yl]-8-hydroxy-1,6-naphthyridin-5-yl}-N,N-dimethylbenzenesulfonamide;

2-{7-[5-(4-fluorobenzyl)-1,3,4-oxadiazol-2-yl]-8-hydroxy-1,6-naphthyridin-5-yl}-N-isopropylbenzenesulfonamide;

4-{7-[5-(4-fluorobenzyl)-1,3,4-oxadiazol-2-yl]-8-hydroxy-1,6-naphthyridin-5-yl}benzonitrile;

4-{7-[5-(4-fluorobenzyl)-1,3,4-oxadiazol-2-yl]-8-hydroxy-1,6-naphthyridin-5-yl}-N-isopropylbenzenesulfonamide;

2-{7-[5-(4-fluorobenzyl)-1,3,4-oxadiazol-2-yl]-8-hydroxy-1,6-naphthyridin-5-yl}-N,N-dimethylbenzenesulfonamide;

N-(4-{7-[5-(4-fluorobenzyl)-1,3,4-oxadiazol-2-yl]-8-hydroxy-1,6-naphthyridin-5-yl}phenyl)cyclopropanecarboxamide;

7-[5-(4-fluorobenzyl)-1,3,4-oxadiazol-2-yl]-5-(3-methyl-1H-pyrazol-1-yl)-1,6-naphthyridin-8-ol;

N-(4-{7-[5-(4-fluorobenzyl)-1,3,4-oxadiazol-2-yl]-8-hydroxy-1,6-naphthyridin-5-yl}phenyl)propanamide;

4-{7-[5-(4-fluorobenzyl)-1,3,4-oxadiazol-2-yl]-8-hydroxy-1,6-naphthyridin-5-yl}-N-methylbenzamide;

N-cyclopropyl-4-{7-[5-(4-fluorobenzyl)-1,3,4-oxadiazol-2-yl]-8-hydroxy-1,6-naphthyridin-5-yl}benzamide;

3-(4-fluorobenzyl)-7-[5-(4-fluorobenzyl)-1,3,4-oxadiazol-2-yl]-1,6-naphthyridin-8-ol;

N-(4-{7-[5-(4-fluorobenzyl)-1,3,4-oxadiazol-2-yl]-8-hydroxy-1,6-naphthyridin-5-yl}phenyl)-N'-methylurea;

N'-(4-{7-[5-(4-fluorobenzyl)-1,3,4-oxadiazol-2-yl]-8-hydroxy-1,6-naphthyridin-5-yl}phenyl)-N,N-dimethylurea;

3-{7-[5-(4-fluorobenzyl)-1,3,4-oxadiazol-2-yl]-8-hydroxy-1,6-naphthyridin-5-yl}-N-methylbenzenesulfonamide;

4-{7-[5-(4-fluorobenzyl)-1,3,4-oxadiazol-2-yl]-8-hydroxy-1,6-naphthyridin-5-yl}benzamide;

N-(4-{7-[5-(4-fluorobenzyl)-1,3,4-oxadiazol-2-yl]-8-hydroxy-1,6-naphthyridin-5-yl}phenyl)urea;

N-{7-[5-(4-fluorobenzyl)-1,3,4-oxadiazol-2-yl]-8-hydroxy-1,6-naphthyridin-5-yl}cyclopropanecarboxamide;

7-[5-(4-fluorobenzyl)-1,3,4-oxadiazol-2-yl]-8-hydroxy-1,6-naphthyridine-5-carboxamide;
N-{7-[5-(4-fluorobenzyl)-1,3,4-oxadiazol-2-yl]-8-hydroxy-1,6-naphthyridin-5-yl}-N-methylacetamide;
N-{7-[5-(4-fluorobenzyl)-1,3,4-oxadiazol-2-yl]-8-hydroxy-1,6-naphthyridin-5-yl}-N-methylacetamide;
N-{7-[5-(4-fluorobenzyl)-1,3,4-oxadiazol-2-yl]-8-hydroxy-1,6-naphthyridin-5-yl}butanamide;
N-{7-[5-(4-fluorobenzyl)-1,3,4-oxadiazol-2-yl]-8-hydroxy-1,6-naphthyridin-5-yl}propanamide;
5-[3,5-bis(trifluoromethyl)phenyl]-7-[5-(4-fluorobenzyl)-1,3,4-oxadiazol-2-yl]-1,6-naphthyridin-8-ol;
5-(4-chlorophenyl)-7-[5-(4-fluorobenzyl)-1,3,4-oxadiazol-2-yl]-1,6-naphthyridin-8-ol;
7-[5-(4-fluorobenzyl)-1,3,4-oxadiazol-2-yl]-5-[4-(trifluoromethoxy)phenyl]-1,6-naphthyridin-8-ol;
N-{7-[5-(4-fluorobenzyl)-1,3,4-oxadiazol-2-yl]-8-hydroxy-1,6-naphthyridin-5-yl}-3-methylbutanamide;
N-{7-[5-(4-fluorobenzyl)-1,3,4-oxadiazol-2-yl]-8-hydroxy-1,6-naphthyridin-5-yl}-2-propylpentanamide;
7-[5-(4-fluorobenzyl)-1,3,4-oxadiazol-2-yl]-8-hydroxy-N-methyl-1,6-naphthyridine-5-carboxamide;
7-[5-(4-fluorobenzyl)-1,3,4-oxadiazol-2-yl]-5-(morpholin-4-ylcarbonyl)-1,6-naphthyridin-8-ol;
N'-acetyl-7-[5-(4-fluorobenzyl)-1,3,4-oxadiazol-2-yl]-8-hydroxy-1,6-naphthyridine-5-carbohydrazide;
N-{7-[5-(4-fluorobenzyl)-1,3,4-oxadiazol-2-yl]-8-hydroxy-1,6-naphthyridin-5-yl}-2-(2-oxopyrrolidin-1-yl)acetamide;
7-[5-(4-fluorobenzyl)-1,3,4-oxadiazol-2-yl]-8-hydroxy-N-morpholin-4-yl-1,6-naphthyridine-5-carboxamide;
ethyl 1-{7-[5-(4-fluorobenzyl)-1,3,4-oxadiazol-2-yl]-8-hydroxy-1,6-naphthyridin-5-yl}-2-oxopiperidine-3-carboxylate;
7-[5-(4-fluorobenzyl)-1,3,4-oxadiazol-2-yl]-8-hydroxy-N'-(methoxyacetyl)-1,6-naphthyridine-5-carbohydrazide;
7-[5-(4-fluorobenzyl)-1,3,4-oxadiazol-2-yl]-8-hydroxy-N-methoxy-1,6-naphthyridine-5-carboxamide;
7-[5-(4-fluorobenzyl)-1,3,4-oxadiazol-2-yl]-8-hydroxy-N-(2-methoxyethyl)-1,6-naphthyridine-5-carboxamide;
1-benzyl-N-{7-[5-(4-fluorobenzyl)-1,3,4-oxadiazol-2-yl]-8-hydroxy-1,6-naphthyridin-5-yl}-5-oxopyrrolidine-3-carboxamide;
7-[5-(4-fluorobenzyl)-1,3,4-oxadiazol-2-yl]-5-[(4-hydroxypiperidin-1-yl)carbonyl]-1,6-naphthyridin-8-ol;
N-1~-{7-[5-(4-fluorobenzyl)-1,3,4-oxadiazol-2-yl]-8-hydroxy-1,6-naphthyridin-5-yl}-N-1-,N-2-,N-2-trimethylethanediamide;
7-[5-(4-fluorobenzyl)-1,3,4-oxadiazol-2-yl]-5-(methylamino)-1,6-naphthyridin-8-ol;
5-chloro-7-[5-(4-fluorobenzyl)-1,3-oxazol-2-yl]-1,6-naphthyridin-8-ol;
1-{7-[5-(4-fluorobenzyl)-1,3-oxazol-2-yl]-8-hydroxy-1,6-naphthyridin-5-yl}-3-methylimidazolidin-2-one;
7-[5-(4-fluorobenzyl)-1,3,4-oxadiazol-2-yl]-8-hydroxy-N-(3-hydroxypropyl)-1,6-naphthyridine-5-carboxamide;
4-({7-[5-(4-fluorobenzyl)-1,3,4-oxadiazol-2-yl]-8-hydroxy-1,6-naphthyridin-5-yl}carbonyl)piperazin-2-one;
7-[5-(4-fluorobenzyl)-1,3,4-oxadiazol-2-yl]-5-[(4-methylpiperazin-1-yl)carbonyl]-1,6-naphthyridin-8-ol;
methyl N-({7-[5-(4fluorobenzyl)-1,3,4-oxadiazol-2-yl]-8-hydroxy-1,6-naphthyridin-5-yl}carbonyl)glycinate;
7-[5-(4-fluorobenzyl)-1,3,4-oxadiazol-2-yl]-8-hydroxy-N-(1,3-thiazol-2-yl)-1,6-naphthyridine-5-carboxamide;
7-[5-(4-fluorobenzyl)-1,3,4-oxadiazol-2-yl]-8-hydroxy-N-isopropyl-1,6-naphthyridine-5-carboxamide;
N-(4-{7-[5-(4-fluorobenzyl)-1,3-oxazol-2-yl]-8-hydroxy-1,6-naphthyridin-5-yl}phenyl)methanesulfonamide;
7-[5-(4-fluorobenzyl)-1,3,4-oxadiazol-2-yl]-8-hydroxy-N-(2-hydroxyethyl)-1,6-naphthyridine-5-carboxamide;
and pharmaceutically acceptable derivatives thereof.

Compounds of the present invention are useful as integrase inhibitors. One aspect of the instant invention relates to methods of treating or preventing viral infection, for example an HIV infection, in a biological sample comprising contacting the biological sample with compounds of formula I or pharmaceutically acceptable derivatives thereof. Another aspect of the instant invention relates to methods of treating or preventing viral infection, for example, an HIV infection, in a patient comprising administering to the patient a therapeutically effective amount of compounds of formula I or pharmaceutically acceptable derivatives thereof.

The compounds according to the invention are particularly suited to the treatment or prophylaxis of HIV infections and associated conditions. Reference herein to treatment extends to prophylaxis as well as the treatment of established infections, symptoms, and associated clinical conditions such as AIDS related complex (ARC), Kaposi's sarcoma, and AIDS dementia.

According to one embodiment of the invention, compounds of formula I or salts thereof may be formulated into compositions. In a preferred embodiment, the composition is a pharmaceutical composition, which comprises a compound of formula I and pharmaceutically acceptable carrier, adjuvant or vehicle. In one embodiment, the composition comprises an amount of a compound of the present invention effective to treat or prevent viral infection, for example an HIV infection, in a biological sample or in a patient. In another embodiment, compounds of this invention and pharmaceutical compositions thereof, which comprise an amount of a compound of the present innovation effective to inhibit viral replication or to treat or prevent a viral infection or disease or disorder, for example an HIV infection, and a pharmaceutically acceptable carrier, adjuvant or vehicle, may be formulated for administration to a patient, for example, for oral administration.

The present invention features compounds according to the invention for use in medical therapy, for example for the treatment or prophylaxis of a viral infection, for example an HIV infection and associated conditions. The compounds according to the invention are especially useful for the treatment of AIDS and related clinical conditions such as AIDS related complex (ARC), progressive generalized lymphadenopathy (PGL), Kaposi's sarcoma, thromobocytopenic purpura, AIDS-related neurological conditions such as AIDS dementia complex, multiple sclerosis or tropical paraperesis, anti-HIV antibody-positive and HIV-positive conditions, including such conditions in asymptomatic patients.

According to another aspect, the present invention provides a method for the treatment or prevention of the symptoms or effects of a viral infection in an infected patient, for example, a mammal including a human, which comprises administering to said patient a pharmaceutically effective amount of a compound according to the invention. According to one aspect of the invention, the viral infection is a retroviral infection, in particular an HIV infection.

The present invention further includes the use of a compound according to the invention in the manufacture of a medicament for administration to a subject for the treatment of a viral infection, in particular and HIV infection.

The compounds according to the invention may also be used in adjuvant therapy in the treatment of HIV infections or HIV-associated symptoms or effects, for example Kaposi's sarcoma.

The present invention further provides a method for the treatment of a clinical condition in a patient, for example, a mammal including a human which clinical condition includes those which have been discussed hereinbefore, which comprises treating said patient with a pharmaceutically effective amount of a compound according to the invention. The present invention also includes a method for the treatment or prophylaxis of any of the aforementioned diseases or conditions.

Reference herein to treatment extends to prophylaxis as well as the treatment of established conditions, disorders and infections, symptoms thereof, and associated. The above compounds according to the invention and their pharmaceutically acceptable derivatives may be employed in combination with other therapeutic agents for the treatment of the above infections or conditions. Combination therapies according to the present invention comprise the administration of a compound of the present invention or a pharmaceutically acceptable derivative thereof and another pharmaceutically active agent. The active ingredient(s) and pharmaceutically active agents may be administered simultaneously (i.e., concurrently) in either the same or different pharmaceutical compositions or sequentially in any order. The amounts of the active ingredient(s) and pharmaceutically active agent(s) and the relative timings of administration will be selected in order to achieve the desired combined therapeutic effect.

Examples of such therapeutic agents include, but are not limited to, agents that are effective for the treatment of viral infections or associated conditions. Among these agents are (1-alpha, 2-beta, 3-alpha)-9-[2,3-bis(hydroxymethyl)cyclobutyl]guanine [(−)BHCG, SQ-34514, lobucavir]; 9-[(2R, 3R,4S)-3,4-bis(hydroxy methyl)2-oxetanosyl]adenine (oxetanocin-G); acyclic nucleosides, for example acyclovir, valaciclovir, famciclovir, ganciclovir, and penciclovir; acyclic nucleoside phosphonates, for example (S)-1-(3-hydroxy-2-phosphonyl-methoxypropyl)cytosine (HPMPC), [[[2-(6-amino-9H-purin-9-yl)ethoxy]methyl]phosphinylidene]bis (oxymethylene)-2,2-dimethyl propanoic acid (bis-POM PMEA, adefovir dipivoxil), [[(1R)-2-(6-amino-9H-purin-9-yl)-1-methylethoxy]methyl]phosphonic acid (tenofovir), and (R)-[[2-(6-Amino-9H-purin-9-yl)-1-methylethoxy]methyl] phosphonic acid bis-(isopropoxycarbonyloxymethyl)ester (bis-POC-PMPA); ribonucleotide reductase inhibitors, for example 2-acetylpyridine 5-[(2-chloroanilino)thiocarbonyl) thiocarbonohydrazone and hydroxyurea; nucleoside reverse transcriptase inhibitors, for example 3'-azido-3'-deoxythymidine (AZT, zidovudine), 2',3'-dideoxycytidine (ddC, zalcitabine), 2',3'-dideoxyadenosine, 2',3'-dideoxyinosine (ddI, didanosine), 2',3'-didehydrothymidine (d4T, stavudine), (−)-beta-D-2,6-diaminopurine dioxolane (DAPD), 3'-azido-2',3'-dideoxythymidine-5'-H-phosphophonate(phosphonovir), 2'-deoxy-5-iodo-uridine(idoxuridine), (−)-cis-1-(2-hydroxymethyl)-1,3-oxathiolane 5-yl)-cytosine (lamivudine), cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (−)-cis-4-[2-amino-6-(cyclo-propylamino)-9H-purin-9-yl]-2-cyclopentene-1-methanol(abacavir), 9-[4-hydroxy-2-(hydroxymethyl)but-1-yl]-guanine (H2G), ABT-606 (2HM-H2G) and ribavirin; protease inhibitors, for example indinavir, ritonavir, nelfinavir, amprenavir, saquinavir, fosamprenavir, (R)—N-tert-butyl-3-[(2S,3S)-2-hydroxy-3-N—[(R)-2-N-(isoquinolin-5-yloxyacetyl)amino-3-methylthio-propanoyl]amino-4-phenylbutanoyl]-5,5-dimethyl-1,3-thiazolidine-4-carboxamide (KNI-272), 4R-(4alpha, 5alpha,6beta)]-1,3-bis [(3-aminophenyl)methyl]hexahydro-5,6-dihydroxy-4,7-bis (phenylmethyl)-2H-1,3-diazepin-2-one dimethanesulfonate (mozenavir), 3-[1-[3-[2-(5-trifluoromethylpyridinyl)-sulfonylamino]phenyl]propyl]-4-hydroxy-6alpha-phenethyl-6beta-propyl-5,6-dihydro-2-pyranone (tipranavir), N'-[2(S)-Hydroxy-3(S)—[N-(methoxycarbonyl)-1-tert-leucylamino]-4-phenylbutyl-N $^{alpha}$-(methoxycarbonyl)-N'-[4-(2-pyridyl)benzyl]-L-tert-leucylhydrazide (BMS-232632), 3-(2(S)-Hydroxy-3(S)-(3-hydroxy-2-methylbenzamido)-4-phenylbutanoyl)-5,5-dimethyl-N-(2-methylbenzyl)thiazolidine-4(R)-carboxamide (AG-1776), N-(2(R)-hydroxy-1(S)-indanyl)-2(R)-phenyl-methyl-4(S)-hydroxy-5-(1-(1-(4-benzo[b]furanylmethyl)-2 (S)—N'-(tert-butyl carboxamido)piperazinyl)pentanamide (MK-944A); interferons such as α-interferon; renal excretion inhibitors such as probenecid; nucleoside transport inhibitors such as dipyridamole, pentoxifylline, N-acetylcysteine (NAC), Procysteine, α-trichosanthin, phosphonoformic acid; as well as immunomodulators such as interleukin II or thymosin, granulocyte macrophage colony stimulating factors, erythropoetin, soluble $CD_4$ and genetically engineered derivatives thereof; non-nucleoside reverse transcriptase inhibitors (NNRTIs), for example nevirapine (BI-RG-587), alpha-((2-acetyl-5-methylphenyl)amino)-2,6-dichloro-benzeneacetamide(loviride), 1-[3-(isopropyl amino)-2-pyridyl]-4-[5-(methanesulfonamido)-1H-indol-2-ylcarbonyl]piperazine monomethanesulfonate(delavirdine), (10R, 11S, 12S)-12-Hydroxy-6,6,10,11-tetramethyl-4-propyl-11,12-dihydro-2H, 6H, 10H-benzo(1,2-b:3,4-b':5,6-b")tripyran-2-one ((+) calanolide A), (4S)-6-Chloro-4-[1E)-cyclopropyl ethenyl)-3, 4-dihydro-4-(trifluoromethyl)-2(1H)-quinazolinone (DPC-083), (S)-6-chloro-4-(cyclopropyl ethynyl)-1,4-dihydro-4-(trifluoromethyl)-2H-3,1-benzoxazin-2-one (efavirenz, DMP 266), 1-(ethoxy methyl)-5-(1-methylethyl)-6-(phenyl-methyl)-2,4(1H,3H)-pyrimidinedione (MKC-442), and 5-(3, 5-dichloro phenyl)thio-4-isopropyl-1-(4-pyridyl)methyl-1H-imidazol-2-ylmethyl carbamate(capravirine); glycoprotein 120 antagonists, for example PRO-2000, PRO-542 and 1,4-bis[3-[(2,4-dichlorophenyl)carbonyl amino]-2-oxo-5,8-disodiumsulfanyl]naphthalyl-2,5-dimethoxyphenyl-1,4-dihydrazone (FP-21399); cytokine antagonists, for example reticulose (Product-R), 1,1'-azobis-formamide (ADA), 1,11-(1,4-phenylenebis(methylene))bis-1,4,8,11-tetraazacyclotetradecane octahydrochloride (AMD-3100); integrase inhibitors; and fusion inhibitors, for example T-20 and T-1249.

The present invention further includes the use of a compound according to the invention in the manufacture of a medicament for simultaneous or sequential administration with at least another therapeutic agent, such as those defined hereinbefore.

Compounds of the present invention may be administered with an agent known to inhibit or reduce the metabolism of compounds, for example ritonavir. Accordingly, the present invention features a method for the treatment or prophylaxis of a disease as hereinbefore described by administration of a compound of the present invention in combination with a metabolic inhibitor. Such combination may be administered simultaneously or sequentially.

In general a suitable dose for each of the above-mentioned conditions will be in the range of 0.01 to 250 mg per kilogram body weight of the recipient (e.g. a human) per day, preferably in the range of 0.1 to 100 mg per kilogram body weight per day and most preferably in the range 0.5 to 30 mg per kilogram body weight per day and particularly in the range 1.0 to 20 mg per kilogram body weight per day. Unless otherwise indicated, all weights of active ingredient are calculated as the parent compound of formula (I); for salts or esters thereof, the weights would be increased proportionally. The desired dose may be presented as one, two, three, four, five, six or more sub-doses administered at appropriate intervals throughout the day. In some cases the desired dose may be given on alternative days. These sub-doses may be administered in unit dosage forms, for example, containing 10 to 1000 mg or 50 to 500 mg, preferably 20 to 500 mg, and most preferably 50 to 400 mg of active ingredient per unit dosage form.

While it is possible for the active ingredient to be administered alone, it is preferable to present it as a pharmaceutical composition. The compositions of the present invention comprise at least one active ingredient, as defined above, together with one or more acceptable carriers thereof and optionally other therapeutic agents. Each carrier must be acceptable in the sense of being compatible with the other ingredients of the composition and not injurious to the patient.

Pharmaceutical compositions include those suitable for oral, rectal, nasal, topical (including transdermal, buccal and sublingual), vaginal or parenteral (including subcutaneous, intramuscular, intravenous, intradermal, and intravitreal) administration. The compositions may conveniently be presented in unit dosage form and may be prepared by any methods well known in the art of pharmacy. Such methods represent a further feature of the present invention and include the step of bringing into association the active ingredients with the carrier, which constitutes one or more accessory ingredients. In general, the compositions are prepared by uniformly and intimately bringing into association the active ingredients with liquid carriers or finely divided solid carriers or both, and then if necessary shaping the product.

The present invention further includes a pharmaceutical composition as hereinbefore defined wherein a compound of the present invention or a pharmaceutically acceptable derivative thereof and another therapeutic agent are presented separately from one another as a kit of parts.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in *Pharmaceutical Research* 3(6), 318 (1986).

Pharmaceutical compositions of the present invention suitable for oral administration may be presented as discrete units such as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Pharmaceutical compositions suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions suitable for vaginal administration may be presented as pessaries, tampons, creams, gels, pastes, foams or spray. Pharmaceutical compositions may contain in addition to the active ingredient such carriers as are known in the art to be appropriate.

Pharmaceutical compositions for rectal administration may be presented as a suppository with a suitable carrier comprising, for example, cocoa butter or a salicylate or other materials commonly used in the art. The suppositories may be conveniently formed by admixture of the active combination with the softened or melted carrier(s) followed by chilling and shaping in molds.

Pharmaceutical compositions suitable for parenteral administration include aqueous and nonaqueous isotonic sterile injection solutions which may contain anti-oxidants, buffers, bacteriostats and solutes which render the pharmaceutical composition isotonic with the blood of the intended recipient; and aqueous and non-aqueous sterile suspensions which may include suspending agents and thickening agents; and liposomes or other microparticulate systems which are designed to target the compound to blood components or one or more organs. The pharmaceutical compositions may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Unit dosage pharmaceutical compositions include those containing a daily dose or daily subdose of the active ingredients, as hereinbefore recited, or an appropriate fraction thereof.

It should be understood that in addition to the ingredients particularly mentioned above the pharmaceutical compositions of this invention may include other agents conventional in the art having regard to the type of pharmaceutical composition in question, for example, those suitable for oral administration may include such further agents as sweeteners, thickeners and flavoring agents.

The compounds of the present invention may be prepared according to the following reactions schemes and examples, or modifications thereof using readily available starting materials, reagents and conventional synthesis procedures. In these reactions, it is also possible to make use of variants which are known to those of ordinary skill in the art.

Compounds of the formula (I) wherein $R^1$ is H, A is a 1,2,4-triazole may be prepared by a general process outlined in scheme 1 below.

Scheme 1

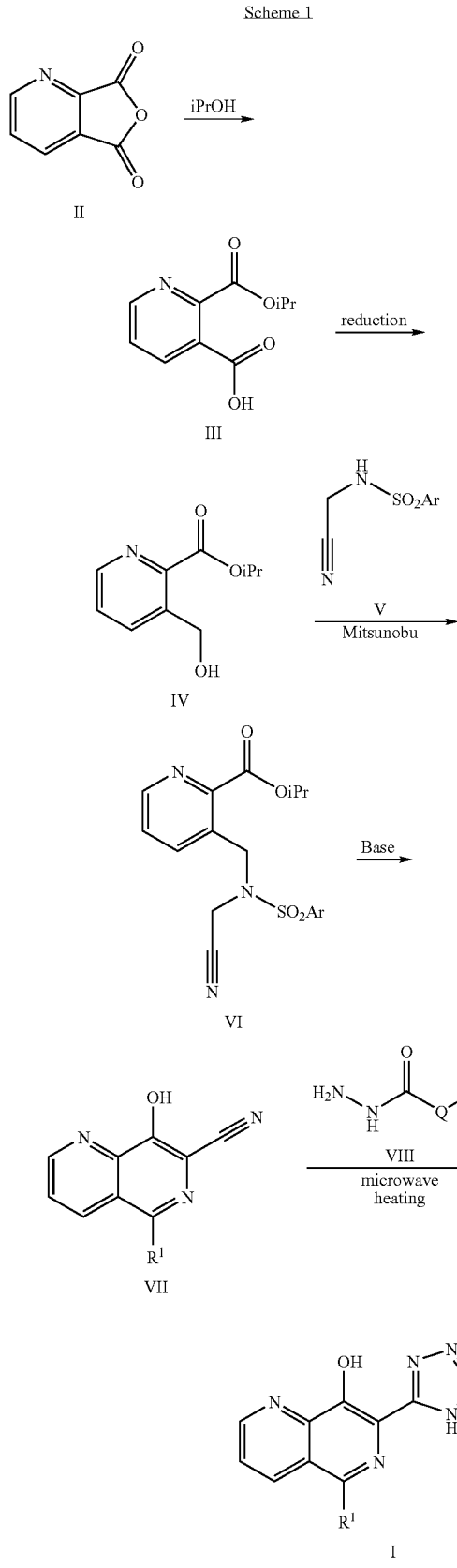

wherein:

R[1] is hydrogen, A is 1,2,4-triazole and all other substituents are as hereinbefore defined.

Generally, the process for preparing compounds of Formula (I) wherein R[1] is H, A is a 1,2,4-triazole ring comprises the steps of:

(a) reacting an anhydride of formula (II) with isopropanol to give an acid of formula (III);

(b) reduction of an acid of formula (III) to form an alcohol of formula (IV);

(c) displacement of the hydroxyl group in an alcohol of formula (IV) with a sulfonylated aminoacetonitrile derivative of formula (V) to give a compound of formula (VI);

(d) cyclization of a compound of formula (VI) to give a compound of formula (VII);

(e) condensation of a compound of formula (VII) with a hydrazide of formula (VIII) to give a compound of Formula (I).

More specifically, compounds of Formula (I) wherein R[1] is H, A is a 1,2,4-triazole can be prepared by reacting a compound of formula (VII) with a hydrazide of general formula (VIII)

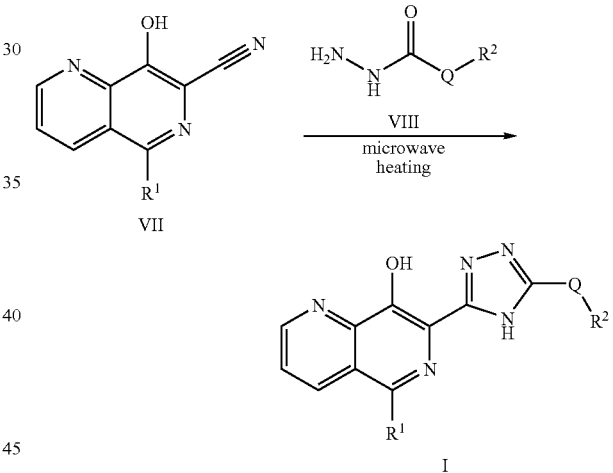

wherein all variables are as defined above in connection with Scheme 1.

This general method can readily be carried out by combining a compound of formula (VII) with a compound of formula (VIII) in a suitable solvent, optionally in the presence of an acid, and heating the mixture with a microwave source at 150-200° C. Typical solvents include but are not limited to 1,4-dioxane, 1-methylpyrrolidin-2-one and the like. The acid is typically acetic acid and the like. In one embodiment the solvent is 1,4-dioxane and the acid is acetic acid. In another embodiment the solvent is 1-methylpyrrolidin-2-one and the acid is acetic acid. Compound of the formula (VIII) are either commercially available or can be made by methods commonly known to those skilled in the art.

Compounds of the general formula (VII) can be made by cyclization of a compound of formula (VI)

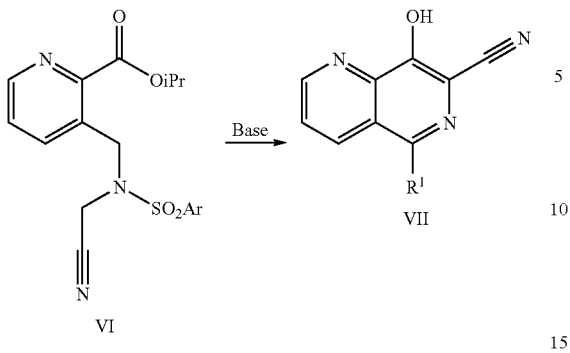

wherein all variables are as defined above in connection with Scheme 1.

Typically a compound of formula (VI) in a suitable solvent is treated with a base optionally with heating to 50 to 100° C. Suitable solvents include but are not limited to the lower alcohols such as methanol and ethanol, 1-methylpyrrolidin-2-one, N,N-dimethylformamide, tetrahydrofuran, toluene and the like. Bases include by way of example sodium ethoxide, sodium methoxide, sodium tert-butoxide, lithium bis-trimethylsilylamide, sodium hydride and the like.

Compounds of formula (VI) can be readily prepared by reacting a compound of formula (V) with an alcohol of formula (IV)

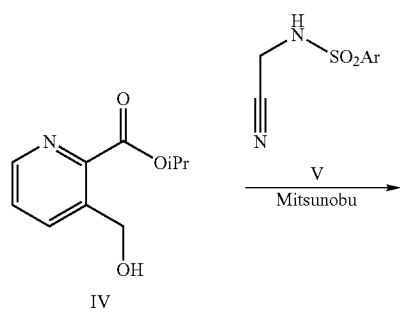

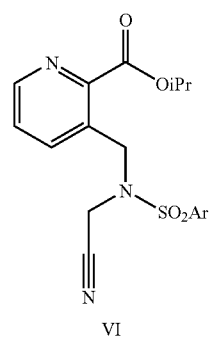

wherein all variables are as defined above in connection with Scheme 1.

Typically an alcohol of formula (IV) is reacted with a sulfonylated aminoacetonitrile derivative of formula (V) under conditions know to those skilled in the art as a Mitsunobu reaction. This reaction is typically carried out in an inert solvent a 0° C. to ambient temperature in the presence of a dialkyldiazodicarboxylate and triphenyl phosphine. Suitable solvents include tetrahydrofuran and the like. Typically the dialkyldiazodicarboxylate is diethyl- or diisopropyldiazodicaboxylate. The compound of formula (IV) can be readily prepared as described in P. Ornstein et. al. *J. Med. Chem.* 1989, 32, 827.

Compounds of the formula (I) wherein $R^1$ is H, A is a 1,3,4-oxadiazole may be prepared by a general process outlined in Scheme 2 below Scheme 2

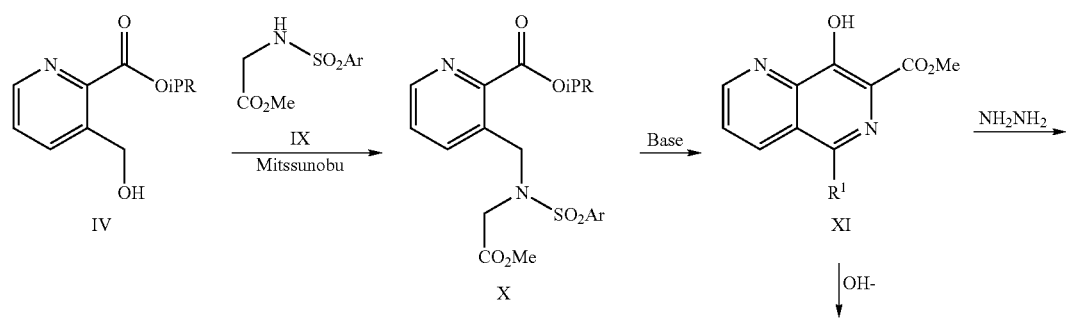

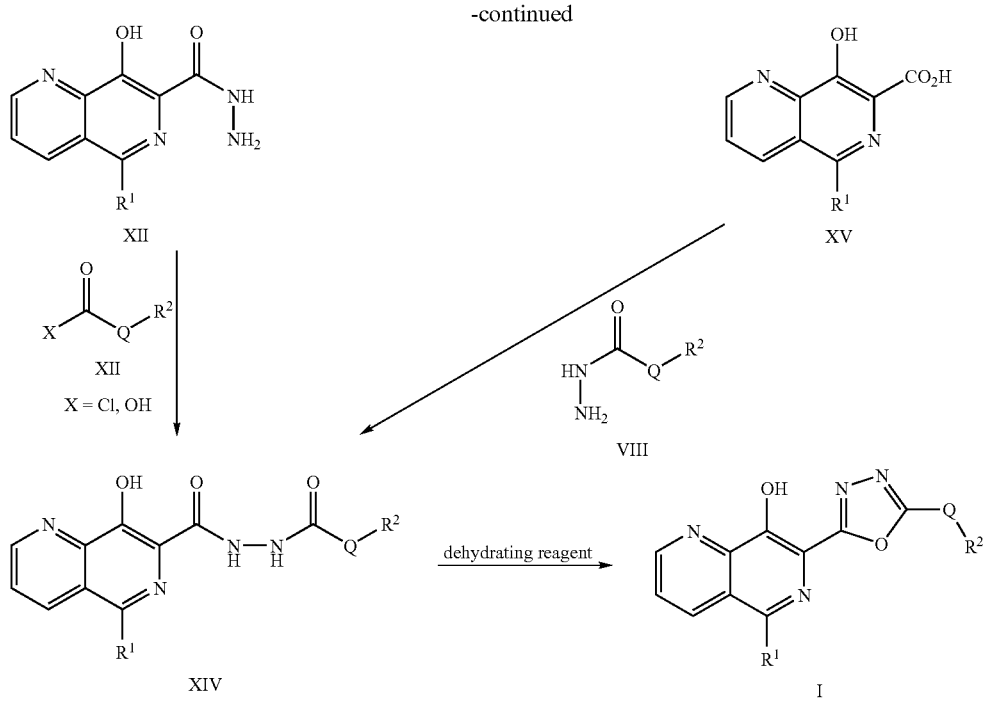

wherein:

$R^1$ is hydrogen, A is 1,2,4-oxadiazole and all other substituents are as hereinbefore defined Generally, the process for preparing compounds of Formula (I) wherein $R^1$ is H, A is a 1,3,4-oxadiazole comprises the steps of:

a) displacement of the hydroxyl group in an alcohol of formula (IV) with a sulfonylated glycine derivative of formula (IX) to give a compound of formula (X);

b) cyclization of a compound of formula (X) to give a compound of formula (XI);

c) either—

1) reacting a compound of formula (XI) with a hydrazine to give a hydrazide of formula (XII);

2) coupling a hydrazide of formula (XII) with an acid or acid derivative of formula (XIII) to form a compound of formula (XIV);

d) or—

1) hydrolyzing a compound of formula (XI) to an acid of formula (XV);

2) coupling an acid of formula (XV) with a hydrazide of formula (VIII) to give a compound of formula (XIV);

e) and—reacting a compound of formula (XIV) with a dehydrating reagent to form a compound of formula (I);

More specifically, compounds of formula (I) wherein $R^1$ is H, A is a 1,3,4-oxadiazole can be prepared by reacting a compound of formula (XIV) with a dehydrating reagent

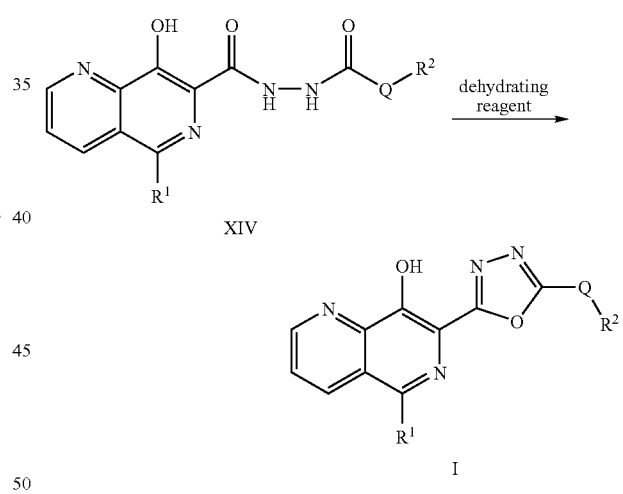

wherein all variables are as defined above in connection with scheme 2.

This general method can readily be carried out using common dehydrating agents or conditions well known to one skilled in the art optionally in an inert solvent. Representative conditions are defined as but not limited to (methoxycarbonylsulfamoyl)triethylammonium hydroxide, inner salt (commonly referred to as the Burgess reagent), triphenylphosphine and an activating agent such as iodine or carbon tetrachloride optionally in the presence of a base such as imidazole or triethylamine, phosphorous oxychloride and the like. These reagents can optionally be used in an inert solvent such as chloroform, dichloromethane, 1-methylpyrrolidin-2-one, N,N-dimethylformamide, tetrahydrofuran, toluene and the like.

Compounds of the formula (XIV) may be readily prepared by reacting a compound of formula (XII) with an acid (X=OH) of formula (XIII) in the presence of a coupling reagent or an acid chloride (X=Cl) of formula (XIII) optionally in the presence of a base in an inert solvent,

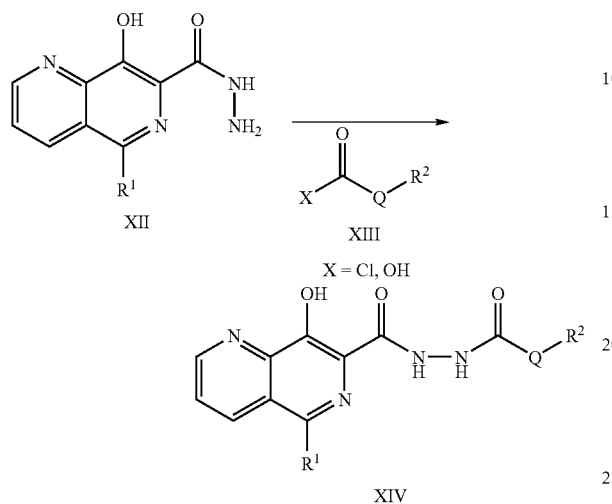

wherein all variables are as defined above in connection with scheme 2.

Typically, the coupling reagents include but are not limited to 1-(3-dimethylaminopropyl)-3-ethylcarbodiimide hydrochloride, dicyclohexylcarbodiimide, carbonyl di-imidazole and the like. Typical solvents include by way of example dichloromethane, and N,N-dimethylformamide. The coupling of an acid chloride of formula (XIII) to a compound of formula (XII) can be readily carried out by numerous conditions well known to one skilled in the art and prevalent in the literature. Typical conditions may involve an inert solvent such as dichloromethane and the presence of a base such as pyridine or triethylamine or in pyridine neat.

Compounds of general formula (XII) can be prepared from a compound of formula (XI). According to this method, the compound of formula (XI) is treated with hydrazine in an inert solvent optionally with heating,

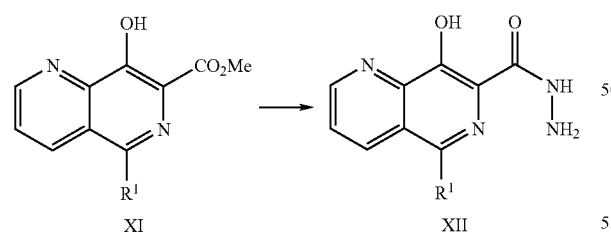

wherein all variables are as defined above in connection with scheme 2.

An alternative strategy to form a compound of formula XIV involves coupling an acid of formula (XV) with a hydrazide of formula (VIII). Typically, the coupling reagents include but are not limited to 1-(3-dimethylaminopropyl)-3-ethylcarbodiimide hydrochloride, dicyclohexylcarbodiimide, carbonyl di-imidazole and the like. Typical solvents include by way of example dichloromethane, and N,N-dimethylformamide.

The compound of formula (XV) can be readily prepared by hydrolysis of a compound of formula (XI). Typical conditions for this type of hydrolysis reaction involve treating a compound of formula (XI) with aqueous sodium hydroxide or lithium hydroxide in an inert solvent such as tetrahydrofuran, or methanol or mixtures of methanol, tetrahydrofuran and water.

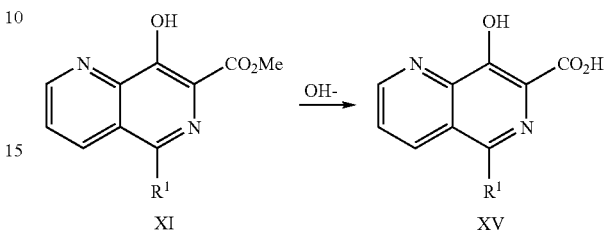

Compounds of the formula (XI) can readily be prepared according to the methods described in the literature, for example in WO 02/30930.

A variation of the above methods described in schemes 1 and 2 involves preparation of compounds of the formula (I) wherein $R^1$ is halogen and all other variables are in accordance with the general formula. These compounds of formula (I) may be prepared in an analogous manner as previously outlined provided the additional halogenation step shown in scheme 3 is inserted into the synthetic sequence,

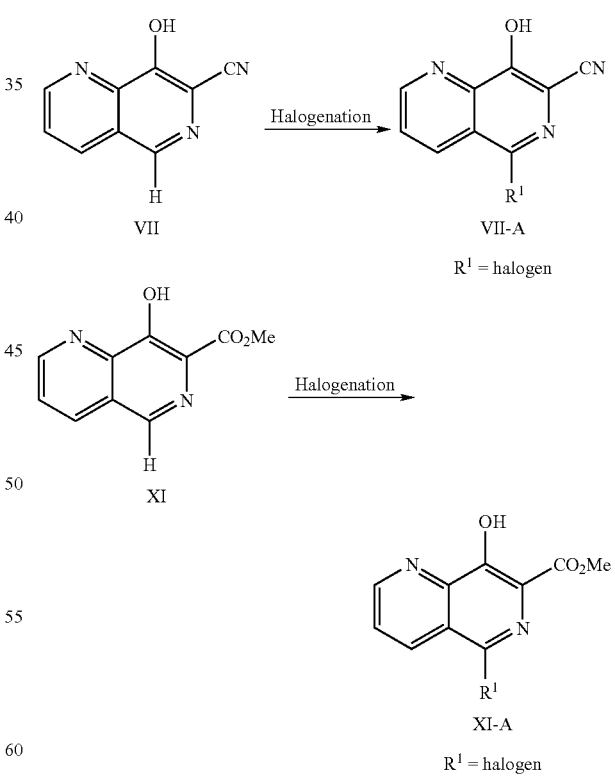

wherein $R^1$ is halogen and all other substituents are as hereinbefore defined.

Generally, the process for preparing compounds of the formula (I) wherein $R^1$ is halogen involves all the steps outlined for scheme 1 or 2 plus the halogenation of a compound of formula (VII) or (XI) to give compound of formula (VII-A) or (XI-A) respectively.

More specifically, compounds of formula (VII-A) or (XI-A) wherein $R^1$ is halogen, can be prepared by reacting a compound of formula (VII) or (XI) with an eletrophilic halogenating reagent in an inert solvent optionally with heating. By way of example, halogenating reagents include but are not limited to N-bromosuccinimide, bromine, iodine, iodine monochloride, N-chlorosuccinimide, tetraalkylammonium tribromides and the like. Solvents include but are not limited to 1-methylpyrrolidin-2-one, N,N-dimethylformamide, tetrahydrofuran, dichloromethane, chloroform, acetic acid and the like.

An alternative route to compounds of the formula (I) wherein $R^1$ is H, halogen; A is a 1,3,4 oxadiazole is outlined in scheme 4 below.

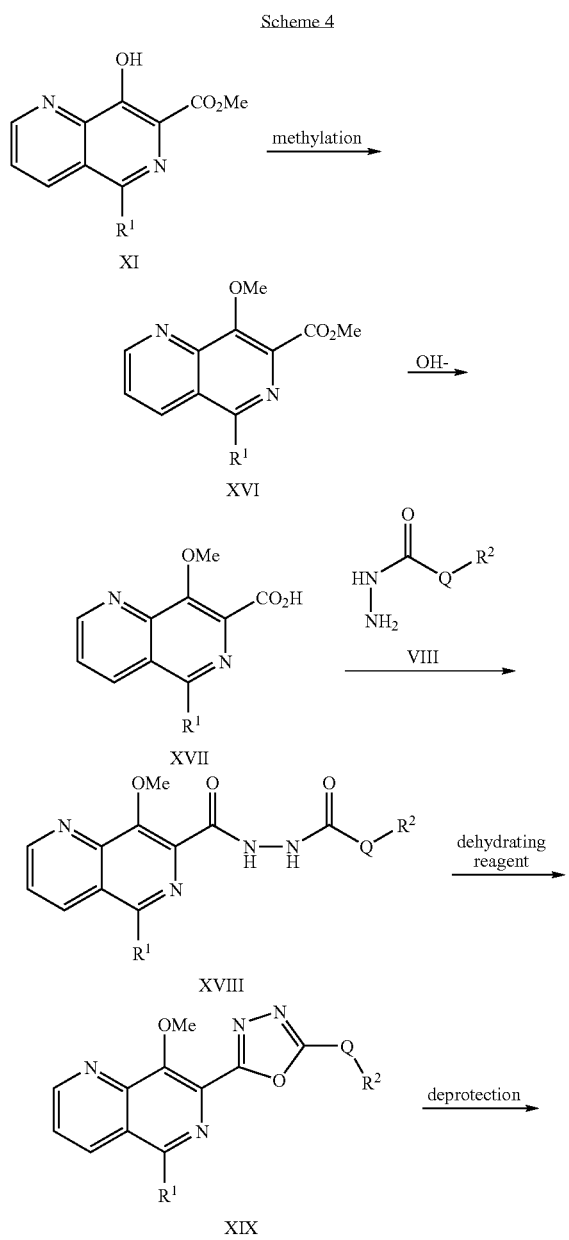

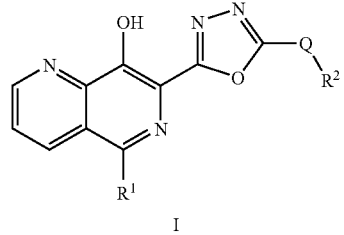

wherein $R^1$ is hydrogen, halogen, A is 1,3,4-oxadiazole and all other substituents are as hereinbefore defined.

Generally, the process for preparing compounds of the formula (I) wherein $R^1$ is H, halogen, A is a 1,3,4-oxadiazole comprises the steps of:

a) Methylation of a compound of formula (XI) to provide a compound of formula (XVI);

b) Hydrolysis of an ester of formula (XVI) to give an acid of formula (XVII);

c) Coupling of an acid of formula (XVII) with a compound of formula (VIII) to give a compound of formula (XVIII);

d) Cyclization and dehydration of a compound of formula (XVIII) to give an oxadiazole of formula (XIX);

e) Demethylation of a compound of formula (XIX) to give a compound of formula (I).

More specifically, compounds of formula (I) wherein $R^1$ is H, A is a 1,3,4-oxadiazole can be prepared by demthylation of a compound of formula (XIX) with a Lewis acid in an inert solvent. Typically the Lewis acid is trimethylsilyl iodide formed in situ from the addition of sodium iodide and trimethylsilyl chloride. An inert solvent is acetonitrile and the like. Numerous variations of these conditions are well known to those skilled in the art as common deprotection conditions and can be readily found in the literature.

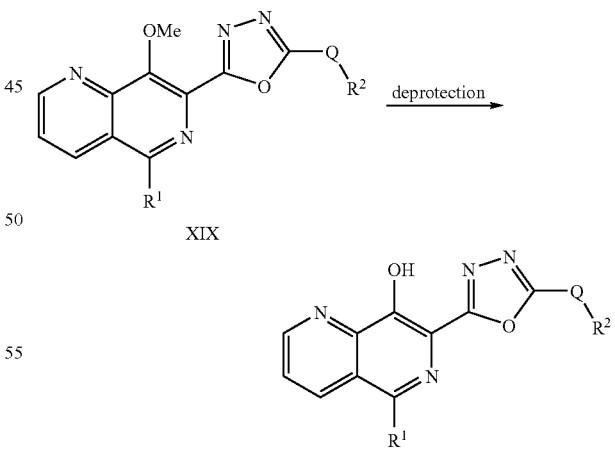

wherein all variables are as defined above in connection with Scheme 4.

Compounds of the formula (XIX) can be readily prepared by reacting a compound of formula (XVIII) with a dehydrating reagent.

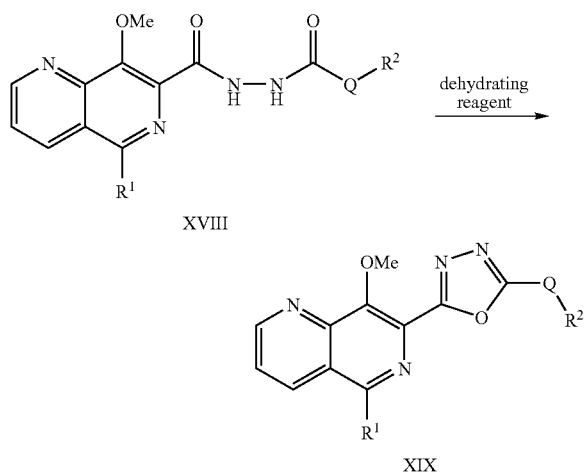

XVIII

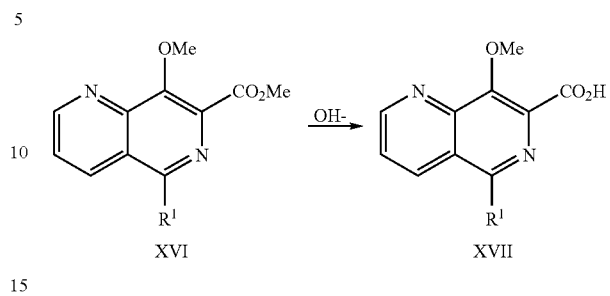

XVI → XVII

The compound of formula (XVII) can be readily prepared by hydrolysis of a compound of formula (XVI). Typical conditions for this type of hydrolysis reaction involve treating a compound of formula (XVI) with aqueous sodium hydroxide or lithium hydroxide in an inert solvent such as tetrahydrofuran, or methanol or mixtures of methanol, tetrahydrofuran and water.

Wherein all variables are as defined above in connection with Scheme 4.

XIX wherein all variables are as defined above in connection with Scheme 4.

This general method can readily be carried out using common dehydrating agents or conditions well known to one skilled in the art optionally in an inert solvent. Representative conditions are defined as but not limited to (methoxycarbonylsulfamoyl)triethylammonium hydroxide, inner salt (commonly referred to as the Burgess reagent), triphenylphosphine and an activating agent such as iodine or carbon tetrachloride optionally in the presence of a base such as imidazole or triethylamine, phosphorous oxychloride and the like. These reagents can optionally be used in an inert solvent such as chloroform, dichloromethane, 1-methylpyrrolidin-2-one, N,N-dimethylformamide, tetrahydrofuran, toluene and the like.

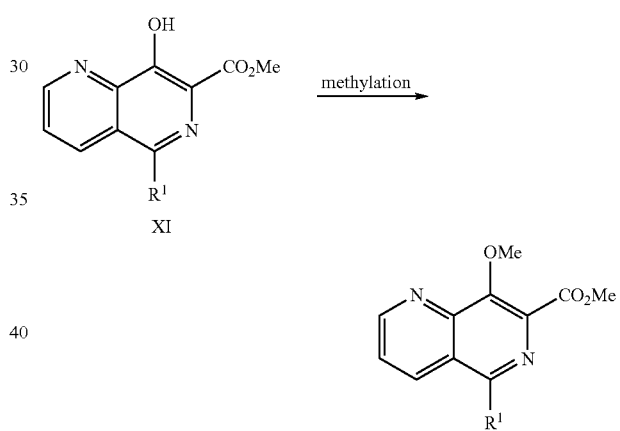

XI → (XVI)

Compounds of the formula (XVI) can be readily prepared by methylation of a compound of formula (XVI) using several standard conditions known to one skilled in the art.

Wherein all variables are as defined above in connection with Scheme 4.

Typically the methylation is carried out using a methyl halide or sulfate in an inert solvent optionally with a base. Useful methylating reagents include methyl iodide, dimethyl sulfate, methyl triflate, trimethyloxonium tetrafluoroborate, diazomethane, trimethylsilyldiazomethane and the like. Suitable bases include potassium carbonate, cesium carbonate, sodium hydroxide, sodium hydride and the like. Inert solvents include but are not limited to acetonitrile, 1-methylpyrrolidin-2-one, N,N-dimethylformamide, tetrahydrofuran and the like.

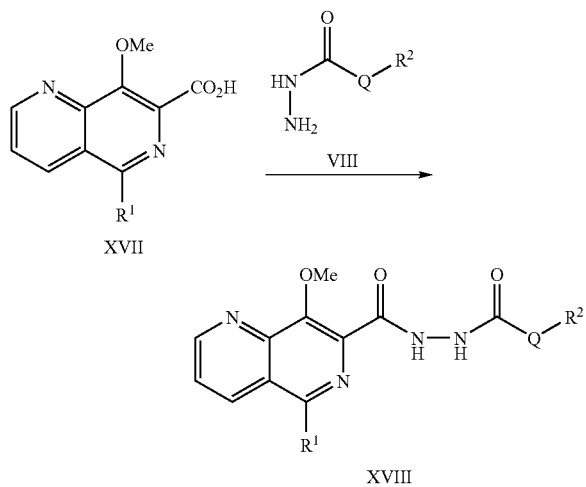

XVII → XVIII

Compounds of the formula (XVIII) may be readily prepared by reacting a compound of formula (XVII) with a compound of formula (VIII) in the presence of a coupling reagent in an inert solvent.

Wherein all variables are as defined above in connection with Scheme 4.

Typically, the coupling reagents include but are not limited to 1-(3-dimethylaminopropyl)-3-ethylcarbodiimide hydrochloride, dicyclohexylcarbodiimide, carbonyl di-imidazole and the like. Typical solvents include by way of example dichloromethane, and N,N-dimethylformamide.

Compounds of the formula (XI) can readily be prepared according to the methods described in the previous schemes.

Compounds of the formula (I) wherein $R^1$ is hydrogen, halogen, A is a 1,2,4-oxadiazole may be prepared by a general process outlined in scheme 5 below.

Scheme 5

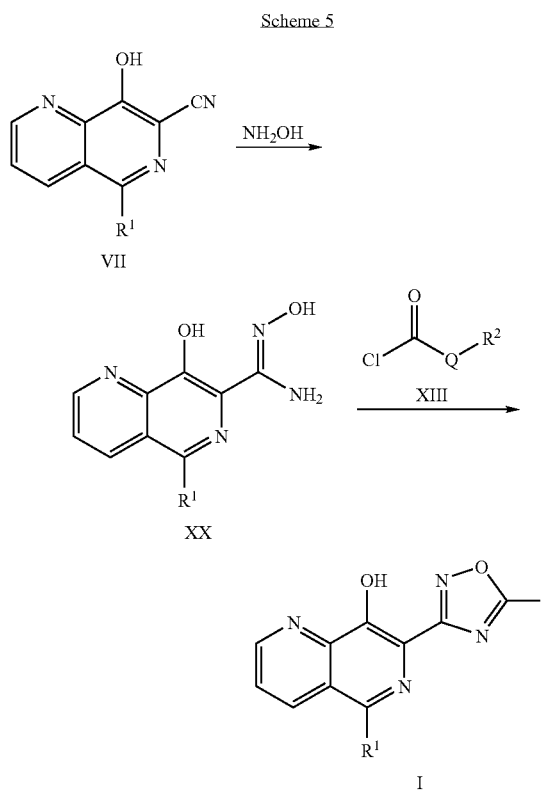

wherein R¹ is hydrogen, halogen, A is 1,2,4-triazole and all other substituents are as hereinbefore defined.

Generally, the process for preparing compounds of the formula (I) wherein R¹ is H, halogen, A is a 1,2,4-oxadiazole comprises the steps of:

a) Reacting a compound of formula (VII) with hydroxylamine to form a compound of formula (XX);

b) Condensing a compound of formula (XX) with an acid chloride to form a compound of formula (I).

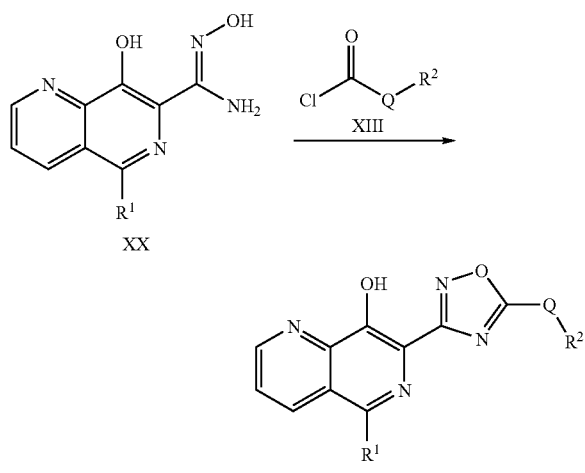

More specifically, compounds of formula (I) wherein R¹ is H, halogen; A is a 1,2,4-oxadiazole can be prepared by reacting a compound of formula (XX) with an acid chloride or equivalent reagent (XIII) optionally with heating in an inert solvent. In some cases a base may also be required.

Wherein all variables are as defined above in connection with Scheme 5.

Typically this reaction is performed in a solvent such as 1,4-dioxane, 1-methylpyrrolidin-2-one, N,N-dimethylformamide, tetrahydrofuran, toluene and the like. This condensation often may require heating to 50-200° C. Optionally, a microwave heating source can also be readily employed using an appropriate solvent as outlined above and heating to 50-200° C. Suitable bases include but are not limited to potassium carbonate, triethylamine and the like.

Compounds of the formula (XX) may be readily prepared by reacting a compound of formula (VII) with hydroxylamine hydrochloride in a solvent such as ethanol and the like. This reaction may optionally be heated to 40-80° C.

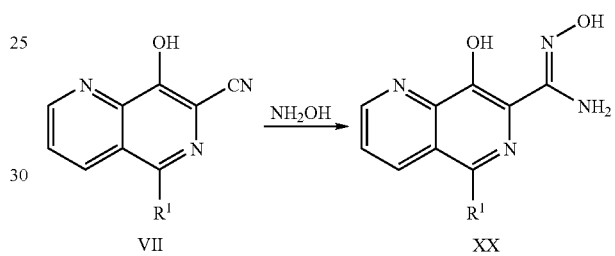

Wherein all variables are as defined above in connection with Scheme 5.

Compounds of the formula (VII) can readily be prepared according to the methods described in the previous schemes.

Compounds of the formula (I) wherein R¹ is H, halogen, A is a 1,3,4-thiadiazole may be prepared by a general process outlined in scheme 6 below.

Scheme 6

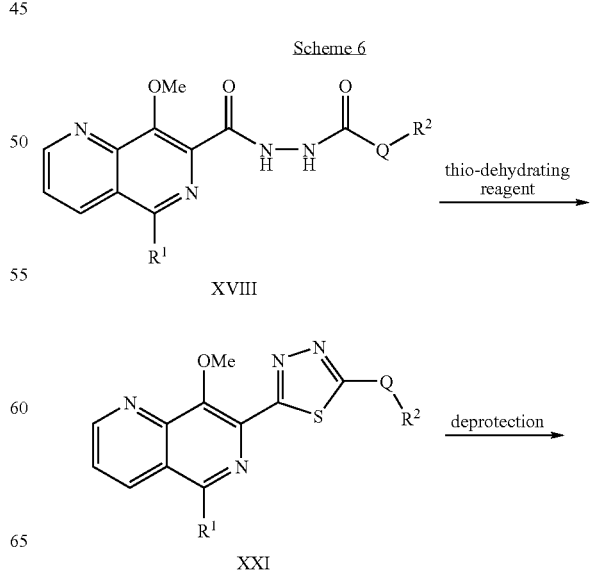

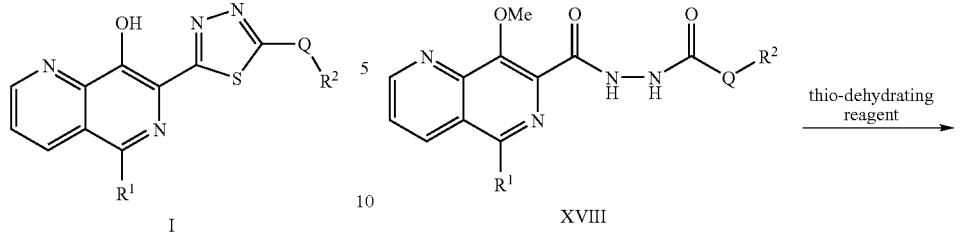

wherein $R^1$ is hydrogen, halogen, A is 1,3,4-thiadiazole and all other substituents are as hereinbefore defined.

Generally, the process for preparing compounds of the formula (I) wherein $R^1$ is H, halogen, A is a 1,3,4-thiadiazole comprises the steps of:

a) Cyclization of a compound of formula (XVIII) to give a thiadiazole of formula (XXI);

b) Demethylation of a compound of formula (XXI) to give a compound of formula (I).

More specifically, compounds of formula (I) wherein $R^1$ is H, halogen, A is a 1,3,4-thiadiazole can be prepared by demethylation of a compound of formula (XXI) with a Lewis acid in an inert solvent. Typically the Lewis acid is trimethylsilyl iodide formed in situ from the addition of sodium iodide and trimethylsilyl chloride. An inert solvent is acetonitrile and the like. Numerous variations of these conditions are well known to those skilled in the art as common deprotection conditions and can be readily found in the literature.

Wherein all variables are as defined above in connection with Scheme 4.

This general method can readily be carried out by heating a mixture of a compound of formula (XVIII) and Lawesson's reagent in a solvent such as toluene and the like.

Compounds of the formula (I) wherein A is a 4-pyrimidine may be prepared by a general process outlined in scheme 7 below.

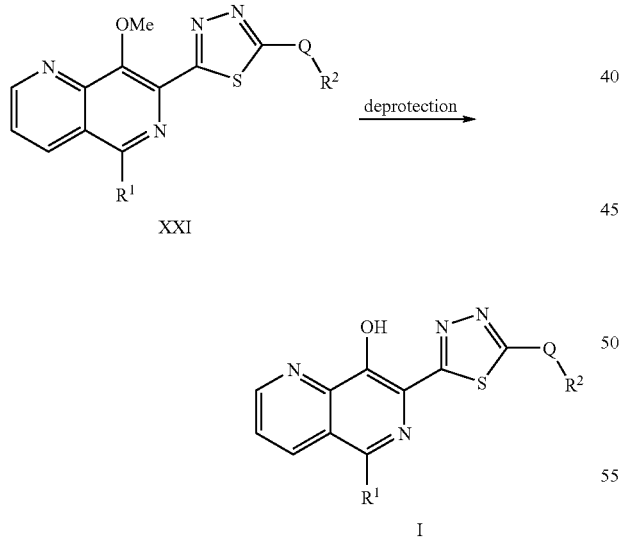

Wherein all variables are as defined above in connection with Scheme 6.

Compounds of the formula (XXI) can be readily prepared by reacting a compound of formula (XVIII) with Lawesson's reagent ([2,4-bis(4-methoxyphenyl)-1,3-dithia-2,4-diphosphetane-2,4-disulfide]) in an inert solvent or with $P_4S_{10}$ in a solvent such as pyridine by way of example.

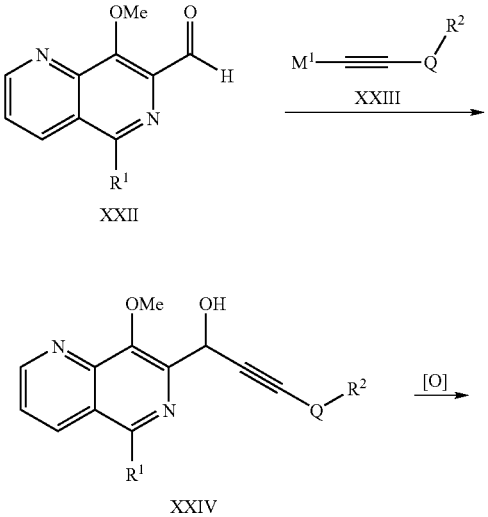

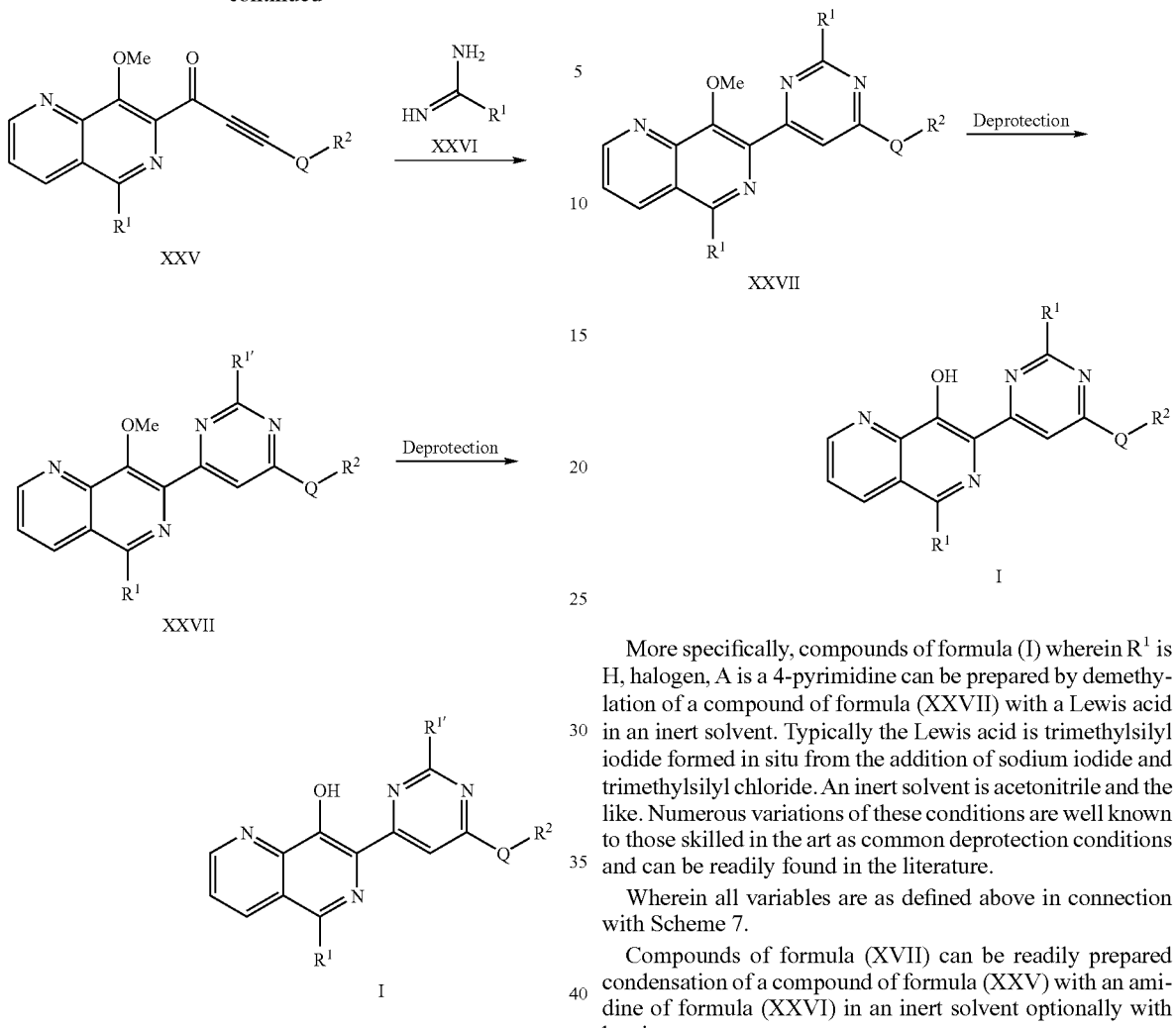

wherein R[1] is hydrogen, A is 4-pyrimidinyl, Q is $C_{1-3}$alkyl, —C(OR[4])—, or —CF$_2$ and all other substituents are as hereinbefore defined.

M[1] is lithium, or magnesium halide, cerium dihalide.

Generally, the process for preparing compounds of the formula (I) wherein R[1] is H, halogen, A is a 4-pyrimidine comprises the steps of:

a) Reduction of a compound of formula (XVI) to give a compound of formula (XXII);

b) Reaction of a compound of formula (XXII) with a compound of formula (XXIII) to give a compound of formula (XXIV);

c) Oxidation of a compound of formula (XXIV) to give a compound of formula (XXV);

d) Condensation of a compound of formula (XXV) with a compound of formula (XXVI) to give a compound of formula (XVII);

e) Demethylation of a compound of formula (XXVII) to give a compound of formula (I).

More specifically, compounds of formula (I) wherein R[1] is H, halogen, A is a 4-pyrimidine can be prepared by demethylation of a compound of formula (XXVII) with a Lewis acid in an inert solvent. Typically the Lewis acid is trimethylsilyl iodide formed in situ from the addition of sodium iodide and trimethylsilyl chloride. An inert solvent is acetonitrile and the like. Numerous variations of these conditions are well known to those skilled in the art as common deprotection conditions and can be readily found in the literature.

Wherein all variables are as defined above in connection with Scheme 7.

Compounds of formula (XVII) can be readily prepared condensation of a compound of formula (XXV) with an amidine of formula (XXVI) in an inert solvent optionally with heating.

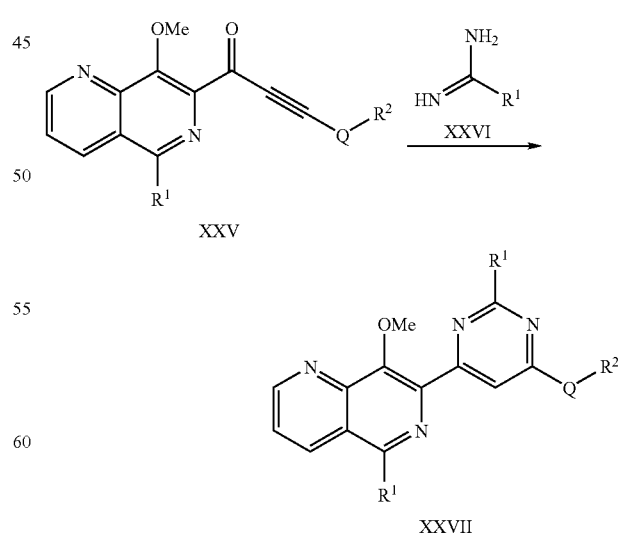

Wherein all variables are as defined above in connection with Scheme 7.

Typically this type of reaction is performed in a solvent such as the lower alcohols, 1-methylpyrrolidin-2-one, N,N-dimethylformamide, tetrahydrofuran and the like. Optionally a base may be added such as triethylamine, potassium t-butoxide, potassium carbonate and the like. The reaction may be heated to 50-150° C.

Compounds of formula (XXV) can readily be prepared by oxidation of a compound of formula (XXIV).

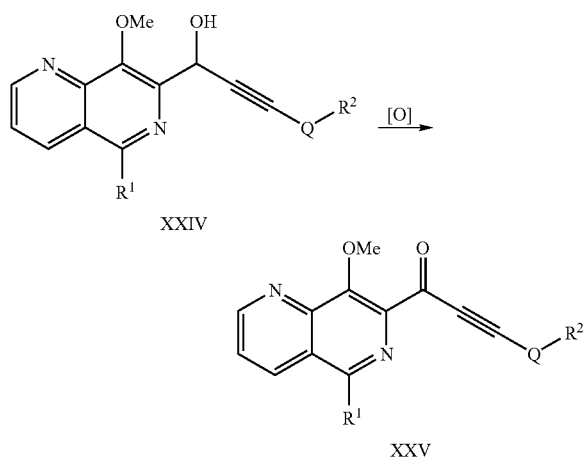

XXIV

XXV

Wherein all variables are as defined above in connection with Scheme 7.

Typical oxidants well known to one skilled in the art may be employed for this transformation. By way of example, suitable oxidants may include manganese dioxide, pyridinium chlorochromate and the like. Solvents include but are not limited to chloroform, dichloromethane and the like.

Compounds of formula (XXIV) may be prepared by reacting a compound of formula (XXII) with a compound of formula (XXIII) in an inert solvent at or below ambient temperature.

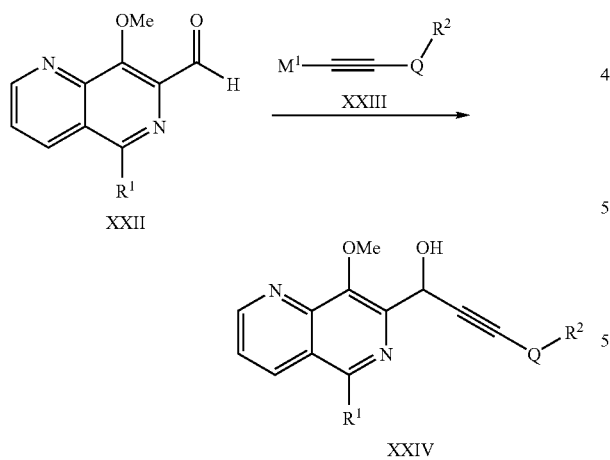

XXII

XXIV

Wherein all variables are as defined above in connection with Scheme 7.

More specifically, this type of reaction may be performed in a solvent such as tetrahydrofuran and the like at −78° C. to room temperature. Compounds of the formula (XXIII) may be prepared according to methods found in the literature or by treating a the corresponging terminal alkyne with a suitable base such as lithium diisopropyl amide or butyllithium and the like.

Compounds of the formula (XXII) may be readily prepared by treating a compound of formula with an appropriate reducing agent in an inert solvent, optionally at a low temperature.

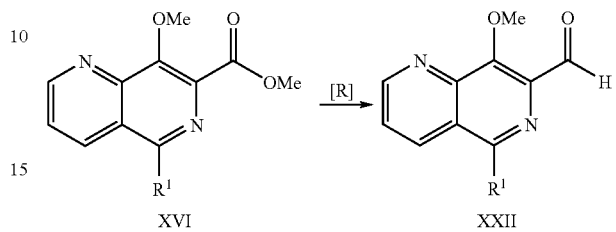

XVI

XXII

Wherein all variables are as defined above in connection with Scheme 7.

Reducing agents well known to those skilled in the art may be used. By way of example, reagents such as diisobutyl aluminum hydride and the like may be used. Solvents include but are not limited to hexanes, tetrahydrofuran, dichloromethane and the like. The reaction may optionally be carried out at temperatures of −78° C. to room temperature.

Compounds of the formula (XVI) can readily be prepared according to the methods described in the previous schemes.

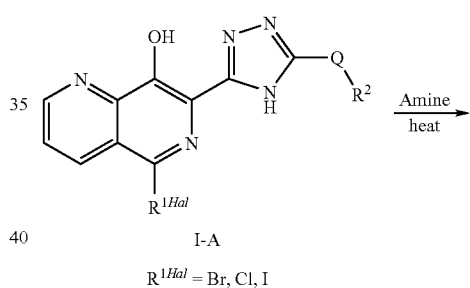

I-A $R^{1Hal} = Br, Cl, I$

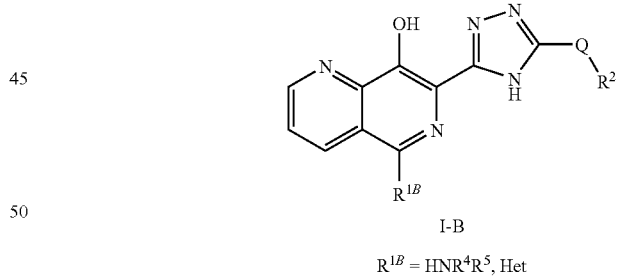

I-B $R^{1B} = HNR^4R^5$, Het

It will be apparent to those skilled in the art that compounds of formula (I) may be converted to other compounds of formula (I) using techniques well known in the art. By way of example one method of converting a compound of formula (I) to other compounds of formula (I) involves heating a compound of formula (I-A) wherein $R^1$ is a halogen with an amine of formula $HNR^4R^5$ or heterocycle to form a compound of formula (I-B).

More specifically, compounds of formula (I-A) can be converted to compounds of formula (I-B) by heating with suitably nucleophilic amine either neat or in an inert solvent. Inert solvents include but are not limited to the lower alcohols, 1-methylpyrrolidin-2-one, N,N-dimethylformamide, tetrahydrofuran, 1,4-dioxane and the like. Optionally a base such as potassium carbonate can be added Another particularly useful method of converting a compound of formula (I) to other compounds of formula (I) comprises reacting a compound of formula (I-C) with a halogenating reagent to give a compound of formula (I-D).

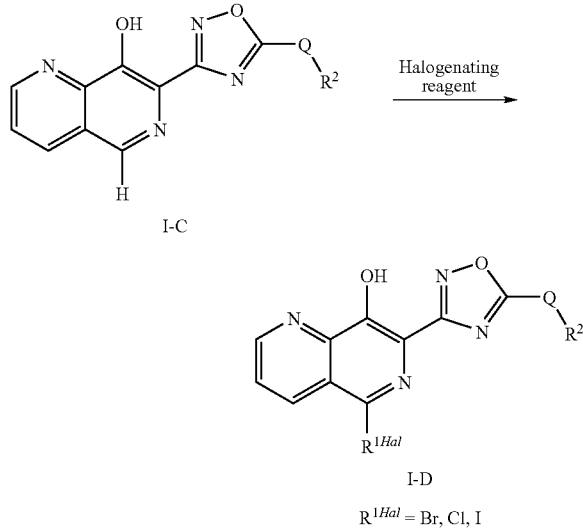

I-C

I-D $R^{1Hal}$ = Br, Cl, I

This procedure may be carried out by reacting a compound of formula (I-C) wherein $R^1$ is H with a halogenating reagent in an inert solvent. Several halogentating reagents are well known to those skilled in the art including but are not limited to N-bromosuccinimide, bromine, iodine, iodine monochloride, N-chlorosuccinimide, tetraalkylammonium tribromides and the like. Solvents include but are not limited to 1-methylpyrrolidin-2-one, N,N-dimethylformamide, tetrahydrofuran, dichloromethane, chloroform, acetic acid and the like.

In a similar manner as described for conversion of a compound of formula (I) to other compounds of formula (I), methyl ether protected precursors to compound of formula (I) are a particularly useful intermediate to convert to other precursors to compounds of formula (I). Several of the above methods described throughout the schemes can be applied to a compound of formula (XIX) and related compounds. By way of example, one method of converting a compound of formula (XIX) can to other compounds of the formula (XIX) comprises reacting a compound of formula (XIX-A) wherein $R^1$ is a halogen with an amine of formula $HNR^4R^5$ or heterocycle to form a compound of formula (XIX-B).

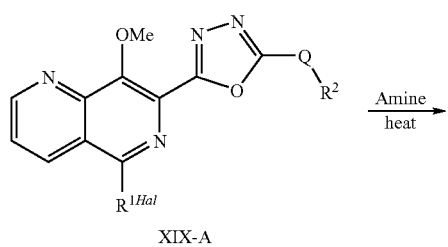

XIX-A

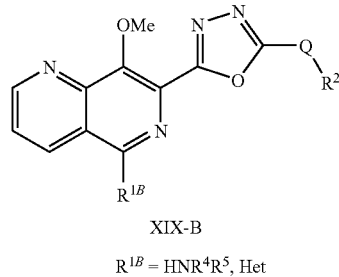

XIX-B $R^{1B}$ = $HNR^4R^5$, Het

This procedure may be carried out in an analogous manner to that described above by heating a compound of formula (XIX-A) with a nucleophilic amine either neat or in an inert solvent. Inert solvents include but are not limited to the lower alcohols, 1-methylpyrrolidin-2-one, N,N-dimethylformamide, tetrahydrofuran, 1,4-dioxane and the like. Optionally a base such as potassium carbonate can be added. As outlined in previous schemes, a compound of formula (XIX-B) can be converted to a compound of formula (I).

Another particularly useful method of converting a compound of formula (XIX) to other compounds of formula (XIX) involves reacting a compound of formula (XIX-A) with an amide, lactam, sulfonamide or sultam using conditions outlined in the literature (Buchwald et. al. *J. Am. Chem. Soc.* 2002, 124, 7421) involving a copper (I) catalyst, a base, ligand in an inert solvent or (Buchwald et. al. *J. Am. Chem. Soc.* 2002, 124, 6043) using a palladium catalyst, ligand in an inert solvent.

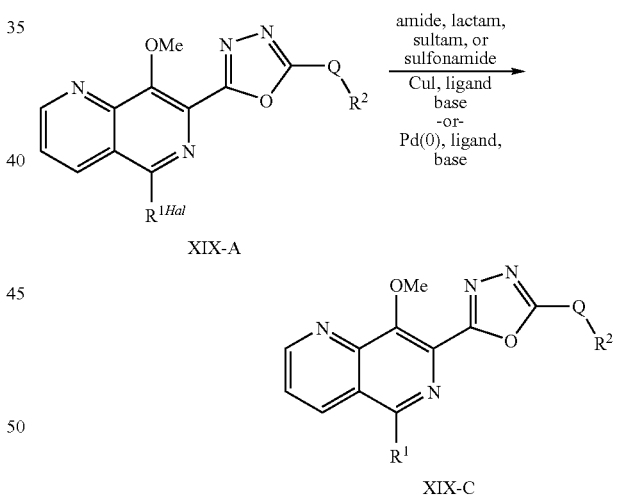

XIX-A

XIX-C

More specifically, a copper (I) source is copper (I) iodide. A suitable ligand is N,N'-dimethylethylenediamine and the like. Preferred bases include but are not limited to potassium carbonate, potassium phosphate, sodium bicarbonate and the like. An inert solvent of particular use is toluene. The copper and ligand are used in similar ratios at 2-10 mol percent. The reaction is typically heated to 70 to 100° C.

As will be apparent to those skilled in the art, the methods described herein are not comprehensive and additional methods exist in the literature or are commonly known to those skilled in the art to manipulate the appropriate intermediates to produce compounds of formula (I). It will also be apparent that the above methods and procedures in a synthetic campaign can be altered in their order and combined as will be obvious to one skilled in the art to produce compounds of formula (I).

In order that the invention described herein may be more fully understood, the following examples are set forth. It should be understood that these examples are for illustrative purposes only and are not to be construed as limiting this invention in any manner.

The following examples are intended for illustration only and are not intended to limit the scope of the invention in any way. Reagents are commercially available or are prepared according to procedures in the literature. $^1$H and $^{13}$C NMR spectra were obtained on Varian Unity Plus NMR spectrometers at 300 or 400 MHz, and 75 or 100 MHz respectively. $^{19}$F NMR were recorded at 282 MHz. Mass spectra were obtained on Micromass Platform, or ZMD mass spectrometers from Micromass Ltd. Altrincham, UK, using either Atmospheric Chemical Ionization (APCI) or Electrospray Ionization (ESI). Analytical thin layer chromatography was used to verify the purity of some intermediates which could not be isolated or which were too unstable for full characterization, and to follow the progress of reactions. Unless otherwise stated, this was done using silica gel (Merck Silica Gel 60 F254). Column or flash chromatography was used for the purification of some compounds. The methods employed used either Merck Silica gel 60 (230-400 mesh), and the stated solvent system under pressure or were automated using ISCO combiflash systems with commericially available pre-packed columns and a gradient elution protocol. Automated reverse phase preparative chromatographic separations were performed using either a medium pressure ISCO combiflash system or an Agilent 1100 preparative LC using a gradient eluent of acetonitrile/water/formic acid and a Waters symmetry C18 column. Microwave reactions were carried out using a Smith synthesizer from Personal Chemistry.

EXAMPLE 1

7-(5-Benzyl-4H-1,2,4-triazol-3-yl)-1,6naphthyridin-8-ol

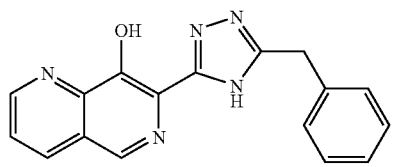

a) N-(Cyanomethyl)-4-methylbenzenesulfonamide. To a cold (0° C.) solution of aminoacetonitrile hydrochloride (1.0 g, 10.8 mmol) in pyridine (10 mL) was added p-toluenesulfonyl chloride (1.0 g, 5.2 mmol). The resultant mixture was stirred for 30 minutes at 0° C. Water was added to the cold reaction mixture. The solids were collected on a filter and washed with cold water. The solids were placed in a flask and azeotroped with methanol to give N-(cyanomethyl)-4-methylbenzenesulfonamide (1.03 g, 94%) as a white solid. $^1$H NMR (CDCl$_3$): δ 7.79 (d, J=8.4 Hz, 2 H), 7.37 (d, J=8.4 Hz, 2 H), 4.82 (broad, 1 H), 4.03 (d, J=6.8 Hz, 2 H), 2.46 (s, 3 H); MS m/z 233 (M+Na).

b) Isopropyl 3-({(cyanomethyl)[(4-methylphenyl)sulfonyl]amino}methyl)pyridine-2-carboxylate. To a cold (0° C.) solution of isopropyl 3-(hydroxymethyl)pyridine-2-carboxylate (928 mg, 4.8 mmol) (prepared according to P. Ornstein et. al. *J. Med. Chem.* 1989, 32, 827) in tetrahydrofuran (30 mL) was added N-(cyanomethyl)-4-methylbenzenesulfonamide (1.0 g, 4.8 mmol) and triphenylphosphine (1.27 g, 4.9 mmol). Diisopropyl azodicarboxylate (0.96 mL, 4.9 mmol) was added dropwise and the resultant solution was allowed to warm to room temperature. The mixture was stirred for 30 minutes and Celite was added and the solvents removed in vacuo. This material was purified by flash chromatography on silica gel (33% ethyl acetate-hexanes with gradient elution) to provide isopropyl 3-({(cyanomethyl)[(4-methylphenyl)sulfonyl]amino}methyl)pyridine-2-carboxylate (1.3 g, 71%) as a white solid. $^1$H NMR (CDCl$_3$): δ 8.70 (d, J=4.8 Hz, 1 H), 8.08 (d, J=8.1 Hz, 1 H), 7.79 (d, J=8.1 Hz, 2 H), 7.51 (dd, J=8.1, 4.8 Hz, 1 H), 7.41 (d, J=8.1 Hz, 2 H), 5.30 (m, 1 H), 4.75 (s, 2 H), 4.18 (s, 2 H), 2.48 (s, 3 H), 1.41 (d, J=6.3 Hz, 6 H); MS m/z 388 (M+1).

c) 8-Hydroxy-1,6-naphthyridine-7-carbonitrile. To a cold (0° C.) solution of 3-({(cyanomethyl)[(4-methylphenyl)sulfonyl]amino}methyl)pyridine-2-carboxylate (1.02 g, 2.63 mmol) in methanol (50 mL) and tetrahydrofuran (20 mL) was added sodium methoxide (1.42 mL, 4.62 M in methanol, 6.58 mmol). The mixture was stirred at 0° C. for 30 minutes and then room temperature for 30 minutes. The solvents were removed in vacuo and the residue was taken up in water. The solution was treated with 1 N HCl (aq) until the pH was neutral. The solids that formed were collected on a filter and washed with additional cold water. This material was azeotroped with methanol to provide 8-hydroxy-1,6-naphthyridine-7-carbonitrile (400 mg, 89%) as a white powder. $^1$H NMR (DMSO-d$_6$): δ 9.24 (dd, J=4.4, 1.6 Hz, 1 H), 8.94 (s, 1 H), 8.68 (dd, J=8.4, 1.6 Hz, 1 H), 7.93 (dd, J=8.4, 4.4 Hz, 1 H); MS m/z 170 (M−1).

d) 7-(5-Benzyl-4H-1,2,4-triazol-3-yl)-1,6-naphthyridin-8-ol. A solution of 8-hydroxy-1,6-naphthyridine-7-carbonitrile (31 mg, 0.18 mmol) and phenylacetic hydrazide (135 mg, 0.90 mmol) in dioxane (4 mL) and acetic acid (0.2 mL) was heated at 200° C. in a microwave chamber for 12 minutes. The solids were removed by filtration and the filtrate was concentrated. The residue was purified by preparative HPLC to provide the title compound (30 mg, 55%) as a yellow solid. $^1$H NMR (CDCl$_3$/CD$_3$OD): δ 9.06 (d, J=3.2 Hz, 1 H), 8.77 (s, 1 H), 8.26 (d, J=6.3 Hz, 1 H), 7.57 (dd, J=6.3, 3.2 Hz, 1 H), 7.33-7.17 (m, 5 H), 4.16 (s, 2 H); MS m/z 304 (M+1).

EXAMPLE 2

7-[5-(4-Fluorobenzyl)-4H-1,2,4-triazol-3-yl]-1,6-naphthyridin-8-ol

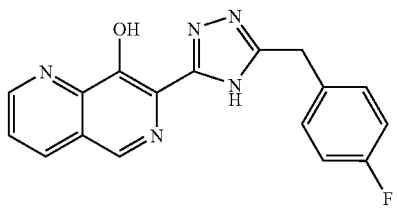

a) 2-(4-Fluorophenyl)acetic hydrazide. A cold (0° C.) solution of hydrazine (4.5 mL, 144 mmol) in dichloromethane (50 mL) was treated with a dichloromethane solution of (4-fluorophenyl)acetyl chloride (1.0 g, 5.8 mmol). The resultant solution was stirred for 40 minutes and water was then added. The layers were separated and the aqueous layer was extracted with dichloromethane and the combined organics were dried over sodium sulfate. Filtration and concentration followed by purification by flash chromatography (5% methanol-dichloromethane gradient elution) provided 2-(4-fluorophenyl)acetic hydrazide (673 mg, 69%) as a white solid. $^1$H NMR (DMSO-d$_6$): δ 9.18 (broad, 1 H), 7.26 (dd, J=8.4, 5.7 Hz, 2 H), 7.09 (t, J=8.4 Hz, 2 H), 4.21 (broad, 2 H), 3.31 (s, 2 H); MS m/z 169 (M+1).

b) 7-[5-(4-Fluorobenzyl)-4H-1,2,4-triazol-3-yl]-1,6-naphthyridin-8-ol. In a similar manner to that described in example 1 from of 8-hydroxy-1,6-naphthyridine-7-carbonitrile (30 mg, 0.18 mmol) and 2-(4-fluorophenyl)acetic hydrazide (147 mg, 0.90 mmol) was formed the title compound (9 mg, 16%) as a yellow solid. $^1$H NMR (CDCl$_3$/CD$_3$OD): δ 9.14 (m, 1 H), 8.80 (s, 1 H), 8.28 (m, 1 H), 7.61 (dd, J=8.4, 4.5 Hz, 1 H), 7.33 (dd, J=8.7, 5.7 Hz, 2 H), 6.99 (t, J=8.7 Hz, 2 H), 4.17 (s, 2 H); $^9$F NMR (CDCl$_3$/CD$_3$OD): δ –116.72; MS m/z 344 (M+Na).

EXAMPLE 3

7-(5-Benzyl-4H-1,2,4-triazol-3-yl)-5-(1,1-dioxido-1,2-thiazinan-2-yl)-1,6-naphthyridin-8-ol

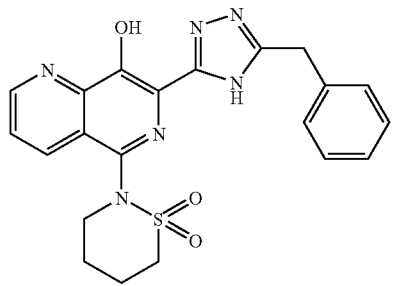

a) 5-Bromo-8-hydroxy-1,6-naphthyridine-7-carbonitrile. To a suspension of 8-hydroxy-1,6-naphthyridine-7-carbonitrile (5.0 g, 29.2 mmol) in dichloromethane (50 mL) was added N-bromosuccinimide (5.46 g, 30.6 mmol). The reaction mixture was refluxed for 3 hours. After cooling, the reaction mixture was quenched with sodium thiosulfate, then concentrated to remove excess dichloromethane. The crude residue was taken up in 1 N sodium hydroxide solution. The precipitated solids were collected on a filter and dried to provide 5-bromo-8-hydroxy[1,6]naphthyridine-7-carbonitrile sodium salt (7.54 g, 95%) as a yellow solid. $^1$H NMR (DMSO-d$_6$) δ 8.84 (dd, J=4.2, 1.5 Hz, 1 H), 8.26 (dd, J=8.5, 1.4 Hz, 1 H), 7.72 (dd, J=8.5, 4.3 Hz, 1 H); MS m/z 250 (M+1). This material could be used directly or converted by acidification with 1 N hydrochloric acid solution to the neutral title compound. $^1$H NMR (DMSO-d$_6$) δ 9.28 (d, J=3.2 Hz, 1H), 8.61 (d, J=8.4 Hz, 1 H), 8.03 (dd, J=8.5, 4.2 Hz, 1 H).

b) a) 5-(1,1-Dioxido-1,2-thiazinan-2-yl)-8-hydroxy-1,6naphthyridine-7-carbonitrile. To a 100 mL flask containing 5-bromo-8-hydroxy-1,6-naphthyridine-7-carbonitrile (0.50 g, 1.99 mmol) and 1,2-thiazinane 1,1-dioxide (0.41 g, 2.99 mmol) (White, E. H.; Lim, H. M. J. Org. Chem. 1987, 52, 2162) was added pyridine (10 mL) and Cu$_2$O (0.43 g, 2.99 mmol). The mixture was heated at 105° C. for 18 hours. The suspension was cooled to room temperature, chloroform and Celite were added and the mixture was filtered through Celite eluting with chloroform. The filtrate was diluted with a 0.255 M disodium EDTA solution (10 mL) and stirred 18 hours at room temperature. The layers were separated and the aqueous layer was extracted twice with chloroform. The combined organics were dried over sodium sulfate, filtered and concentrated in vacuo to yield 5-(1,1-dioxido-1,2-thiazinan-2-yl)-8-hydroxy-1,6-naphthyridine-7-carbonitrile complexed with copper (0.54 g, 73%) as a green solid. MS m/z 327 (M+Na). This material was routinely used without further purification or attempts to completely remove the copper residue. An analytical decomplexed sample was isolated after acidic reverse phase chromotographic purification for spectral characterization. $^1$H NMR (CDCl$_3$): δ 9.03 (m, 1 H), 8.63 (d, J=8.0 Hz, 1 H), 7.71 (dd, J=8.0, 4.0 Hz, 1 H), 4.08 (m, 1 H), 3.71 (m, 1 H), 3.43 (m, 1 H), 3.21 (m, 1 H), 2.53 (m, 1 H), 2.37 (m, 2 H), 1.68 (m, 1 H).

c) 7-(5-Benzyl-4H-1,2,4-triazol-3-yl)-5-(1,1-dioxido-1,2-thiazinan-2-yl)-1,6-naphthyridin-8-ol. A solution of 5-(1,1-dioxido-1,2-thiazinan-2-yl)-8-hydroxy-1,6-naphthyridine-7-carbonitrile (51 mg, 0.17 mmol) and phenylacetic hydrazide (75 mg, 0.50 mmol) in dioxane (4 mL) and acetic acid (0.2 mL) was heated at 200° C. in a microwave chamber for 12 minutes. The solids were removed by filtration and the filtrate was concentrated in vacuo. The residue was taken up in chloroform and stirred vigorously with a solution of 0.25 M ethylenediaminetetraacetic acid disodium salt for 1 hour to remove any residual copper from the previous step. The layers were separated and the organics were washed with brine and dried over sodium sulfate. Filtration and concentration followed by preparative HPLC purification provided the title compound (29 mg, 40%) as a white solid. $^1$H NMR (CDCl$_3$): δ 9.08 (m, 1 H), 8.59 (d, J=8.4 Hz, 1 H), 7.60 (dd, J=8.4, 4.0 Hz, 1 H), 7.36-7.15 (m, 5 H), 4.17 (s, 2 H), 3.93 (m, 1 H), 3.72 (m, 1 H), 3.43 (m, 1 H), 3.10 (m, 1 H), 2.26 (m, 2 H), 2.05 (m, 1 H), 1.58 (m, 1H); MS m/z 437 (M+1).

EXAMPLE 4

7-[5-(3-Chlorobenzyl)-4H-1,2,4-triazol-3-yl]-1,6-naphthyridin-4ol

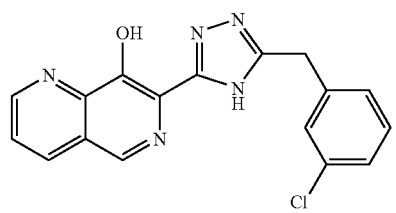

The title compound was prepared in a similar manner to that described in example 1 from of 8-hydroxy-1,6-naphthyridine-7-carbonitrile (48 mg, 0.28 mmol) and 2-(3-Chlorophenyl)acetic hydrazide (257 mg, 1.4 mmol) as a yellow solid (4 mg, 5%). $^1$H NMR (CDCl$_3$/CD$_3$OD): δ 9.08 (dd, J=4.0, 1.2 Hz, 1 H), 8.79 (s, 1 H), 8.27 (dd, J=8.0, 1.2 Hz, 1 H), 7.58 (dd, J=8.0, 4.0 Hz, 1 H), 7.31 (s, 1 H), 7.23-7.18 (m, 3 H), 4.15 (s, 2 H); MS m/z 338 (M+1).

EXAMPLE 5

7-[5-(3-Methoxybenzyl)-4H-1,2,4-triazol-3-yl]-1,6-naphthyridin-8-ol

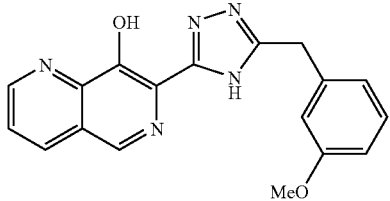

The title compound was prepared in a similar manner to that described in example 1 from of 8-hydroxy-1,6-naphthyridine-7-carbonitrile (50 mg, 0.29 mmol) and 2-(3-methoxyphenyl)acetic hydrazide (270 mg, 1.5 mmol) as a yellow solid (20 mg, 21%). $^1$H NMR (CDCl$_3$): δ 9.19 (m, 1 H), 8.91 (s, 1 H), 8.31 (d, J=7.6 Hz, 1 H), 7.63 (m, 1 H), 7.22 (m, 1 H), 7.01-6.97 (m, 2 H), 6.83-6.79 (m, 2 H), 4.23 (s, 2 H), 3.79 (s, 3 H); MS m/z 334 (M+1).

EXAMPLE 6

7-[5-(3,4-Dimethoxybenzyl)-4H-1,2,4-triazol-3-yl]-1,6-naphthyridin-8-ol

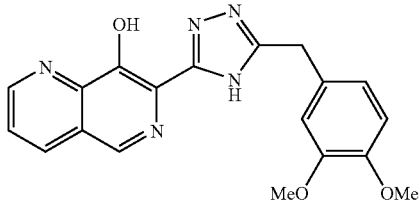

The title compound was prepared in a similar manner to that described in example 1 from of 8-hydroxy-1,6-naphthyridine-7-carbonitrile (50 mg, 0.29 mmol) and 2-(3,4-dimethoxyphenyl)acetic hydrazide (315 mg, 1.5 mmol) as a yellow solid (36 mg, 34%). $^1$H NMR (CDCl$_3$): δ 9.19 (m, 1 H), 8.93 (s, 1 H), 8.32 (d, J=8.4 Hz, 1 H), 7.63 (m, 1 H), 6.98-6.95 (m, 2 H), 6.82 (d, J=8.0 Hz, 1 H), 4.19 (s, 2 H), 3.88 (s, 3 H), 3.85 (s, 3 H); MS m/z 364 (M+1).

EXAMPLE 7

1-[7-(5-Benzyl-4H-1,2,4-triazol-3-yl)-8-hydroxy-1,6-naphthyridin-5-yl]pyrrolidin-2-one

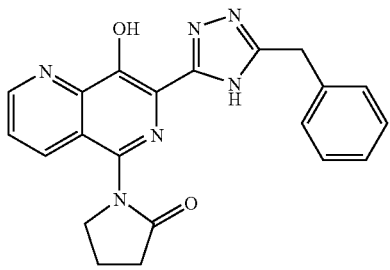

a) 8-(benzyloxy)-5-bromo[1,6]naphthyridine-7-carbonitrile. To a suspension of 5-bromo-8-hydroxy[1,6]naphthyridine-7-carbonitrile sodium salt (2.5 g, 9.19 mmol) in N,N-dimethylformamide was added cesium carbonate (2.99 g, 9.19 mmol) and benzyl bromide (1.09 mL, 9.19 mmol). The reaction mixture was stirred 16 hours at room temperature, then heated to 60° C. for two hours. Additional cesium carbonate (500 mg, 1.53 mmol) and benzyl bromide (500 μL, 4.20 mmol) were added and stirred at 60° C. for 16 hours. The reaction mixture was cooled and diluted with water and ethyl acetate. The organic layer was washed with water and brine, then dried over sodium sulfate. Filtation and concentration followed by flash chromatography (3:2 hexanes:ethyl acetate) provided 8-(benzyloxy)-5-bromo[1,6]naphthyridine-7-carbonitrile (1.05 g, 34%) as a white solid. $^1$H NMR (CDCl$_3$) δ 9.25 (dd, J=4.2, 1.6 Hz, 1 H), 8.62 (dd, J=8.6, 1.6 Hz, 1 H), 7.80 (dd, J=8.7, 4.3 Hz, 1 H), 7.52 (dd, J=7.8, 1.9 Hz, 2 H), 7.55-7.50 (m, 3H), 5.92 (s, 2 H); MS m/z 340 (M+1).

b) 8-(Benzyloxy)-5-(2-oxopyrrolidin-1-yl)-1,6-naphthyridine-7-carbonitrile. According to the procedure of Buchwald et. al. (*J. Am. Chem. Soc.* 2002, 124, 7421) a solution of 8-(benzyloxy)-5-bromo-1,6-naphthyridine-7-carbonitrile (114 mg, 0.34 mmol) in toluene (5 mL) was treated successively with pyrrolidinone (0.04 mL, 0.44 mmol), potassium phosphate (142 mg, 0.67 mmol), copper (I) iodide (3 mg, 0.02 mmol), and N,N'-dimethylethylenediamine (0.004 mL, 0.04 mmol). The mixture was heated at 80° C. for 6 hours. The reaction mixture was cooled to room temperature and chloroform was added. The solids were removed by filtration through Celite and the filtrate was concentrated and purified by flash chromatography on silica gel (2% methanol in dichloromethane, gradient elution) to provide 8-(benzyloxy)-5-(2-oxopyrrolidin-1-yl)-1,6-naphthyridine-7-carbonitrile (61 mg, 53%) as a white solid. $^1$H NMR (CDCl$_3$): δ 9.18 (dd, J=4.0, 1.6 Hz, 1 H), 8.34 (dd, J=8.8, 1.6 Hz, 1 H), 7.64 (dd, J=8.8, 4.4 Hz, 1 H), 7.55 (m, 2 H), 7.39-7.32 (m, 3 H), 5.84 (s, 2 H), 4.13 (t, J=7.2 Hz, 2 H), 2.68 (t, J=8.0 Hz, 2 H), 2.29 (m, 2 H); MS m/z 345 (M+1).

c) 8-Hydroxy-5-(2-oxopyrrolidin-1-yl)-1,6-naphthyridine-7-carbonitrile. A suspension of 8-(benzyloxy)-5-(2-oxopyrrolidin-1-yl)-1,6-naphthyridine-7-carbonitrile (61 mg, 0.18 mmol) and Pd/C (61 mg, 10 wt %) in ethyl acetate was stirred vigorously under an atmosphere of hydrogen (1 atm) for 8 hours. The suspension was filtered through a pad of Celite and the filtrate concentrated to give 8-hydroxy-5-(2-oxopyrrolidin-1-yl)-1,6-naphthyridine-7-carbonitrile (31 mg, 69%) as a yellow solid. $^1$H NMR (CD$_3$OD/CDCl$_3$): δ 9.05 (m, 1 H), 8.25 (d, J=8.4 Hz, 1 H), 7.67 (dd, J=8.4, 4.0 Hz, 1 H), 4.08 (t, J=7.2 Hz, 2 H), 2.66 (t, J=8.0 Hz, 2 H), 3.21 (m, 2 H); MS m/z 255 (M+1).

d) 1-[7-(5-Benzyl-4H-1,2,4-triazol-3-yl)-8-hydroxy-1,6-naphthyridin-5-yl]pyrrolidin-2-one. The title compound was prepared in a similar manner to that described in example 1 from of 8-hydroxy-5-(2-oxopyrrolidin-1-yl)-1,6-naphthyridine-7-carbonitrile (17 mg, 0.06 mmol) and phenylacetic hydrazide (50 mg, 0.33 mmol) as a white solid (7 mg, 28%). $^1$H NMR (CD$_3$OD/CDCl$_3$): δ 9.05 (d, J=3.6 Hz, 1 H), 8.32 (d, J=8.4 Hz, 1 H), 7.66 (m, 1 H), 7.35-7.19 (m, 5 H), 4.22-4.19 (m, 4 H), 2.70 (t, J=8.0 Hz, 2 H), 2.35 (m, 2 H); MS m/z 387 (M+1).

EXAMPLE 8

1-{7-[5-(4-Fluorobenzyl)-4H-1,2,4-triazol-3-yl]-8-hydroxy-1,6-naphthyridin-5-yl}pyrrolidin-2-one

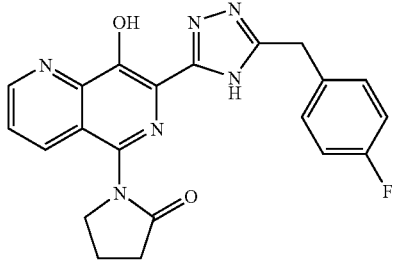

The title compound was prepared in a similar manner to that described in example 7 to give a yellow solid. $^1$H NMR (CDCl$_3$): δ 9.16 (d, J=3.2 Hz, 1 H), 8.27 (d, J=8.4 Hz, 1 H), 7.61 (dd, J=8.4, 4.0 Hz, 1 H), 7.36 (dd, J=8.4, 5.6 Hz, 2 H), 7.02 (t, J=8.4 Hz, 2 H), 4.19 (s, 2 H), 4.14 (t, J=6.8Hz, 2 H), 2.73 (t, J=8.0 Hz, 2 H), 2.36 (m, 2 H); MS m/z 405 (M+1).

EXAMPLE 9

1-{7-[5-(4-Fluorobenzyl)-4H-1,2,4-triazol-3-yl]-8-hydroxy-1,6-naphthyridin-5-yl}piperidin-2-one

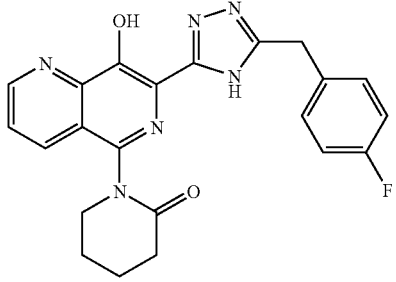

The title compound was prepared in a similar manner to that described in example 7 to give a yellow solid. $^1$H NMR (CDCl$_3$): δ 9.15 (d, J=9.15 Hz, 1 H), 8.08 (d, J=8.4 Hz, 1 H), 7.60 (dd, J=8.4, 4.0 Hz, 1 H), 7.33 (dd, J=8.4, 5.6 Hz, 2 H), 7.00 (t, J=8.4 Hz, 2 H), 4.16 (s, 2 H), 4.11 (m, 1 H), 3.50 (m, 1 H), 2.68 (m, 2 H), 2.08 (m, 4 H); MS m/z 419 (M+1).

EXAMPLE 10

7-(5-Benzyl-4H-1,2,4-triazol-3-yl)-5-bromo-1,6-naphthyridin-8-ol

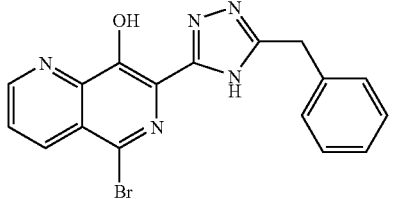

The title compound was prepared in a similar manner to that described in example 1 from 5-bromo-8-hydroxy-1,6-naphthyridine-7-carbonitrile (100 mg, 0.40 mmol) and phenylacetic hydrazide (120 mg, 0.80 mmol) to give a yellow solid (102 mg, 67%). $^1$H NMR (CDCl$_3$/CD$_3$OD): δ 9.03 (d, J=2.8 Hz, 1 H), 8.46 (d, J=8.0 Hz, 1 H), 7.62 (dd, J=8.4, 4.0 Hz, 1 H), 7.28-7.16 (m, 5 H), 4.12 (s, 2 H); MS m/z 382 (M+1).

EXAMPLE 11

7-(5-Benzyl-1,2,4-oxadiazol-3-yl)-1,6-naphthyridin-8ol

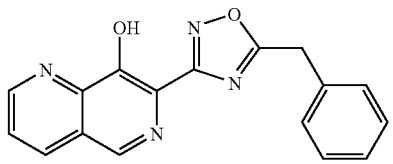

a) N',8-Dihydroxy[1,6]naphthyridine-7-carboximidamide. To a suspension of 8-hydroxy[1,6]naphthyridine-7-carbonitrile (1.0 g, 5.85 mmol) in ethanol (20 mL) was added hydroxylamine hydrochloride (2.0 g, 29.3 mmol) and potassium carbonate (8.1 g, 58.5 mmol). The reaction mixture was refluxed for 1.5 hours. The reaction mixture was cooled and diluted with water (80 mL). The resultant mixture was concentrated in vacuo to remove excess ethanol. The solids which had precipitated were collected on a filter to provide N',8-dihydroxy[1,6]naphthyridine-7-carboximidamide (988 mg, 82%) as a yellow solid. $^1$H NMR (DMSO-d$_6$): δ 13.10 (broad, 1H), 10.30 (broad, 1H), 9.08 (d, J=4.2 Hz, 1H), 8.87, (s, 1H), 8.53 (d, J=8.4 Hz, 1H), 7.71 (dd, J=8.4, 4.2 Hz, 1H), 6.58 (broad, 1H); MS m/z 205 (M+1).

b) 7-(5-Benzyl-1,2,4-oxadiazol-3-yl)-1,6-naphthyridin-8-ol. A mixture of N',8-dihydroxy[1,6]naphthyridine-7-carboximidamide (23 mg, 0.11 mmol) and phenyl acetylchloride (0.044 mL, 0.33 mmol) in dioxane (1.5 mL) were heated at 190° C. in a microwave chamber for 10 minutes. The reaction mixture was concentrated in vacuo and purifield by medium pressure reverse phase liquid chromatography (5% acetonitrile/95% water with 0.1% TFA gradient to 100% acetonitrile) to provide 7-(5-benzyl-1,2,4-oxadiazol-3-yl)-1,6-naphthyridin-8-ol (2 mg, 6%) as a yellow solid. $^1$H NMR (CDCl$_3$): δ 9.18 (m, 1 H), 8.99 (s, 1 H), 8.34 (d, J=8.4 Hz, 1 H), 7.67 (dd, J=8.4, 4.0 Hz, 1 H), 7.43-7.32 (m, 5 H), 4.43 (s, 2 H); MS m/z 305 (M+1).

EXAMPLE 12

5-(1,1-Dioxido-1,2-thiazinan-2-yl)-7-[5-(4-fluorobenzyl)-4H-1,2,4-triazol-3-yl]-1,6-naphthyridin-8-ol

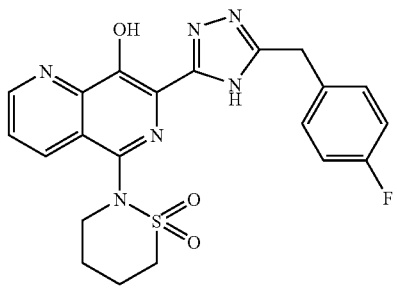

The title compound was prepared in a similar manner to that described in example 3 from 5-(1,1-dioxido-1,2-thiazinan-2-yl)-8-hydroxy-1,6-naphthyridine-7-carbonitrile (12 mg, 0.04 mmol) and 2-(4-fluorophenyl)acetic hydrazide (33 mg, 0.20 mmol) to give a white solid (6 mg, 31%). $^1$H NMR (CDCl$_3$/CD$_3$OD): δ 9.13 (m, 1 H), 8.56 (d, J=8.4 Hz, 1 H), 7.63 (dd, J=8.4, 4.0 Hz, 1 H), 7.32 (dd, J=8.4, 5.6 Hz, 2 H), 6.99 (t, J=8.4 Hz, 2 H), 4.17 (s, 2 H), 3.90 (m, 1 H), 3.77 (m, 1 H), 3.52 (m, 1 H), 3.32 (m, 1 H), 2.44-1.89 (m, 4 H); $^{19}$F NMR (CDCl$_3$/CD$_3$OD): δ −116.86; MS m/z 455 (M+1).

EXAMPLE 13

7-[5-(4-Chlorobenzyl)-4H-1,2,4-triazol-3-yl]-5-(1,1-dioxido-1,2-thiazinan-2-yl)-1,6-naphthyridin-8-ol

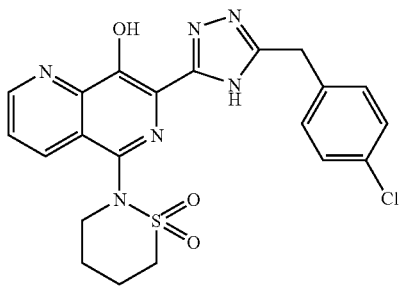

The title compound was prepared in a similar manner to that described in example 3 from 5-(1,1-dioxido-1,2-thiazinan-2-yl)-8-hydroxy-1,6-naphthyridine-7-carbonitrile (75 mg, 0.24 mmol) and 2-(4-chlorophenyl)acetic hydrazide (137 mg, 0.74 mmol) to give a white solid (49 mg, 43%). $^1$H NMR (CDCl$_3$/CD$_3$OD): δ 9.06 (d, J=3.6 Hz, 1 H), 8.62 (d, J=8.4 Hz, 1 H), 7.66 (dd, J=8.4, 4.0 Hz, 1 H), 7.28-7.21 (m, 4 H), 4.15 (s, 2 H), 3.89 (m, 1 H), 3.82 (m, 1 H), 3.63 (m, 1 H), 3.31 (m, 1 H), 2.41 (m, 3 H), 1.79 (m, 1 H); MS m/z 471 (M+1).

EXAMPLE 14

5-Bromo-7-[5-(4-fluorobenzyl)-4H-1,2,4-triazol-3-yl]-1,6-naphthyridin-8-ol

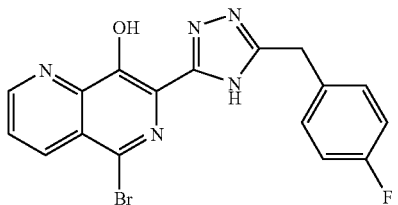

A suspension of 5-bromo-8-hydroxy-1,6-naphthyridine-7-carbonitrile (0.25 g, 9.99 mmol), 2-(4-fluorophenyl)acetic hydrazide (0.34 g, 2 mmol), 1,4-dioxane (2 mL) and acetic acid was heated at 200° C. for 10 minutes in a microwave chamber. The mixture was allowed to cool to room temperature, the precipitate was filtered and washed with dichloromethane. The filtrate was concentrated in vacuo, 1 N sodium hydroxide and ethyl acetate were added and the aqueous layer was washed with ethyl acetate. The aqueous layer was then acidified to pH 5 and the solids formed were collected. This material was azeotroped with methanol to provide 5-bromo-7-[5-(4-fluorobenzyl)-4H-1,2,4-triazol-3-yl]-1,6-naphthyridin-8-ol (0.17 g, 42%) as a yellow solid. $^1$H NMR (CDCl$_3$/CD$_3$OD): δ 9.07 (dd, J=4.0, 1.2 Hz, 1 H), 8.50 (dd, J=8.4, 1.2 Hz, 1 H), 7.65 (dd, J=8.4, 4.0 Hz, 1 H), 7.26 (m, 2 H), 6.95 (m, 2 H), 4.11 (s, 2 H); MS m/z 400 (M+1).

EXAMPLE 15

7-[5-(4-Fluorobenzyl)-4H-1,2,4-triazol-3-yl]-5-(methylsulfonyl)-1,6-naphthyridin-8-ol

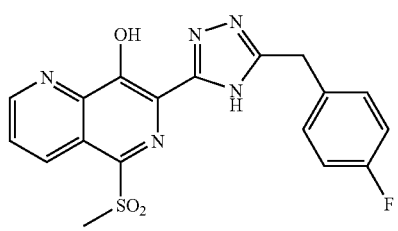

A solution of 5-bromo-7-[5-(4-fluorobenzyl)-4H-1,2,4-triazol-3-yl]-1,6-naphthyridin-8-ol (9 mg, 0.02 mmol) and sodium methanesulfinic acid (100 mg) in 1-methylpyrrolidin-2-one (2 mL) was heated at 150° C. for 3 hours. The resultant solution was cooled to room temperature and water was added. The solids which formed were removed by filtration and further purified by preparative HPLC to give 7-[5-(4-fluorobenzyl)-4H-1,2,4-triazol-3-yl]-5-(methylsulfonyl)-1,6-naphthyridin-8-ol (3 mg, 33%) as a white solid. $^1$H NMR (CDCl$_3$): δ 9.32 (d, J=8.4 Hz, 1 H), 9.25 (d, J=4.4 Hz, 1 H), 7.75 (dd, J=8.4, 4.4 Hz, 1 H), 7.36 (dd, J=8.4, 5.6 Hz, 2 H), 7.03 (t, J=8.4 Hz, 2 H). 4.24 (s, 2 H), 3.42 (s, 3 H); MS m/z 400 (M+1).

EXAMPLE 16

7-[5-(4-Fluorobenzyl)-4H-1,2,4-triazol-3-yl]-5-(4-methylpiperazin-1-yl)-1,6-naphthyridin-8-ol

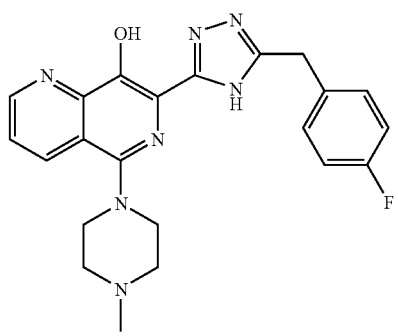

A solution of 5-bromo-7-[5-(4-fluorobenzyl)-4H-1,2,4-triazol-3-yl]-1,6-naphthyridin-8-ol (12 mg, 0.03 mmol) in neat N-methylpiperazine was heated in a sealed tube at 150° C. for 16 hours. The excess amine was removed in vacuo and the residue purified by preparative HPLC to provide the formate salt of the title compound (6 mg, 50%) as a white solid. $^1$H NMR (CDCl$_3$): δ 9.13 (dd, J=4.0, 1.6 Hz, 1 H), 8.40 (s, 1 H formate), 8.36 (dd, J=8.4, 1.6 Hz, 1 H), 7.55 (dd, J=8.4, 4.0

Hz, 1 H), 7.34 (dd, J=8.4, 5.6 Hz, 2 H), 7.98 (t, J=8.4 Hz, 2 H), 4.17 (s, 2 H), 3.55 (m, 4 H), 3.21 (m, 4 H), 2.73 (s, 3 H); MS m/z 420 (M+1).

EXAMPLE 17

7-[5-(4-Fluorobenzyl)-4H-1,2,4-triazol-3-yl]-5-morpholin-4-yl-1,6-naphthyridin-8-ol

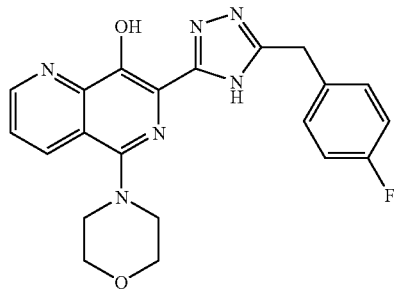

A solution of 5-bromo-7-[5-(4-fluorobenzyl)-4H-1,2,4-triazol-3-yl]-1,6-naphthyridin-8-ol (34 mg, 0.09 mmol) in neat morpholine was heated in a sealed tube at 150° C. for 16 hours. The excess amine was removed in vacuo and the residue purified by preparative HPLC to provide the title compound (19 mg, 55%) as a white solid. $^1$H NMR (CDCl$_3$): δ 9.14 (dd, J=4.4, 1.6 Hz, 1 H), 8.45 (dd, J=8.4, 1.6 Hz, 1 H), 7.57 (dd, J=8.4, 4.4 Hz, 1 H), 7.36 (dd, J=8.4, 5.2 Hz, 2 H), 7.01 (t, J=8.4 Hz, 2 H), 4.19 (s, 2 H), 3.98 (t, J=4.4 Hz, 4 H), 3.33 (t, J=4.4 Hz, 4 H); $^{13}$C NMR (CDCl$_3$): δ 168.49, 161.79 (d, J$_{CF}$=243.6 Hz), 154.85, 153.95, 153.40, 146.07, 144.75, 133.88, 132.99 (d, J$_{CF}$=3.0 Hz), 130.40 (d, J$_{CF}$=130.4 Hz), 122.67, 120.81, 119.70, 115.37 (d, J$_{CF}$=21.2 Hz), 66.88, 52.06, 33.71; MS m/z 407 (M+1).

EXAMPLE 18

4-{7-[5-(4-Fluorobenzyl)-4H-1,2,4-triazol-3-yl]-8-hydroxy-1,6-naphthyridin-5-yl}piperazin-2-one

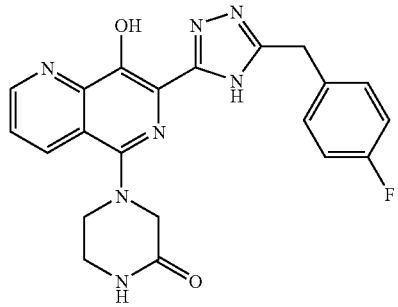

A solution of 5-bromo-7-[5-(4-fluorobenzyl)-4H-1,2,4-triazol-3-yl)-1,6-naphthyridin-8-ol (10 mg, 0.03 mmol) and piperazin-2-one (60 mg, 0.60 mmol) in 1-methylpyrrolidin-2-one (2 mL) was heated at 150° C. for 18 hours. The resultant solution was cooled to room temperature and water was added. The solids which formed were removed by filtration and further purified by prep HPLC to give 4-{7-[5-(4-Fluorobenzyl)-4H-1,2,4-triazol-3-yl]-8-hydroxy-1,6-naphthyridin-5-yl}piperazin-2-one (7 mg, 67%) as a white solid. $^1$H NMR (CD$_3$OD/CDCl$_3$): δ 9.03 (d, J=4.4 Hz, 1 H), 8.48 (d, J=8.4 Hz, 1 H), 7.64 (dd, J=8.4, 4.4 Hz, 1 H), 7.32 (dd, J=8.4, 5.6Hz, 2 H), 6.97 (t, J=8.4Hz, 2 H). 4.13 (s, 2 H), 4.10 (5,2 H), 3.60 (m, 2 H), 3.42 (m, 2 H); $^{19}$F NMR (CD$_3$OD/CDCl$_3$): δ −117.93; MS m/z 420 (M+1).

EXAMPLE 19

7-(5-Benzyl-1,3,4-oxadiazol-2-yl)-1,6-naphthyridin-8-ol

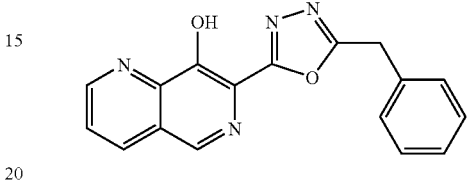

a) Methyl 8-hydroxy-1,6-naphthyridine-7-carboxylate. An analogous procedure to that described in example 3 was used to combine isopropyl 3-(hydroxymethyl)pyridine-2-carboxylate (25 g, 128 mmol) and methyl N-[(4-methylphenyl)sulfonyl]glycinate (31.5 g, 128 mmol) to provide methyl 8-hydroxy-1,6-naphthyridine-7-carboxylate (14.1 g, 55%) as a white solid. $^1$H NMR (CDCl$_3$): δ 11.78 (s, 1 H), 9.21 (dd, J=4.0, 1.6 Hz, 1 H),8.32 (dd, J=8.4, 1.6 Hz, 1 H), 7.71 (dd, J=8.4,4.0 Hz, 1 H), 4.13 (s, 3 H); MS m/z 205 (M+1).

b) 8-Hydroxy-1,6-naphthyridine-7-carboxylic acid. A solution of methyl 8-hydroxy-1,6-naphthyridine-7-carboxylate (204 mg, 1.0 mmol) in methanol was treated with lithium hydroxide (3 mL, 1 M aqueous, 3 mmol) and then heated at 90° C. for 18 h. The resulting suspension was concentrated in vacuo and the residue taken up in a minimal amount of water. The solution was neutralized by the addition of HCl (3 mL, 1 N, 3 mmol) resulting in the formation of a white precipitate. This material was removed by filtration and azeotroped 3 times with methanol to provide 8-hydroxy-1,6-naphthyridine-7-carboxylic acid (165 mg, 87%) as a white solid. $^1$H NMR (DMSO-d$_6$): δ 9.25 (dd, J=4.2, 1.5 Hz, 1 H), 8.73 (dd, J=8.1, 1.5 Hz, 1 H), 7.91 (dd, J=8.1, 4.2 Hz, 1 H); MS m/z 420 (M+1).

c) 7-(5-Benzyl-1,3,4-oxadiazol-2-yl)-1,6-naphthyridin-8-ol. To a solution of 8-hydroxy-1,6-naphthyridine-7-carboxylic acid (37 mg, 0.19 mmol) in dichloromethane (3 mL) was added phenylacetic hydrazide (29 mg, 0.19 mmol), 1-(3-dimethylaminopropyl)-3-ethylcarbodiimide hydrochloride (EDCI) (45 mg, 0.23 mmol), and 1-hydroxybenzotriazole (2 mg, 0.01 mmol). The resultant solution was stirred at room temperature 18 hours. Water was added along with excess dichlromethane. The organic layer was washed with brine and the aqueous layer was extracted several times with dichloromethane. The combined organics were dried and concentrated. This material was taken up in phosphorous oxychloride (3 mL) and heated at 105° C. for 45 minutes. The mixture was cooled to room temperature and concentrated in vacuo. Methanol was added to the residue and then concentrated. This material was again dissolved in methanol and treated with sodium methoxide (0.5 mL, 0.5 M in methanol) for 1 hour. The mixture was neutralized by the addition of acetic acid and concentrated. The residue was purified by preparative HPLC to give the title compound as a white solid. $^1$H NMR (CDCl$_3$): δ 9.22 (d, J=4.2 Hz, 1 H), 8.93 (s, 1 H), 8.34 (d, J=8.4 Hz, 1 H), 7.69 (dd, J=8.4, 4.2 Hz, 1 H), 7.43-7.30 (m, 5 H), 4.39 (s, 2 H); MS m/z 305 (M+1).

EXAMPLE 20

7-[5-4-Fluorobenzyl)-1,3,4oxadiazol-2-yl]-1,6-naphthyridin-8-ol

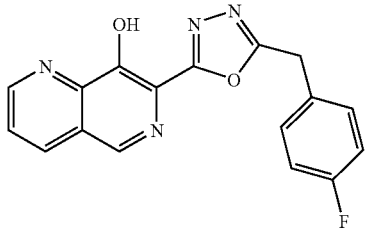

a) 8-Hydroxy-1,6-naphthyridine-7-carbohydrazide. A solution of methyl 8-hydroxy-1,6-naphthyridine-7-carboxylate (590 mg, 2.9 mmol) and hydrazine (1 mL, 32 mmol) in ethanol (30 mL) was heated at reflux for 2.5 hours. The resultant suspension was cooled to room temperature and concentrated in vacuo. The residue was taken up in water and 1 N HCl (aq) was added until a precipitate formed. This material was collected on a filter and azeotroped with methanol to provide 8-hydroxy-1,6-naphthyridine-7-carbohydrazide (411 mg, 70%) as a solid. $^1$H NMR (DMSO-$d_6$): δ 9.15 (d, J=4.2 Hz, 1 H), 8.60 (d, J=8.4 Hz, 1 H), 7.82 (dd, J=8.4, 4.2 Hz, 1 H); MS m/z 205 (M+1).

b) 7-[5-(4-Fluorobenzyl)-1,3,4-oxadiazol-2-yl]-1,6-naphthyridin-8-ol. To a cold (0° C.) solution of 8-hydroxy-1,6-naphthyridine-7-carbohydrazide (54 mg, 0.26 mmol) in pyridine (5 mL) was added 2-(4-fluorophenyl)acetyl chloride (0.36 mL of a 0.86 M stock solution in dichloromethane, 0.31 mmol). The resultant solution was stirred at room temperature for 6 hours at which time another equivalent of 2-(4-fluorophenyl)acetyl chloride stock solution was added. After 18 hours, the reaction mixture was concentrated in vacuo and the residue was treated with phosphorous oxychloride. This solution was heated at 105° C. for 3 hours and worked up in a similar manner as was described in example 19 to give the title compound (6 mg, 8%) as a yellow solid. $^1$H NMR (CDCl$_3$): δ 9.22 (d, J=4.0 Hz, 1 H), 8.93 (s, 1 H), 8.34 (d, J=8.4 Hz, 1 H), 7.69 (dd, J=8.4, 4.0 Hz, 1 H), 7.39 (dd, J=8.4, 5.6 Hz, 2 H), 7.05 (t, J=8.4 Hz, 2 H), 4.36 (s, 2 H); MS m/z 323 (M+1).

EXAMPLE 21

5-(1,1-Dioxido-1,2-thiazinan-2-yl)-7-[5-(4-fluorobenzyl)-1,3,4-oxadiazol-2-yl]-1,6-naphthyridin-8-ol

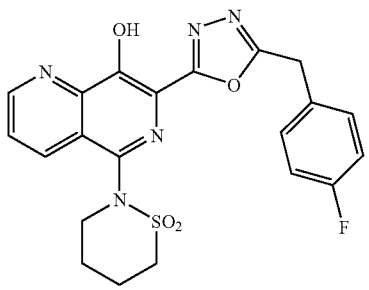

a) Methyl 5-bromo-8-hydroxy-1,6-naphthyridine-7-carboxylate. An analogous procedure to that described in example 3 was used to brominate methyl 8-hydroxy-1,6-naphthyridine-7-carboxylate (5.0 g, 24.5 mmol) with N-bromosuccinimide (4.36 g, 24.5 mmol) to form methyl 5-bromo-8-hydroxy-1,6-naphthyridine-7-carboxylate (4.38 g, 63%) as a white solid. $^1$H NMR (DMSO-$d_6$): δ 11.53 (broad, 1 H), 9.25 (dd, J=4.2, 1.2 Hz, 1 H), 8.58 (dd, J=8.4, 1.2 Hz, 1 H), 7.99 (dd, J=8.4, 4.2 Hz, 1 H), 3.94 (s, 3 H); MS m/z 305 (M+Na).

b) Methyl 5-bromo-8-{[(4-methylphenyl)sulfonyl]oxy}-1,6-naphthyridine-7-carboxylate. To a suspension of methyl 5-bromo-8-hydroxy-1,6-naphthyridine-7-carboxylate (874 mg, 3.08 mmol) in chloroform (10 mL) was added triethylamine (0.64 mL, 4.62 mmol) and p-toluenesulfonyl chloride (708 mg, 3.71 mmol). The solution was heated at 50° C. for 3 hours. The mixture was cooled to room temperature and saturated aqueous sodium bicarbonate was added. The organic layer was washed with brine. The aqueous layer was extracted with chloroform and the combined organics were dried over sodium sulfate. Filtration and concentration followed by flash chromatography (25% ethyl acetate in hexanes, gradient elution) provided methyl 5-bromo-8-{[(4-methylphenyl)sulfonyl]oxy}-1,6-naphthyridine-7-carboxylate (626 mg, 47%) as a white solid. $^1$H NMR (DMSO-$d_6$): 9.03 (dd, J=4.4, 1.6 Hz, 1 H), 8.64 (dd, J=8.4, 1.6 Hz, 1 H), 7.93 (dd, J=8.4, 4.4 Hz, 1 H), 7.71 (d, J=8.4 Hz, 2 H), 7.41 (d, J=8.4 Hz, 2 H), 3.77 (s, 3 H), 2.42 (s, 3 H); MS m/z 459 (M+Na).

c) Methyl 5-(1,1-dioxido-1,2-thiazinan-2-yl)-8-{[(4-methylphenyl)sulfonyl]oxy}-1,6-naphthyridine-7-carboxylate. To a solution of methyl 5-bromo-8-{[(4-methylphenyl)sulfonyl]oxy}-1,6-naphthyridine-7-carboxylate (626 mg, 1.44 mmol) in N,N,-dimethylformamide (10 mL) was added 1,2-thiazinane 1,1-dioxide (234 mg, 1.73 mmol), copper (I) oxide (247 mg, 1.73 mmol), and 2,2'-bipyridine (270, 1.73 mmol). The resultant suspension was heated at 125° C. for 6 hours. Another round of all the above reagents was again added and the mixture heated for 18 hours. The resultant mixture was cooled to room temperature and Celite was added. The solids were filtered through a pad of Celite and the filtrate was treated with excess disodium EDTA solution and stirred vigorously for 3 hours. The layers were separated and the aqueous layer was extracted twice with dichloromethane and the combined organics were dried over sodium sulfate. Filtration and concentration followed by flash chromatography (dichloromethane to 10% methanol in dichloromethane) provided methyl 5-(1,1-dioxido-1,2-thiazinan-2-yl)-8-{[(4-methylphenyl)sulfonyl]oxy}-1,6-naphthyridine-7-carboxylate as a solid. $^1$H NMR (CDCl$_3$): δ 8.89 (dd, J=4.4, 1.6 Hz, 1 H), 8.63 (dd, J=8.4, 1.6 Hz, 1 H), 7.83 (d, J=8.4 Hz, 2 H), 7.58 (dd, J=8.4, 4.4 Hz, 1 H), 7.30 (d, J=8.4 Hz, 2 H), 3.89 (s, 3 H), 4.20-1.60 (m, 8 H); MS m/z 492 (M+1).

d) 5-(1,1-Dioxido-1,2-thiazinan-2-yl)-8-hydroxy-1,6-naphthyridine-7-carbohydrazide. A solution of methyl 5-(1,1-dioxido-1,2-thiazinan-2-yl)-8-{[(4-methylphenyl)sulfonyl]oxy}-1,6-naphthyridine-7-carboxylate (250 mg, 0.5 mmol) and hydrazine (2 mL, 64 mmol) in ethanol (20 mL) was heated at 50° C. for 20 minutes. The resultant solution was cooled to room temperature and concentrated in vacuo. The residue was purified by preparative HPLC to give the formate salt of 5-(1,1-dioxido-1,2-thiazinan-2-yl)-8-hydroxy-1,6-naphthyridine-7-carbohydrazide (44 mg, 26%) as a white solid. $^1$H NMR (CDCl$_3$): δ 9.09 (d, J=4.4 Hz, 1 H), 8.57 (d, J=8.4 Hz, 1 H), 7.99 (s, 1 H formate), 7.67 (dd, J=8.4, 4.4 Hz, 1 H), 7.07 (broad, 1 H), 3.88-1.75 (m, 8 H); MS m/z 205 (M+1).

e) 5-(1,1-Dioxido-1,2-thiazinan-2-yl)-7-[5-(4-fluorobenzyl)-1,3,4-oxadiazol-2-yl]-1,6-naphthyridin-8-ol. The tide compound was prepared in a similar manner to example 21 from 5-(1,1-dioxido-1,2-thiazinan-2-yl)-8-hydroxy-1,6-naphthyridine-7-carbohydrazide (44 mg, 0.11 mmol) and 2-(4-fluorophenyl)acetyl chloride to provide 5-(1,1-dioxido-1,2-thiazinan-2-yl)-7-[5-(4-fluorobenzyl)-1,3,4-oxadiazol-2-yl]-1,6-naphthyridin-8-ol (7 mg, 15%) as a white solid. $^1$H NMR (CDCl$_3$): δ 9.19 (d, J=4.4 Hz, 1 H), 8.67 (d, J=8.4 Hz, 1 H), 7.71 (dd, J=8.4, 4.4 Hz, 1 H), 7.39 (dd, J=8.4, 5.6 Hz, 2 H), 7.08 (t, J=8.4 Hz, 2 H), 4.36 (s, 2 H), 4.18 (m, 1 H), 3.76 (m, 1 H), 3.54 (m, 1 H), 3.27 (m, 1 H), 2.53 (m, 2 H), 2.39 (m, 1 H), 1.69 (m, 1 H); MS m/z 478 (M+Na).

EXAMPLE 22

7-(5-Benzyl-4-H-1,2,4-triazol-3-yl)-5-(1-pyrrolidinyl)[1,6]naphthyridin-8-ol

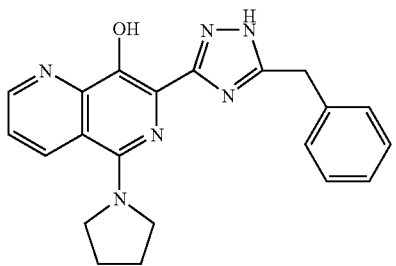

a) 8-(Benzyloxy)-5-(1-pyrrolidinyl)[1,6]naphthyridine-7-carbonitrile. To a solution of 8-(benzyloxy)-5-bromo[1,6]naphthyridine-7-carbonitrile (56 mg, 0.165 mmol) in toluene (2 mL) was added pyrrolidine (41 μL, 0.495 mmol), 2,2'-bis(diphenylphosphino)-1,1'-binaphthyl (31 mg, 0.0495 mmol), cesium carbonate (81 mg, 0.248 mmol), and palladium acetate (7 mg, 0.033 mmol). The reaction mixture was heated at 80° C. for 2 hours. The reaction mixture was cooled and diluted with ethyl acetate. The organic layer was washed with water and brine, then dried over sodium sulfate. Filtration and concentration, followed by flash chromatography provided 8-(benzyloxy)-5-(1-pyrrolidinyl)[1,6]naphthyridine-7-carbonitrile (34 mg, 63%) as a white solid. $^1$H NMR (CDCl$_3$) δ 9.05 (dd, J=4.0, 1.6 Hz, 1 H), 8.54 (dd, J=8.4, 1.2 Hz, 1 H), 7.59 (d, J=6.8 Hz, 2H), 7.47 (dd, J=8.8, 4.4 Hz, 1 H), 7.39-7.32 (m, 3 H), 5.49 (s, 2H), 3.77 (t, J=6.4 Hz, 4 H), 2.01 (m, 4 H); MS m/z 331 (M+1).

b) 8-Hydroxy-5-(1-pyrrolidinyl)[1,6]naphthyridine-7-carbonitrile. To a solution of 8-(benzyloxy)-5-(1-pyrrolidinyl)[1,6]naphthyridine-7-carbonitrile (123 mg, 0.373 mmol) in ethyl acetate (10 mL) was added 10% palladium on carbon (85 mg). The reaction mixture was stirred under a hydrogen balloon for 16 hours. The reaction mixture was filtered through celite and rinsed with ethyl acetate. Concentration followed by flash chromatography (2% to 3% methanol in dichloromethane) provided 8-hydroxy-5-(1-pyrrolidinyl)[1,6]naphthyridine-7-carbonitrile (37 mg, 41%) as a green oil. $^1$H NMR (CDCl$_3$) δ 8.93 (d, J=4.0 Hz, 1 H), 8.59 (d, J=8.4 Hz, 1H), 7.54 (dd, J=8.4,4.0 Hz, 1 H), 3.75 (t, J=6.4 Hz, 4 H), 2.01 (m, 4H); MS m/z 241 (M+1).

c) 7-(5-Benzyl-1H-1,2,4-triazol-3-yl)-5-(1-pyrrolidinyl)[1,6]naphthyridin-8-ol. To a suspension of 8-(benzyloxy)-5-1-pyrrolidinyl)[1,6]naphthyridine-7-carbonitrile (37 mg, 0.154 mmol) in dioxane (2.5 mL) was added phenylacetic hydrazide (104 mg, 0.770 mmol). The reaction vessel was sealed and heated at 200° C. in a microwave chamber for 20 minutes. Additional phenylacetic hydrazide (104 mg, 0.770 mmol) was added and the reaction mixture was microwaved at 200° C. for 20 minutes. The reaction mixture was filtered through celite and rinsed with dichloromethane. The combined filtrate was concentrated and purified by preparative HPLC. The isolated material was dissolved in 1 N sodium hydroxide solution and washed with dichloromethane. The basic layer was acidified with 1 N hydrochloric acid solution, then extracted with ethyl acetate. The concentrated organic layer was dissolved in dichloromethane and 1 N hydrogen chloride was added. Precipitated solid was separated from mother liquor. Solid was partitioned between ethyl acetate and saturated sodium bicarbonate solution. Organic layer was separated and washed with water and brine, then dried over sodium sulfate. Filtration and concentration provided 7-(5-benzyl-1H-1,2,4-triazol-3-yl)-5-(1-pyrrolidinyl)[1,6]naphthyridin-8-ol (5 mg, 9%) as a yellow solid. $^1$H NMR (CDCl$_3$) δ 11.00 (br, 1H), 9.01 (d, J=3.6 Hz, 1H), 8.53 (d, J=7.6 Hz, 1 H), 7.45-7.20 (m, 6 H), 4.20 (s, 2 H), 3.75 (br, 4 H), 2.02 (br, 4 H); MS m/z 373 (M+1).

EXAMPLE 23

7-[5-(4-Fluorobenzyl)-1,2,4-oxadiazol-3-yl][1,6]naphthyridin-8-ol

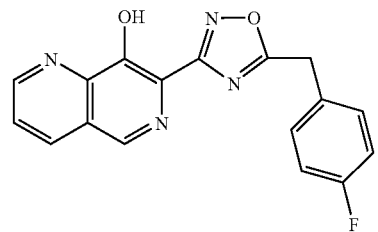

To a suspension of N',8-dihydroxy[1,6]naphthyridine-7-carboximidamide (50 mg, 0.244 mmol) in dioxane (3 mL) was added 4-fluorophenylacetyl chloride (40 μL, 0.293 mmol). The reaction vessel was sealed and heated at 160° C. in a microwave chamber for 10 minutes. The solids were collected on a filter, then triturated with methano/ether to provide 7-[5-(4-fluorobenzyl)-1,2,4-oxadiazol-3-yl][1,6]naphthyridin-8-ol hydrochloride (13 mg, 15%) as an orange solid. $^1$H NMR (CD$_3$OD) δ 9.43 (d, J=4 Hz, 1H), 9.34 (s, 1H), 9.05 (d, J=8.0 Hz, 1H), 8.14 (dd, J=8.4, 4.8 Hz, 1H), 7.48 (dd, J=8.4, 5.2 Hz, 2H), 7.12 (t, J=8.8 Hz, 2H), 4.92 (s, 2 H); MS m/z 323 (M+1).

EXAMPLE 24

1-{7-[5-(4-Fluorobenzyl-1,2,4-oxadiazol-3-yl]-8-hydroxyl[1,6]naphthyridin-5-yl]-2-pyrrolidinone

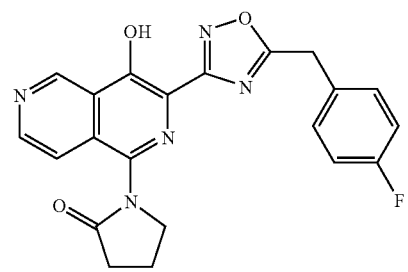

a) 7-[5-(4-Fluorobenzyl)-1,2,4-oxadiazol-3-yl][1,6]naphthyridin-8-ol. To a suspension of N',8-dihydroxy[1,6]naphthyridine-7-carboximidamide (231 mg, 1.13 mmol) in dioxane (5 mL) was added 4-fluorophenylacetyl chloride (185 µL, 1.35 mmol). The reaction vessel was sealed and heated at 155° C. in a microwave chamber for 10 minutes. The solids were collected on a filter. The solids were taken up in methanol (30 mL) and water (20 mL). 1N aqueous sodium hydroxide solution was added until the solution was neutral. The solids were collected on a filter to provide 7-[5-(4-fluorobenzyl)-1,2,4-oxadiazol-3-yl][1,6]naphthyridin-8-ol (140 mg, 39%) as a pale yellow solid. $^1$H NMR (DMSO-$d_6$): δ 8.71 (s, 1H), 8.22 (d, J=8.0 Hz, 1 H), 8.06 (s, 1H), 7.48 (dd, J=7.2, 4.0 Hz, 1H), 7.41 (t, J=6.4 Hz, 2H), 7.17 (t, J=8.4 Hz, 2H), 4.34 (s, 2H); MS m/z 323 (M+1).

b) 5-Bromo-7-[5-(4-fluorobenzyl)-1,2,4-oxadiazol-3-yl][1,6]naphthyridin-8-ol. To a cold (0° C.) solution of 7-[5-(4-fluorobenzyl)-1,2,4-oxadiazol-3-yl][1,6]naphthyridin-8-ol (26 mg, 0.0807 mmol) in N,N-dimethylformamide (400 µL) was added sodium bicarbonate (8 mg, 0.0968 mmol). A solution of n-bromosuccinimide (14 mg, 0.0807 mmol) in N,N-dimethylformamide (600 µL) was added dropwise and the reaction mixture was stirred at 0° C. for one hour. The reaction mixture was quenched with saturated aqueous sodium thiosulfate solution, then diluted with water. The solids were collected on a filter to provide 5-bromo-7-[5-(4-fluorobenzyl)-1,2,4-oxadiazol-3-yl][1,6]naphthyridin-8-ol (20 mg, 63%) as a yellow solid. $^1$H NMR (DMSO-$d_6$): δ 8.80 (d, J=3.2 Hz, 1H), 8.24 (d, J=8.4 Hz, 1H), 7.64 (dd, J=8.0, 4.0 Hz, 1H), 7.44 (dd, J=8.4, 5.6 Hz, 2H), 7.21 (t, J=8.8 Hz, 2H), 4.38 (s, 2H); MS m/z 401 (M+1).

c) 5-Bromo-7-[5-(4-fluorobenzyl)-1,2,4-oxadiazol-3-yl][1,6]naphthyridin-8-yl 4-methylbenzenesulfonate. To a suspension of 5-bromo-7-[5-(4-fluorobenzyl)-1,2,4-oxadiazol-3-yl][1,6]naphthyridin-8-ol (168 mg, 0.419 mmol) in chloroform (8 mL) was added triethylamine (88 µL, 0.726 mmol) and p-toluenesulfonyl chloride (96 mg, 0.504 mmol). The reaction mixture was stirred at room temperature, then diluted with water and chloroform. The organic layer was washed with water and brine, then dried over sodium sulfate. Filtration and concentration provided 5-bromo-7-[5-(4-fluorobenzyl)-1,2,4-oxadiazol-3-yl][1,6]naphthyridin-8-yl 4-methylbenzenesulfonate (170 mg, 73%) as a white solid. $^1$H NMR (CDCl$_3$) δ 9.09 (dd, J=4.4, 1.6 Hz, 1H), 8.61 (dd, J=8.8, 1.6 Hz, 1H), 7.73-7.70 (m,3H), 7.35 (dd, J=8.4, 5.2 Hz, 2H), 7.17 (d, J=8 Hz, 2H), 7.06 (t, J=8.4 Hz, 2H), 4.23 (s, 2H), 2.40 (s, 3H); MS m/z 555 (M+1).

d) 7-[5-(4-Fluorobenzyl)-1,2,4-oxadiazol-3-yl]-5-(2-oxo-1-pyrrolidinyl)[1,6]naphthyridin-8-yl 4-methylbenzenesulfonate. To a solution of 5-bromo-7-[5-(4-fluorobenzyl)-1,2,4-oxadiazol-3-yl][1,6]naphthyridin-8-yl 4-methylbenzenesulfonate (48 mg, 0.0866 mmol) in toluene (5 mL) was added pyrrolidinone (66 µL, 0.866 mmol) and potassium phosphate (37 mg, 0.173 mmol). In a separate flask, a stock solution of catalyst was prepared by adding N,N'-dimethylene diamine (93 µL, 0.866 mmol) to a stirring suspension of copper (I) iodide (165 mg, 0.866 mmol) in toluene (15 mL). To the original solution was added 150 µL stock solution and the reaction mixture was stirred at 90° C. for 30 minutes. Five addititional aliquots of 150 µL stock solution were added every 30 minutes. The reaction mixture was cooled and diluted with ethyl acetate. The resultant mixture was washed with water and brine, then dried over sodium sulfate. Filtration and concentration followed purification by flash chromatography (1% to 5% methanol-dichloromethane gradient elution) provided 7-[5-(4-fluorobenzyl)-1,2,4-oxadiazol-3-yl]-5-(2-oxo-1-pyrrolidinyl)[1,6]naphthyridin-8-yl 4-methylbenzenesulfonate (15 mg, 31%) as a white solid. $^1$H NMR (CDCl$_3$) δ 8.99 (dd, J=4.2, 1.5 Hz, 1 H), 8.60 (dd, J=8.7, 1.5 Hz, 1 H), 7.74 (d, 8.4 Hz, 2H), 7.56 (dd, 8.7, 4.2 Hz, 1H), 7.38 (dd, 8.7, 5.4 Hz, 2 H), 7.19 (d, 8.1 Hz, 2H), 7.07 (t, J=8.7 Hz, 2 H), 4.29-4.24 (m, 4 H), 2.71 (t, J=8.1 Hz, 2H), 2.42 (s, 3 H) 2.33 (m, 2 H); MS m/z 560 (M+1).

e) 1-{7-[5-(4-Fluorobenzyl)-1,2,4-oxadiazol-3-yl]-8-hydroxy[1,6]naphthyridin-5-yl}-2-pyrrolidinone. To a cold (0° C.) solution of 7-[5-(4-fluorobenzyl)-1,2,4-oxadiazol-3-yl]-5-(2-oxo-1-pyrrolidinyl)([1,6]naphthyridin-8-yl 4-methylbenzenesulfonate (15 mg, 0.0268 mmol) in methanol (2 mL) was added sodium methoxide (64 µL, 0.5 M in methanol, 0.0322 mmol). The reaction mixture was stirred 16 hours at 4° C., then quenched with water and concentrated in vacuo. The crude material was purified by preparative HPLC to provide 1-{7-[5-(4-fluorobenzyl)-1,2,4-oxadiazol-3-yl]-8-hydroxy[1,6]naphthyridin-5-yl}-2-pyrrolidinone (1 mg, 10%) as a white solid. $^1$H NMR (CDCl$_3$) δ 9.15 (dd, J=4.5, 1.8 Hz, 1 H), 8.35 (dd, J=8.4, 1.5 Hz, 1 H), 7.65 (dd, J=8.4, 4.2 Hz, 1 H), 7.38 (dd, J=8.7, 5.4 Hz, 2 H), 7.09 (t, J=8.7 Hz, 2 Hz), 4.41 (s, 2H), 4.24 (t, J=7.2 Hz, 2H), 2.71 (t, J=8.1, 2H), 2.35 (m, 2 H).

EXAMPLE 25

1-[7-(5-Benzyl-1,3,4-oxadiazol-2-yl)-8-hydroxy[1,6]naphthyridin-5-yl]-2-pyrrolidinone

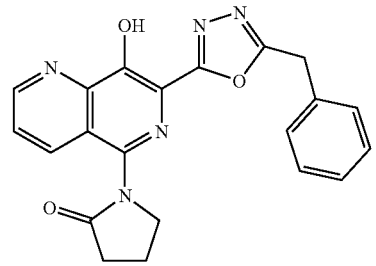

a) Methyl 5-bromo-8-methoxy[1,6]naphthyridine-7-carboxylate. To a suspension of methyl 5-bromo-8-hydroxy[1,6]naphthyridine-7-carboxylate (1.01 g, 3.57 mmol) in N,N-dimethylformamide (15 mL) was added cesium carbonate (2.32 g, 7.14 mmol). The resultant mixture was stirred for 30 minutes upon which time a bright yellow paste was formed. To this stirring paste was added iodomethane (666 µL, 10.7 mmol) and the resulting mixture was stirred 16 hours at room temperature. The reaction was quenched with ice water, then diluted with ethyl acetate. The organic layer was washed with water and brine, then dried over sodium sulfate. Filtration and concentration, followed by flash chromatography (20% to 50% ethyl acetate in hexanes) provided methyl 5-bromo-8-methoxy[1,6]naphthyridine-7-carboxylate (696 mg, 66%) as a white solid. $^1$H NMR (CDCl$_3$) δ 9.20 (dd, J=4.4, 1.6 Hz, 1 H), 8.61 (dd, J=8.4, 1.6 Hz, 1 H), 7.73 (dd, J=8.4, 4.0 Hz, 1H), 4.30 (s, 3 H), 4.04 (s, 3 H); MS m/z 297 (M+1).

b) 5-Bromo-8-methoxy[1,6]naphthyridine-7-carboxylic acid. To a solution of methyl 5-bromo-8-methoxy[1,6]naphthyridine-7-carboxylate (696 mg, 2.34 mmol) in, tetrahydrofuran (30 mL) was added lithium hydroxide solution (7 mL, 1.0 M in water, 7.03 mmol). The reaction mixture was stirred two hours at room temperature, then concentrated in vacuo. The resultant material was diluted with water and acidified with 1 N hydrochloric acid solution. The solids were collected on a filter to provide 5-bromo-8-methoxy[1,6]naphthyridine-7-carboxylic acid (284 mg, 43%) as a yellow solid.

$^1$H NMR (CDCl$_3$) δ 9.17 (dd, J=4.3, 1.6 Hz, 1H), 8.60 (dd, J=8.6, 1.6. Hz, 1 H), 7.73 (dd, J=8.6, 4.3 Hz, 1 H), 4.26 (s, 3 H); MS m/z 283 (M+1).

c) 5-Bromo-8-methoxy-N'-(phenylacetyl)[1,6]naphthyridine-7-carbohydrazide. To a solution of 5-bromo-8-methoxy [1,6]naphthyridine-7-carboxylic acid (284 mg, 1.00 mmol) in dichloromethane (25 mL) was added phenylacetic hydrazide (137 mg, 1.00 mmol), 1-hydroxybenzotriazole hydrate (4 mg, 0.0301 mmol), and 1-[3-(dimethylamino)propyl]-3-ethylcarbodiimide hydrochloride (212 mg, 1.10 mmol). The reaction mixture was stirred at room temperature for 3 hours, during which time a large amount of white solids formed. The reaction mixture was then partitioned between water and dichloromethane (a large excess of dichloromethane was needed to solubilize product). The organic layer was washed with water and brine, then dried over sodium sulfate. Filtration and concentration, followed by flash chromatography (0% to 10% methanol in dichloromethane) to provide 5-bromo-8-methoxy-N-(phenylacetyl)[1,6]naphthyridine-7-carbohydrazide (328 mg, 79%) as a white solid. $^1$H NMR (DMSO-d$_6$) δ 10.50 (d, J=1.6 Hz, 1H), 10.44 (d, J=1.6 Hz, 1 H), 9.27 (dd, J=4.0, 1.6 Hz, 1H), 8.63 (dd, J=8.8, 1.6 Hz, 1H), 7.94 (dd, J=8.8, 4.0 Hz, 1H), 7.36-7.26 (m, 5 H), 4.16 (s, 3H), 3.57 (s, 2 H); MS m/z 415 (M+1).

d) 7-(5-Benzyl-1,3,4-oxadiazol-2-yl)-5-bromo[1,6]naphthyridin-8-yl methyl ether. To a solution of 5-bromo-8-methoxy-N'-(phenylacetyl)[1,6]naphthyridine-7-carbohydrazide (1.96 g, 4.72 mmol), triphenylphosphine (1.48 g, 5.66 mmol), and triethylamine (1.97 mL, 14.2 mmol) in dichloromethane (100 mL) was added a solution of iodine (1.44 g, 5.66 mmol) in dichloromethane (50 mL) via addition funnel over 25 minutes. The reaction mixture was stirred an additional 15 minutes, then partitioned between dichloromethane and water. The organic layer was washed with water and brine, then dried over sodium sulfate. Filtration and concentration, followed by flash chromatography (30% to 60% ethyl acetate in hexanes) provided a material which was recrystallized from ethyl acetate to provide 7-(5-benzyl-1,3,4-oxadiazol-2-yl)-5-bromo[1,6]naphthyridin-8-yl methyl ether (1.50 g, 80%) as a white solid. $^1$H NMR (CDCl$_3$) δ 9.26 (m, 1 H), 8.70 (m, 1H), 7.80 (m, 1H), 7.52-7.34 (m, 5 H), 4.42 (s, 2 H), 4.36 (s, 3 H); MS m/z 397 (M+1).

e) 1-[7-(5-Benzyl-1,3,4-oxadiazol-2-yl)-8-methoxy[1,6] naphthyridin-5-yl]-2-pyrrolidinone. To a solution of 7-(5-benzyl-1,3,4-oxadiazol-2-yl)-5-bromo[1,6]naphthyridin-8-yl methyl ether (54 mg, 0.136 mmol) in toluene (3 mL) was added pyrrolidinone (103 μL, 0.1.36 mmol) and potassium phosphate (58 mg, 0.272 mmol). In a separate flask, a stock solution of catalyst was prepared by adding N,N'-dimethylene diamine (145 μL, 1.36 mmol) to a stirring suspension of copper (I) iodide (259 mg, 1.36 mmol) in toluene (10 mL). To the original solution was added 100 μL stock solution and the reaction mixture was stirred at 80° C. for 10 minutes. Five addititional aliquots of 100 μL stock solution were added every 30 minutes. The reaction mixture was cooled and diluted with ethyl acetate. The resultant mixture was washed with sodium bicarbonate solution and water. The organic layer was washed with brine, then dried over sodium sulfate. Filtration and concentration, followed by flash chromatography (1% to 5% methanol in dichloromethane) providedl-[7-(5-benzyl-1,3,4-oxadiazol-2-yl)-8-methoxy[1,6]naphthyridin-5-yl]-2-pyrrolidinone (10 mg, 18%) as a white solid. $^1$H NMR (CDCl$_3$) δ 9.21 (dd, J=4.2, 1.2 Hz, 1 H), 8.39 (dd, J=8.7, 1.8 Hz, 1 H), 7.65 (dd, J=8.4, 4.2 Hz, 1 H), 7.45-7.31 (m, 5 H), 4.43 (s, 2 H), 4.41-4.25 (m, 5 H), 2.75 (t, J=8.1 Hz,2 H),2.38 (m,2 H); MS m/z 402 (M+1).

f) 1-[7-(5-Benzyl-1,3,4-oxadiazol-2-yl)-8-hydroxy[1,6] naphthyridin-5-yl]-2-pyrrolidinone. To a solution of 1-[7-(5-benzyl-1,3,4-oxadiazol-2-yl)-8-methoxy[1,6]naphthyridin-5-yl]-2-pyrrolidinone (10 mg, 0.0249 mmol) in acetonitrile (500 μL) was added sodium iodide (30 mg 0.199 mmol). To this stirring solution was added trimethylsilyl chloride (25 μL, 0.199 mmol) dropwise and the reaction mixture was stirred at room temperature for 1.5 hours. The reaction mixture was quenched with 10% aqueous sodium bisulfite solution. The resultant mixture was concentrated in vacuo to remove the excess acetonitrile then partitioned between sodium bicarbonate solution and ethyl acetate. The organic layer was washed with water and brine, then dried over sodium sulfate. Filtration and concentration, followed by preparative HPLC purification provided 1-[7-(5-benzyl-1,3,4-oxadiazol-2-yl)-8-hydroxy[1,6]naphthyridin-5-yl]-2-pyrrolidinone (5 mg, 52%) as a pale green solid.

$^1$H NMR (CDCl$_3$) δ 9.24 (d, J=4 Hz, 1 H), 8.36 (d, J=8.6 Hz, 1 H), 7.69 (dd, J=8.5, 4.3 Hz, 1 H), 7.45-7.35 (m, 5 H), 4.43 (s, 2 H), 4.22 (t, J=6.8 Hz, 2 H), 2.76 (t, J=7.8 Hz, 2 Hz), 2.41 (m, 2 H); MS m/z 388 (M+1).

EXAMPLE 26

4-[7-(5-Benzyl-1,3,4-oxadiazol-2-yl)-8-hydroxy[1,6] naphthyridin-5-yl]-2-piperazinone

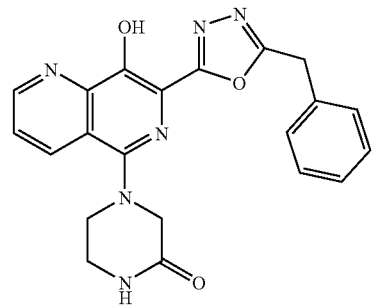

a) 4-[7-(5-Benzyl-1,3,4-oxadiazol-2-yl)-8-methoxy[1,6] naphthyridin-5-yl]-2-piperazinone. To a solution of 7-(5-benzyl-1,3,4-oxadiazol-2-yl)-5-bromo[1,6]naphthyridin-8-yl methyl ether (50 mg, 0.126 mmol) in dioxane (200 μL) was added piperazinone (126 mg, 1.26 mmol). The reaction mixture was heated in a sealed tube at 110° C. for 6 hours. Concentration followed by flash chromatography (1% to 5% methanol in dichloromethane) provided 4-[7-(5-benzyl-1,3, 4-oxadiazol-2-yl)-8-methoxy[1,6]naphthyridin-5-yl]-2-piperazinone (44 mg, 52%) as a yellow solid. $^1$H NMR (CDCl$_3$) δ 9.19 (d, J=4.0 Hz, 1 H), 8.45 (d, J=8.5 Hz, 1 H), 7.62 (dd, J=8.5, 4.2 Hz, 1 H), 7.47-7.31 (m, 5 H), 6.76 (s, 1H), 4.39 (s, 2 H), 4.35-4.21 (m, 5 H), 3.75-3.71 (m, 4 H); MS m/z 417 (M+1).

b) 4-[7-(5-Benzyl-1,3,4-oxadiazol-2-yl)-8-hydroxy[1,6] naphthyridin-5-yl]-2-piperazinone. In a similar manner as described in example 25 from 4-[7-(5-Benzyl-1,3,4-oxadiazol-2-yl)-8-methoxy[1,6]naphthyridin-5-yl]-2-piperazinone (41 mg, 0.0985 mmol), sodium iodide (118 mg 0.788 mmol), and trimethylsilyl chloride (100 μL, 0.788 mmol), 4-[7-(5-Benzyl-1,3,4-oxadiazol-2-yl)-8-hydroxy[1,6]naphthyridin-5-yl]-2-piperazinone (9 mg, 23%) was obtained as a yellow solid. ¹H NMR (CDCl₃) δ 10.72 (br, 1 H), 9.23 (d, J=4.2 Hz, 1H), 8.48 (d, J=8.4 Hz, 1 H), 7.67 (dd, J=8.6, 4.2 Hz, 1 H), 7.50-7.31 (m, 5 H), 6.09 (s, 1 H), 4.42 (s, 2H), 4.17 (s, 2H), 3.67-3.65 (m, 4H); MS m/z 403 (M+1).

EXAMPLE 27

2-{4-[7-(5Benzyl-1,3,4-oxadiazol-2-yl)-8-hydroxy[1,6]naphthyridin-5-yl]-1-piperazinyl}-N,N-dimethylacetamide

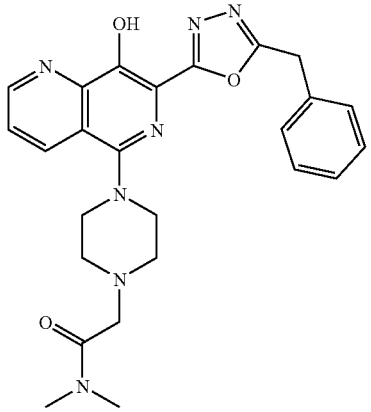

a) 2-{4-[7-(5-Benzyl-1,3,4-oxadiazol-2-yl)-8-methoxy[1,6]naphthyridin-5-yl]-1-piperazinyl}-N,N-dimethylacetamide. In a similar manner as described in example 25 from 7-(5-benzyl-1,3,4-oxadiazol-2-yl)-5-bromo[1,6]naphthyridin-8-yl methyl ether (50 mg, 0.126 mmol) and N,N-dimethyl-2-(1-piperazinyl)acetamide (216 mg, 1.26 mmol), 2-{4-[7-(5-benzyl-1,3,4-oxadiazol-2-yl)-8-methoxy[1,6]naphthyridin-5-yl]-1-piperazinyl}-N,N-dimethylacetamide (45 mg, 74%) was obtained as a yellow solid. ¹H NMR (CDCl₃) δ 9.07 (dd, J=4.4, 1.6 Hz, 1 H), 8.40 (dd, J=8.4, 1.6 Hz, 1 H), 7.52 (dd, J=8.4, 4.0 Hz, 1 H), 7.41 (d, J=7.2 Hz, 2 H), 7.33 (t, J=8.0 Hz, 2 H), 7.28 (d, J=7.2 Hz, 1 H), 4.34 (s, 2 H, 4.13 (s, 3 H), 3.48(t, J=4.8 Hz, 4 H), 3.30 (s, 2H), 3.12 (s, 3 H), 2.97 (s, 3 H), 2.80 (t, J=4.8 Hz, 4 H); MS m/z 488 (M+1).

b) 2-{4-[7-(5-Benzyl-1,3,4-oxadiazol-2-yl)-8-hydroxy[1,6]naphthyridin-5-yl]-1-piperazinyl}-N,N-dimethylacetamide. In a similar manner as described in example 25 from 2-{4-[7-(5-benzyl-1,3,4-oxadiazol-2-yl)-8-methoxy[1,6]naphthyridin-5-yl]-1-piperazinyl}-N,N-dimethylacetamide (47 mg, 0.0964 mmol), sodium iodide (116 mg 0.771 mmol), and trimethylsilyl chloride (97 μL, 0.771 mmol), 2-{4-[7-(5-benzyl-1,3,4-oxadiazol-2-yl)-8-hydroxy[1,6]naphthyridin-5-yl]-1-piperazinyl}-N,N-dimethylacetamide (20 mg, 44%) was obtained as a yellow solid. ¹H NMR (CDCl₃) δ 9.18 (d, J=3.9 Hz, 1H), 8.46 (d, J=8.4 Hz, 1 H), 7.63 (dd, J=8.4, 4.2 Hz, 1H), 7.49-7.36 (m, 5 H), 4.42 (s, 2 H), 3.45 (m, 4 H), 3.39 (s, 2H), 3.18 (s, 3 H), 3.04 (s, 3 H), 2.90 (m, 4 H); MS m/z 474 (M+1).

EXAMPLE 28

7-(5-Benzyl-1,3,4-oxadiazol-2-yl)-5-[4-(2-pyrazinyl)-1-piperazinyl][1,6]naphthyridin-8-ol

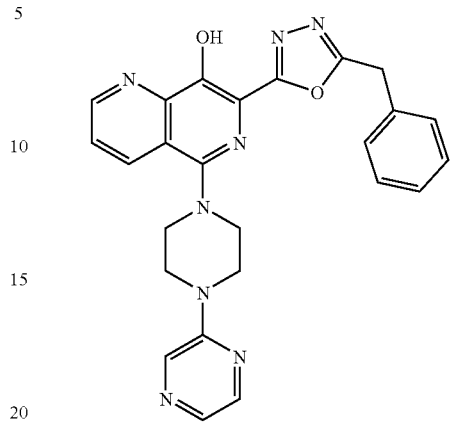

a) 7-(5-Benzyl-1,3,4-oxadiazol-2-yl)-5-[4-(2-pyrazinyl)-1-piperazinyl][1,6]naphthyridin-8-yl methyl ether. In a similar manner as described in example 25 from 7-(5-benzyl-1,3,4-oxadiazol-2-yl)-5-bromo[1,6]naphthyridin-8-yl methyl ether (50 mg, 0.126 mmol) and 1-(2-pyrazinyl)piperazine (207 mg, 1.26 mmol), 7-(5-benzyl-1,3,4-oxadiazol-2-yl)-5-[4-(2-pyrazinyl)-1-piperazinyl][1,6]naphthyridin-8-yl methyl ether (35 mg, 58%) was obtained as a yellow solid. ¹H NMR (CDCl₃) δ 9.19 (d, J=4.0 Hz, 1H), 8.52 (d, J=8.4, 1 H), 8.28 (s, 1H), 8.16 (d, J=1.3 Hz, 1 H), 7.96 (d, J=2.5 Hz, 1H), 7.63 (dd, J=8.5, 4.3 Hz, 1 H), 7.47-7.31 (m, 5 H), 4.40 (s, 2 H), 4.21 (s, 3 H), 3.91 (d, J=3.6 Hz, 4 H), 3.65 (d, J=2.9 Hz, 4 H); MS m/z 481 (M+1).

b) 7-(5-benzyl-1,3,4-oxadiazol-2-yl)-5-[4-(2-pyrazinyl)-1-piperazinyl][1,6]naphthyridin-8-ol. In a similar manner as described in example 25 from 7-(5-benzyl-1,3,4-oxadiazol-2-yl)-5-[4-(2-pyrazinyl)-1-piperazinyl][1,6]naphthyridin-8-yl methyl ether (32 mg, 0.0666 mmol), sodium iodide (80 mg 0.533 mmol), and trimethylsilyl chloride (68 μL, 0.533 mmol), 7-(5-benzyl-1,3,4-oxadiazol-2-yl)-5-[4-(2-pyrazinyl)-1-piperazinyl][1,6]naphthyridin-8-ol (20 mg, 65%) was obtained as a pale yellow solid. ¹H NMR (CDCl₃) δ 10.68 (br, 1 H), 9.22 (d, J=4.1 Hz, 1 H), 8.55 (d, J=8.3 Hz, 1H), 8.30 (s,1 H), 8.17 (s, 1 H), 7.98 (d, J=2.5 Hz, 1 H), 7.86 (dd, J=8.5, 4.2 Hz, 1 H), 7.49-7.36 (m, 5 H), 4.42 (s, 2H), 3.91 (m, 4 H), 3.54 (t, J=5.1 Hz, 4 H); MS m/z 467 (M+1).

EXAMPLE 29

7-(5-Benzyl-1,3,4-oxadiazol-2-yl)-5-(4-methoxyanilino)[1,6]naphthyridin-8-ol

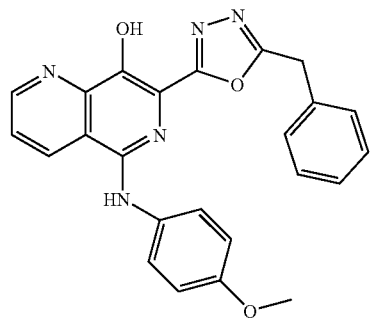

a) N-[7-(5-Benzyl-1,3,4-oxadiazol-2-yl)-8-methoxy[1,6]naphthyridin-5-yl]-N-(4-methoxyphenyl)amine. To a solution of 7-(5-benzyl-1,3,4-oxadiazol-2-yl)-5-bromo[1,6]naphthyridin-8-yl methyl ether (50 mg, 0.126 mmol) in toluene (2 mL) was added p-anisidine (47 mg, 0.378 mmol), cesium carbonate (62 mg, 0.189 mmol), 2,2'-bis(diphenylphosphino)-1,1'-binaphthyl (23 mg, 0.0378 mg), and palladium acetate (6 mg, 0.0252 mmol) respectively. The solution was de-oxygenated with nitrogen, then heated in a sealed tube at 105° C. for 2 hours. The reaction mixture was concentrated and chromatographed on silica gel (1% to 5% methanol in dichloromethane) to provide N-[7-(5-benzyl-1,3,4-oxadiazol-2-yl)-8-methoxy[1,6]naphthyridin-5-yl]-N-(4-methoxyphenyl)amine (32 mg, 55%) as a brown solid. $^1$H NMR (CDCl$_3$) δ 9.02 (dd, J=4.4, 1.2 Hz, 1 H), 8.41 (d, J=8.4 Hz, 1 H), 7.65 (d, J=8.8 Hz, 2 H), 7.46 (dd, J=8.8, 4.4 Hz, 1 H), 7.35-7.27 (m, 5 H), 6.81 (d, J=8.8 Hz, 2 H), 4.30 (s, 2 H), 4.08 (s, 3 H), 3.78 (s, 3 H); MS m/z 440 (M+1).

b) 7-(5-Benzyl-1,3,4-oxadiazol-2-yl)-5-(4-methoxyanilino)[1,6]naphthyridin-8-ol. In a similar manner as described in example 25 from N-[7-(5-benzyl-1,3,4-oxadiazol-2-yl)-8-methoxy[1,6]naphthyridin-5-yl]-N-(4-methoxyphenyl)amine (31 mg, 0.0705 mmol), sodium iodide (85 mg, 0.564 mmol), and trimethylsilyl chloride (72 μL, 0.564 mmol), 7-(5-benzyl-1,3,4-oxadiazol-2-yl)-5-(4-methoxyanilino)[1,6]naphthyridin-8-ol (13 mg, 43%) was obtained as a gold solid. $^1$H NMR (CDCl$_3$/CD$_3$OD) δ 9.08 (s, 1 H), 8.50 (d, J=8.1 Hz, 1 H), 7.67 (d, J=8.7 Hz, 2 H), 7.61 (m, 1H), 7.45-7.34 (m, 5 H), 6.90 (d, J=8.5 Hz, 2 H), 4.34 (s, 2 H), 3.85 (s, 3 H); MS m/z 426 (M+1).

EXAMPLE 30

7-[5-(4-Chlorobenzyl)-4H-1,2,4-triazol-3-yl]-1,6-naphthyridin-8-ol

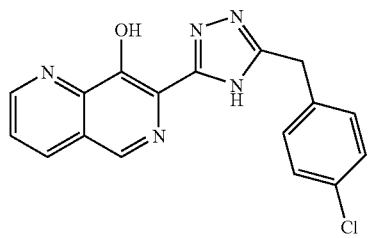

a) 2-(4-Chlorophenyl)acetic hydrazide. A solution of (4-chlorophenyl)acetyl chloride (10 g, 60 mmol) in dichloromethane (100 mL) was added dropwise to a cold (0° C.) solution of hydrazine (47 mL, 1.50 mol) in dichloromethane (400 mL), and the resultant mixture was stirred 3 hours. Water and dichloromethane were added and the mixture was extracted once with dichloromethane. The organic layer was concentrated in vacuo to a white solid. Recrystallization from methanol and dichloromethane afforded 2-(4-chlorophenyl) acetic hydrazide (4.06 g, 37%) as a white solid. $^1$H NMR (CDCl$_3$/CD$_3$OD): δ 7.19 (m, 2 H), 7.13 (m, 2 H), 3.37 (s, 2 H); MS m/z 185 (M+1).

b) 7-[5-(4-Chlorobenzyl)-4H-1,2,4-triazol-3-yl]-1,6-naphthyridin-8-ol. In a similar manner as described in example 1, 7-[5-(4-chlorobenzyl)-4H-1,2,4-triazol-3-yl]-1,6-naphthyridin-8-ol (71 mg, 36%) was prepared as a yellow solid. $^1$H NMR (CDCl$_3$/CD$_3$OD): δ 9.02 (d, J=4.2 Hz, 1 H), 8.75 (s, 1 H), 8.25 (d, J=8.3 Hz, 1 H), 7.56 (dd, J=12.5, 4.2Hz, 1 H), 7.26-7.19 (m, 4 H), 4.10 (s, 21H); MS m/z 338 (M+1).

EXAMPLE 31

7-[5(2-Phenylethyl)-4H-1,2,4-triazol-3-yl]-1,6-naphthyridin-8-ol

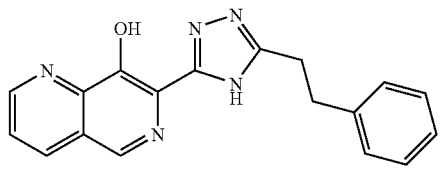

a) 3-Phenylpropanohydrazide. In a similar manner as described in example 2, 3-phenylpropanohydrazide (5.22 g, 54%) was prepared as a white solid. $^1$H NMR (CDCl$_3$): δ 7.31-7.25 (m, 2 H), 7.23-7.17 (m, 3 H), 6.64 (s, 1 H), 2.97 (t, J=15.2, 7.6Hz, 2 H), 2.45 (t, J=15.2, 7.6 Hz, 2 H) ; MS m/z 165 (M+1).

b) 7-[5-(2-Phenylethyl)-4H-1,2,4-triazol-3-yl]-1,6-naphthyridin-8-ol. In a similar manner as described in example 1, 7-[5-(2-phenylethyl)-4H-1,2,4-triazol-3-yl]-1,6-naphthyridin-8-ol (100 mg, 50%) was prepared as a yellow solid. $^1$H NMR (CDCl$_3$/CD$_3$OD): δ 8.90 (dd, J=4.4, 1.6 Hz, 1 H), 8.67 (s, 1 H), 8.20 (dd, J=8.4, 1.6 Hz, 1 H), 7.47 (dd, J=8.4, 4.4 Hz, 1 H), 7.11-6.98 (m, 5 H), 3.14 (m, 2 H), 2.98 (s, 2 H); MS m/z 340 (M+Na).

EXAMPLE 32

7-[5-(1-Naphthylmethyl)-4H-1,2,4-triazol-3-yl]-1,6-naphthyridin-8-ol

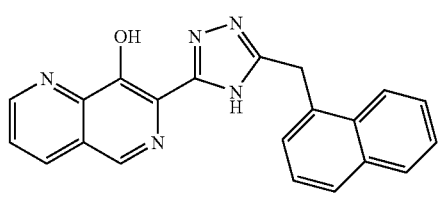

In a similar manner as described in example 1, 7-[5-(1-naphthylmethyl)-4H-1,2,4-triazol-3-yl]-1,6-naphthyridin-8-ol (15 mg, 14%) was prepared as a yellow solid. $^1$H NMR (CDCl$_3$/CD$_3$OD): δ 8.95 (dd, J=4.4, 1.2 Hz, 1 H), 8.69 (s, 1 H), 8.20 (dd, J=8.4, 1.2 Hz, 1 H), 8.06 (d, J=8.4 Hz, 1 H), 7.74 (d, J=7.6 Hz, 1 H), 7.67 (d, J=8.4 Hz, 1 H), 7.50 (dd, J=8.4, 4.4 Hz, 1 H), 7.41-7.29 (m, 4 H), 4.55 (s, 2 H); MS m/z 376 (M+Na).

EXAMPLE 33

5-(1,1-Dioxido-1,2-thiazinan-2-yl)-7-[5-(2-phenyl-ethyl)-4H-1,2,4-triazol-3-yl]-1,6-naphthyridin-8-ol

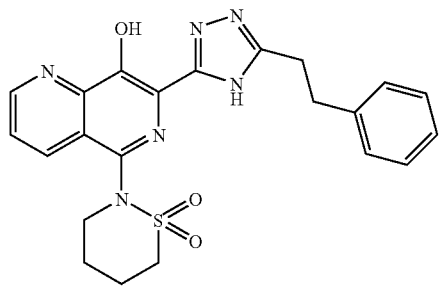

In a similar manner as described in example 3, 5-(1,1-dioxido-1,2-thiazinan-2-yl)-7-[5-(2-phenylethyl)-4H-1,2,4-triazol-3-yl]-1,6-naphthyridin-8-ol (30 mg, 25%) was prepared as a yellow solid. $^1$H NMR (CDCl$_3$/CD$_3$OD): δ 9.18 (d, J=4.4 Hz, 1 H), 8.62 (d, J=8.4 Hz, 1 H), 7.65 (dd, J=8.4, 4.4 Hz, 1 H), 7.31-7.20 (m, 5 H), 4.02 (m, 1 H), 3.91 (m, 1 H), 3.47 (m, 1 H), 3.34 (m, 1 H), 3.23-3.18 (m, 4 H), 2.55-2.26 (m, 3 H), 1.86 (m, 1 H); MS m/z 473 (M+Na).

EXAMPLE 34

7-[5-(Pyridin-4-ylmethyl)-4H-1,2,4-triazol-3-yl]-1,6-naphthyridin-8-ol

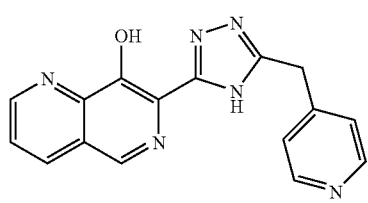

a) 2-Pyridin-4-ylacetic hydrazide. A mixture of hydrazine hydrate (0.27 mL, 9.08 mmol), ethyl pyridin-4-ylacetate (0.93 mL, 6.05 mmol) and ethanol (10 mL) was heated at 80° C. for 10 hours. An additional 0.6 mL of hydrazine were added and the mixture was heated for 14 hours. The solution was cooled to room temperature and concentrated in vacuo. 2-Pyridin-4-ylacetic hydrazide (0.86 g, 95%) was thus obtained as a white solid. $^1$H NMR (DMSO): δ 9.29 (s, 1 H), 8.47 (d, J=5.6 Hz, 2 H), 7.27 (d, J=5.2 Hz, 2 H), 4.28 (s, 2 H), 3.39 (s, 2 H); MS m/z 152 (M+1).

b) 7-[5-(Pyridin-4-ylmethyl)-4H-1,2,4-triazol-3-yl]-1,6-naphthyridin-8-ol. In a similar manner as described in example 1, 7-[5-(pyridin-4-ylmethyl)-4H-1,2,4-triazol-3-yl]-1,6-naphthyridin-8-ol (72 mg, 41%) was prepared as a yellow solid. $^1$H NMR (CDCl$_3$/CD$_3$OD): δ 9.81 (dd, J=4.4, 1.6 Hz, 1 H), 8.78 (s, 1 H), 8.43 (dd, J=4.8, 1.6 Hz, 2 H), 8.28 (dd, J=8.4, 1.6 Hz, 1 H), 7.59 (dd, J=8.4, 4.4 Hz, 1 H), 7.30 (d, J=6 Hz, 2 H), 4.19 (s, 2 H); MS m/z 305 (M+1).

EXAMPLE 35

7-[5-(Pyridin-3-ylmethyl)-4H-1,2,4-triazol-3-yl]-1,6-naphthyridin-8-ol

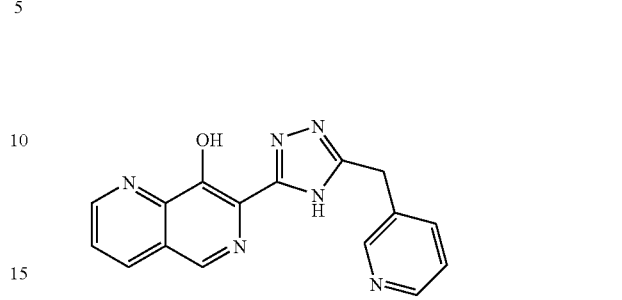

a) 2-Pyridin-3-ylacetic hydrazide. In a similar manner as described in example 34, 2-pyridin-3-ylacetic hydrazide was prepared as a white solid. $^1$H NMR (DMSO): δ 9.26 (s, 1 H), 8.43-8.40 (m, 2 H), 7.66-7.63 (m, 1 H), 7.33-7.29 (m, 1 H), 4.25 (s, 2 H), 3.36 (s, 2H).

b) 7-[5-(Pyridin-3-ylmethyl)-4H-1,2,4-triazol-3-yl]-1,6-naphthyridin-8-ol. In a similar manner as described in example 34, 7-[5-(pyridin-3-ylmethyl)-4H-1,2,4-triazol-3-yl]-1,6-naphthyridin-8-ol (17 mg, 38%) was prepared as a yellow solid. $^1$H NMR (CDCl$_3$/CD$_3$OD): δ 9.05 (d, J=4.4, 1 H), 8.83 (s, 1 H), 8.53 (s, 1 H), 8.39 (d, J=4.8 Hz, 1 H), 8.35 (d, J=8.4 Hz, 1 H), 7.78 (d, J=8.0 Hz, 1 H), 7.63 (dd, J=8.4, 4.4 Hz, 1 H), 7.32 (m, 1 H), 4.22 (s, 2 H); HRMS calcd for C$_{16}$H$_{12}$N$_6$O (M+1) 305.1151, found 305.1159. Anal. Calcd for C$_{16}$H$_{12}$N$_6$O.H$_2$O: C, 59.62; H, 4.38; N, 26.07. Found: C, 59.53; H, 4.12; N, 26.07.

EXAMPLE 36

5-(1,1-Dioxido-1,2-thiazinan-2-yl)-7-[5-(3-methoxy-benzyl)-4H-1,2,4-triazol-3-yl]-1,6-naphthyridin-8-ol

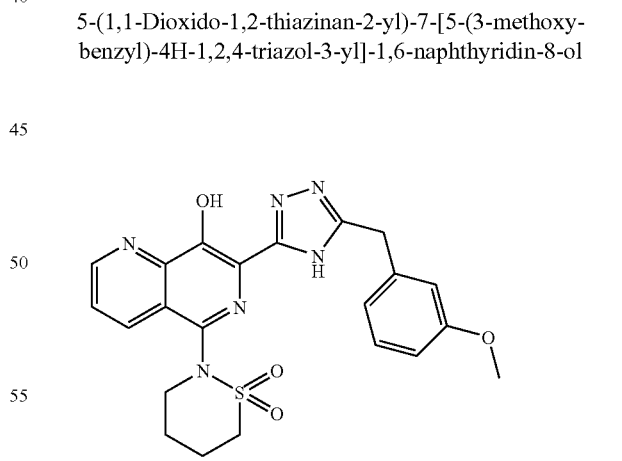

In a similar manner as described in example 3, 5-(1,1-dioxido-1,2-thiazinan-2-yl)-7-[5-(3-methoxybenzyl)-4H-1,2,4-triazol-3-yl]-1,6-naphthyridin-8-ol (10 mg) was prepared as a white solid. $^1$H NMR (CDCl$_3$): δ 8.95 (s, 1 H), 8.48 (d, J=8.4 Hz, 1 H), 7.54 (m, 1 H), 7.07 (m, 1 H), 6.80-6.75 (m, 2 H), 6.62 (d, J=7.2 Hz, 1 H), 4.08-4.02 (m, 5 H), 3.69-3.48 (m, 4 H), 2.30-2.27 (m, 3 H).), 1.69 (s, 1 H); MS m/z 467 (M+1).

EXAMPLE 37

5-(1,1-Dioxido-1,2-thiazinan-2-yl)-7-[5-(pyridin-3-ylmethyl)-4H-1,2,4-triazol-3-yl]-1,6-naphthyridin-8-ol

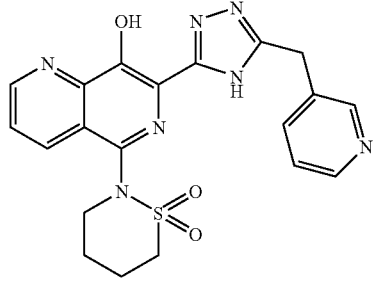

In a similar manner as described in example 3, 5-(1,1-dioxido-1,2-thiazinan-2-yl)-7-[5-(pyridin-3-ylmethyl)-4H-1,2,4-triazol-3-yl]-1,6-naphthyridin-8-ol (36 mg, 23%) was prepared as a yellow solid. $^1$H NMR (CD$_3$OD/CDCl$_3$): δ 9.01 (d, J=2.8 Hz, 1 H), 8.59 (m, 1 H), 8.52 (s, 1 H), 8.38 (d, J=4.4 Hz, 1 H), 7.77 (d, J=7.6 Hz, 1 H), 7.64 (dd, J=8.4, 4.4 Hz, 1 H), 7.31 (m, 1 H), 4.20 (s, 2 H), 3.87 (m, 1 H), 3.81 (m, 1 H), 3.64 (m, 1 H), 3.30 (m, 1 H), 2.41 (s, 3 H),1.80 (m, 1 H); MS m/z 438 (M+1).

EXAMPLE 38

5-(1,1-Dioxido-1,2-thiazinan-2-yl)-7-[5-(pyridin-4-ylmethyl)-4H-1,2,4-triazol-3-yl]-1,6-naphthyridin-8-ol

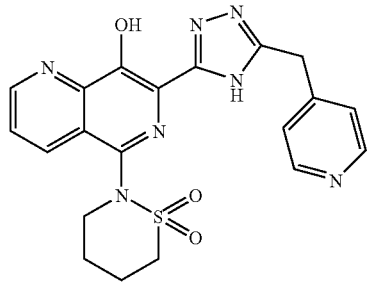

In a similar manner as described in example 3, 5-(1,1-dioxido-1,2-thiazinan-2-yl)-7-[5-(pyridin-4-ylmethyl)-4H-1,2,4-triazol-3-yl]-1,6-naphthyridin-8-ol (15 mg, 10%) was prepared as a yellow solid. $^1$H NMR (CDCl$_3$/CD$_3$OD): δ 9.17 (d, J=2.8 Hz, 1 H), 8.60 (dd, J=8.4, 1.2 Hz, 1 H), 8.54 (d, J=5.2 Hz, 2 H), 7.65 (dd, J=8.4, 4.4 Hz, 1 H), 7.32 (d, J=5.2 Hz, 2 H), 4.23 (s, 2 H), 3.91 (m, 1 H), 3.85 (m, 1 H), 3.48 (m, 1 H), 3.27 (m, 1 H), 2.50-2.20 (m, 3 H), 1.77 (s, 1 H); MS m/z 460 (M+Na).

EXAMPLE 39

5-(1,1-Dioxido-1,2-thiazinan-2-yl)-7-[5-(pyridin-2-ylmethyl)-4H-1,2,4-triazol-3-yl]-1,6-naphthyridin-8-ol

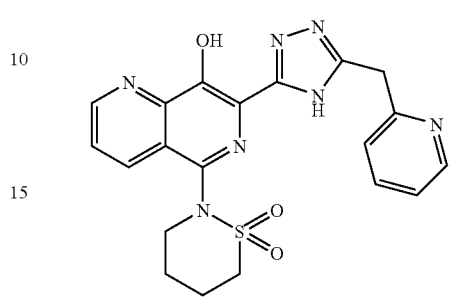

a) 2-Pyridin-2-ylacetic hydrazide. In a similar manner as described in example 34, 2-pyridin-2-ylacetic hydrazide (2.5 g, 92%) was prepared as a yellow solid. $^1$H NMR (DMSO): δ 9.25 (s, 1 H), 8.46 (d, J=4.4 Hz, 1 H), 7.72 (td, J=2.0, 2.0, 1.6 Hz, 1 H), 7.33 (d, J=7.6 Hz, 1 H), 7.23 (dd, J=7.6, 5.2 Hz, 1 H), 4.24 (s, 2 H), 3.54 (s, 2 H); MS m/z 152 (M+1).

b) 5-(1,1-Dioxido-1,2-thiazinan-2-yl)-7-[5-(pyridin-2-ylmethyl)-4H-1,2,4-triazol-3-yl]-1,6-naphthyridin-8-ol. In a similar manner as described in example 3, 5-(1,1-dioxido-1,2-thiazinan-2-yl)-7-[5-(pyridin-2-ylmethyl)-4H-1,2,4-triazol-3-yl]-1,6-naphthyridin-8-ol (11 mg) was prepared as a white solid. $^1$H NMR (CDCl$_3$/CD$_3$OD): δ 8.94 (d, J=3.2 Hz, 1 H), 8.48 (dd, J=8.4, 1.2 Hz, 1 H), 8.34 (d, J=4.8 Hz, 1 H), 7.60-7.52 (m, 3 H), 7.10 (m, 1 H), 4.26 (s, 2 H), 3.80-3.60 (m, 3 H), 3.50 (s, 1 H), 2.30 (s, 3 H), 1.67 (s, 1 H); MS m/z 460 (M+Na).

EXAMPLE 40

7-[5-(3,5-Difluorobenzyl)-4H-1,2,4-triazol-3-yl]-5-(1,1-dioxido-1,2-thiazinan-2-yl)-1,6-naphthyridin-8-ol

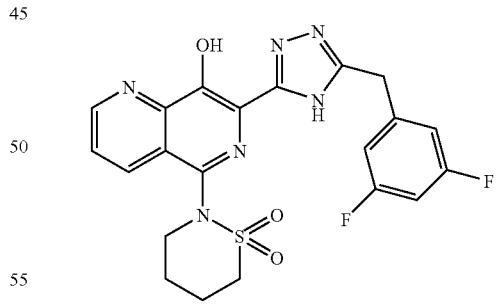

a) 2-(3,5-Difluorophenyl)acetic hydrazide. A mixture of (3,5-difluorophenyl)acetic acid (3 g, 17.4 mmol) and thionyl chloride were heated at 81° C. for 2 hours. The solution was cooled to room temperature and concentrated in vacuo to clear oil. The oil was coevaporated once with toluene, dissolved in dichloromethane (20 mL) and added dropwise to a cold (0° C.) solution of hyrdazine (13.7 mL, 435 mmol) in dichloromethane (100 mL). This solution was stirred for 30 minutes, diluted with water and extracted with dichloromethane. The combined organics were concentrated in vacuo to yield 2-(3,5-difluorophenyl)acetic hydrazide (409.3 mg, 13%) as a white solid. $^1$H NMR (DMSO): δ 9.24 (s, 1 H), 7.09 (m, 1 H), 6.97 (dd, J=8.4, 2.0 Hz, 2 H), 4.25 (s, 2 H), 3.39 (s, 2 H); MS m/z 187 (M+1).

b) 7-[5-(3,5-Difluorobenzyl)-4H-1,2,4-triazol-3-yl]-5-(1,1-dioxido-1,2-thiazinan-2-yl)-1,6-naphthyridin-8-ol. In a similar manner as described in example 3, 7-[5-(3,5-difluorobenzyl)-4H-1,2,4-triazol-3-yl]-5-(1,1-dioxido-1,2-thiazinan-2-yl)-1,6-naphthyridin-8-ol (5.2 mg) was prepared as a white solid. $^1$H NMR (CDCl$_3$): δ 9.12 (d, J=2.8 Hz, 1 H), 8.61 (d, J=7.6 Hz, 1 H), 7.66 (dd, J=8.4, 4.4 Hz, 1 H), 6.91-6.89 (m, 2 H), 6.69 (m, 1 H), 4.20 (s, 2 H), 4.00-3.88 (m, 2 H), 3.50-3.42 (m, 1 H), 3.32 (s, 1 H), 2.49-2.25 (m, 3 H), 1.84 (m, 1 H); MS m/z 473 (M+1).

EXAMPLE 41

5-(1,1-Dioxido-1,2-thiazinan-2-yl)-7-[5-(thien-2-ylmethyl)-4H-1,2,4-triazol-3-yl]-1,6-naphthyridin-8-ol

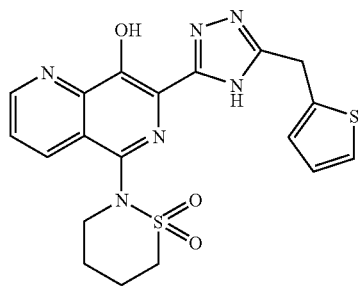

a) 2-Thien-2-ylacetic hydrazide. In a similar manner as described in example 30, 2-thien-2-ylacetic hydrazide (486 mg, 50%) was prepared as a white solid. $^1$H NMR (DMSO): δ 9.23 (s, 1 H), 7.34 (dd, J=5.2, 0.8 Hz, 1 H), 6.94 (t, J=4.8, 3.6 Hz, 1 H), 6.89 (d, J=3.2 Hz, 1 H), 4.25 (s, 2 H), 3.57 (s, 2 H); MS m/z 157 (M+1).

b) 5-(1,1-Dioxido-1,2-thiazinan-2-yl)-7-[5-(thien-2-ylmethyl)-4H-1,2,4-triazol-3-yl]-1,6-naphthyridin-8-ol. In a similar manner as described in example 3, 5-(1,1-dioxido-1,2-thiazinan-2-yl)-7-[5-(thien-2-ylmethyl)-4H-1,2,4-triazol-3-yl]-1,6-naphthyridin-8-ol (7 mg) was prepared as a white solid. $^1$H NMR (CDCl$_3$): δ 9.17 (dd, J=4.4, 1.6 Hz, 1 H), 8.61 (dd, J=8.8, 1.6 Hz, 1 H), 7.65 (dd, J=8.4, 4.4 Hz, 1 H), 7.20 (d, J=4.4 Hz, 1 H), 7.02 (m, 1 H), 6.95 (m, 1 H), 4.44 (s, 2 H), 4.00 (m, 1 H), 3.88 (m, 1 H), 3.48 (m, 1 H), 3.31 (m, 1 H), 2.55-2.29 (m, 3 H), 1.81 (m, 1 H); MS m/z 443 (M+1).

EXAMPLE 42

5-(1,1-Dioxido-1,2-thiazinan-2-yl)-7-[5-(3-fluorobenzyl)-4H-1,2,4-triazol-3-yl]-1,6-naphthyridin-8-ol

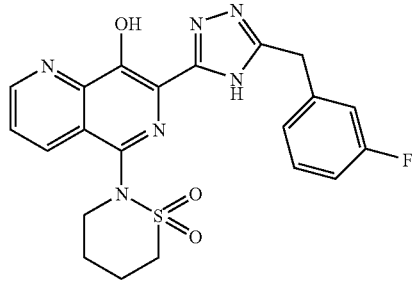

a) 2-(3-Fluorophenyl)acetic hydrazide. In a similar manner as described in example 40, 2-(3-fluorophenyl)acetic hydrazide (626 mg, 11%) was prepared as a white solid. $^1$H NMR (CDCl$_3$): δ 9.24 (s, 1 H), 7.33-(dd, J=14.8, 7.6 Hz, 1 H), 7.10-7.03 (m, 3 H), 4.23 (s, 2 H), 3.38 (s, 2 H); MS m/z 169 (M+1).

b) 5-(1,1-Dioxido-1,2-thiazinan-2-yl)-7-[5-(3-fluorobenzyl)-4H-1,2,4-triazol-3-yl]-1,6-naphthyridin-8-ol. In a similar manner as described in example 3, 5-(1,1-dioxido-1,2-thiazinan-2-yl)-7-[5-(3-fluorobenzyl)-4H-1,2,4-triazol-3-yl]-1,6-naphthyridin-8-ol (7 mg) was prepared as a white solid. $^1$H NMR (CDCl$_3$): δ 9.16 (d, J=2.8 Hz, 1 H), 8.61 (d, J=8.4 Hz, 1 H), 7.65 (dd, J=8.4, 4.0 Hz, 1 H), 7.27 (m, 1 H), 7.16 (m, 1 H), 7.07 (m, 1 H), 6.93 (m, 1 H), 4.22 (s, 2 H), 3.98 (m, 1 H), 3.88 (m, 1 H), 3.47 (m, 1 H), 3.31 (m, 1 H), 2.51-2.25 (m, 3 H), 1.82 (m, 1 H); MS m/z 455 (M+1).

EXAMPLE 43

7-[5-(3,4-Difluorobenzyl)-4H-1,2,4-triazol-3-yl]-5-(1,1-dioxido-1,2-thiazinan-2-yl)-1,6-naphthyridin-8-ol

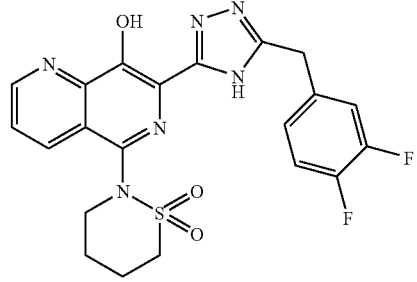

a) 2-(3,4-Difluorophenyl)acetic hydrazide. In a similar manner as described in example 40, 2-(3,4-difluorophenyl)acetic hydrazide (1.04 g, 48%) was prepared as a white solid. $^1$H NMR (DMSO): δ 9.19 (s, 1 H), 7.37-7.25 (m, 2 H), 7.05 (m, 1 H), 4.23 (s, 2 H), 3.31 (2 H); MS m/z 187 (M+1).

b) 7-[5-(3,4-Difluorobenzyl)-4H-1,2,4-triazol-3-yl]-5-(1,1-dioxido-1,2-thiazinan-2-yl)-1,6-naphthyridin-8-ol. In a similar manner as described in example 3, 7-[5-(3,4-difluorobenzyl)-4H-1,2,4-triazol-3-yl]-5-(1,1-dioxido-1,2-thiazinan-2-yl)-1,6-naphthyridin-8-ol (6 mg) was prepared as a white solid. $^1$H NMR (CDCl$_3$): δ 9.17 (d, J=4 Hz, 1 H), 8.61 (d, J=7.6 Hz, 1 H), 7.66 (dd, J=8.4, 4.0 Hz, 1 H), 7.18 (m, 1 H), 7.12-7.08 (m, 2 H), 4.18 (s, 2 H), 3.95-3.90 (m, 2 H), 3.54-3.32 (m, 2 H), 2.63-2.11 (m, 3 H), 1.85 (m, 1 H); MS m/z 473 (M+1).

EXAMPLE 44

7-[5-(2,3-Difluorobenzyl)-4H-1,2,4-triazol-3-yl]-5-(1,1-dioxido-1,2-thiazinan-2-yl)-1,6-naphthyridin-8-ol

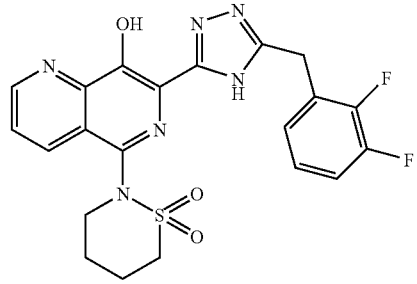

a) 2-(2,3-Difluorophenyl)acetic hydrazide. In a similar manner as described in example 40, 2-(2,3-difluorophenyl) acetic hydrazide (1.77 g, 54%) was prepared as a white solid. $^1$H NMR (DMSO): δ 9.26 (s, 1 H), 7.29 (m, 1 H), 7.16-7.13 (m, 2 H), 4.26 (s, 2 H), 3.47 (s, 2 H); MS m/z 187 (M+1).

b) 7-[5-(2,3-Difluorobenzyl)-4H-1,2,4-triazol-3-yl]-5-(1,1-dioxido-1,2-thiazinan-2-yl)-1,6-naphthyridin-8-ol. In a similar manner as described in example 3, 7-[5-(2,3-difluorobenzyl)-4H-1,2,4-triazol-3-yl]-5-(1,1-dioxido-1,2-thiazinan-2-yl)-1,6-naphthyridin-8-ol (4.2 mg) was prepared as a white solid. $^1$H NMR (CDCl$_3$): δ 9.16 (d, J=3.2 Hz, 1 H), 8.61 (d, J=8.4 Hz, 1 H), 7.65 (dd, J=8.4, 4.4 Hz, 1 H), 7.12-7.02 (m, 3 H), 4.18 (s, 2 H), 3.98-3.87 (m, 2 H), 3.47 (m, 1 H), 3.30 (m, 1 H), 2.38 (m, 3 H), 1.81 (m, 1H); MS m/z 473 (M+1).

EXAMPLE 45

7-[5-(Cyclopentylmethyl)-4H-1,2,4-triazol-3-yl]-5-(1,1-dioxido-1,2-thiazinan-2-yl)-1,6-naphthyridin-8-ol

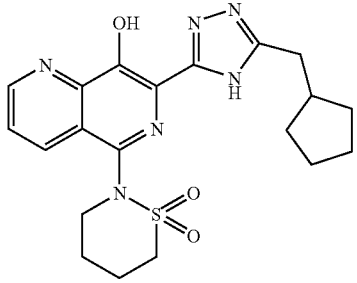

2-Cyclopentylacetic hydrazide. In a similar manner as described in example 40, 2-cyclopentylacetic hydrazide (3 g, 88%) was prepared as a white solid. $^1$H NMR (DMSO): δ 9.90 (s, 1 H), 4.14 (s, 2 H), 2.10 (m, 1 H), 1.99 (d, J=7.6 Hz, 2 H), 1.66 (m, 2 H), 1.57-1.45 (m, 4 H), 1.02 (m, 2 H); MS m/z 143 (M+1).

b) 7-[5-(Cyclopentylmethyl)-4H-1,2,4-triazol-3-yl]-5-(1,1-dioxido-1,2-thiazinan-2-yl)-1,6-naphthyridin-8-ol. In a similar manner as described in example 3, 7-[5-(cyclopentylmethyl)-4H-1,2,4-triazol-3-yl]-5-(1,1-dioxido-1,2-thiazinan-2-yl)-1,6-naphthyridin-8-ol (6 mg) was prepared as a white solid. $^1$H NMR (CDCl$_3$): δ 9.17 (dd, J=4.0, 1.2 Hz, 1 H), 8.63 (dd, J=8.4, 1.6 Hz, 1 H), 7.65 (dd, J=8.4, 4.0 Hz, 1 H), 4.05 (m, 1 H), 3.86 (m, 1 H), 3.51 (m, 1 H), 3.32 (m, 1 H), 2.88 (d, J=8.0 Hz, 2 H), 2.43-2.34 (m, 4 H), 1.87-1.81 (m, 3 H), 1.70-1.53 (m, 5 H), 1.37-1.27 (m, 1 H); MS m/z 429 (M+1).

EXAMPLE 46

7-[5-(4-Fluorobenzyl)-4H-1,2,4-triazol-3-yl]-5-thiomorpholin-4-yl-1,6-naphthyridin-8-ol

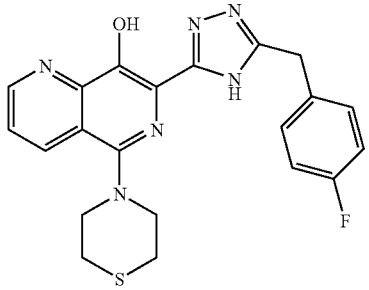

7-[5-(4-Fluorobenzyl)-4H-1,2,4-triazol-3-yl]-5-thiomorpholin-4-yl-1,6-naphthyridin-8-ol. In a similar manner as described in example 17, 7-[5-(4-fluorobenzyl)-4H-1,2,4-triazol-3-yl]-5-thiomorpholin-4-yl-1,6-naphthyridin-8-ol (2.7 mg, 12%) was prepared as a brown solid. $^1$H NMR (CDCl$_3$): δ 9.12 (dd, J=4.4, 1.6 Hz, 1 H), 8.37 (dd, J=8.4, 1.6 Hz, 1 H), 7.55 (dd, J=8.4, 4.4 Hz, 1 H), 7.35 (m, 2 H), 7.01 (m, 2 H), 4.18 (s, 2 H), 3.58 (s, 4 H), 2.92 (s, 4 H); MS m/z 423 (M+1).

EXAMPLE 47

7-[5-(4-Fluorobenzyl)-4H-1,2,4-triazol-3-yl]-5-piperidin-1-yl-1,6-naphthyridin-8-ol

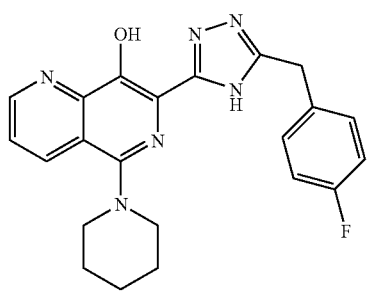

7-[5-(4-Fluorobenzyl)-4H-1,2,4-triazol-3-yl]-5-piperidin-1-yl-1,6-naphthyridin-8-ol. In a similar manner as described in example 17, 7-[5-(4-fluorobenzyl)-4H-1,2,4-triazol-3-yl]-5-piperidin-1-yl-1,6-naphthyridin-8-ol (7 mg, 34%) was prepared as a yellow solid. $^1$H NMR (CDCl$_3$): δ 9.08 (dd, J=4.4, 1.6 Hz, 1 H), 8.40 (dd, J=8.4, 1.6 Hz, 1 H), 7.52 (dd, J=8.4, 4.4 Hz, 1 H), 7.35 (m, 2 H), 6.99 (m, 2 H), 4.17 (s, 2 H), 3.25 (s, 4 H), 1.82 (s, 4 H), 1.67 (m, 2 H); MS m/z 404 (M+1).

EXAMPLE 48

7-[5-(4-Fluorobenzyl)-4H-1,2,4-triazol-3-yl]-5-piperazin-1-yl-1,6-naphthyridin-8-ol

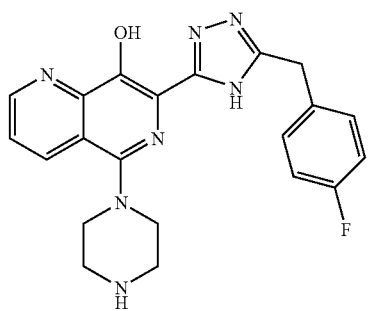

7-[5-(4-Fluorobenzyl)-4H-1,2,4-triazol-3-yl]-5-piperazin-1-yl-1,6-naphthyridin-8-ol. In a similar manner as described in example 17, 7-[5-(4-fluorobenzyl)-4H-1,2,4-triazol-3-yl]-5-piperazin-1-yl-1,6-naphthyridin-8-ol (7 mg, 21%) was prepared as the formic acid salt. $^1$H NMR (CD$_3$OD/CDCl$_3$): δ 9.02 (dd, J=4.4, 1.2 Hz, 1 H), 8.43 (m, 1 H), 7.58 (dd, J 8.4, 4.4 Hz, 1 H), 7.30 (m, 2 H), 6.95 (m, 2 H), 4.13 (s, 2 H), 3.49 (s, 4 H), 3.35 (s, 4 H); MS m/z 406 (M+1).

EXAMPLE 49

5-(1,1-Dioxidothiomorpholin-4-yl)-7-[5-(4-fluorobenzyl-4H-1,2,4-triazol-3-yl]-1,6-naphthyridin-8-ol

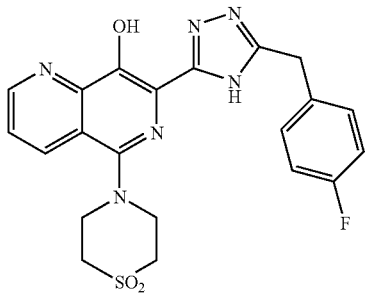

A 100 mL flask was charged with 7-[5-(4-fluorobenzyl)-4H-1,2,4-triazol-3-yl]-5-thiomorpholin-4-yl-1,6-naphthyridin-8-ol (26 mg, 0.062 mmol). Methanol (15 mL) and chloroform (~3 mL to dissolve insoluble solids) were added, followed by a freshly prepared 0.16 M solution of Oxone (0.75 mL, 0.12 mmol) in methanol. The solution was stirred for 14 hours at room temperature. The reaction mixture was concentrated in vacuo, diluted with dichloromethane and extracted twice. The combined organics were concentrated in vacuo and purified by preparative HPLC. Thus, 5-(1,1-dioxidothiomorpholin-4-yl)-7-[5-(4-fluorobenzyl)-4H-1,2,4-triazol-3-yl]-1,6-naphthyridin-8-ol (7.3 mg, 26%) was prepared as a tan solid. $^1$H NMR (CD$_3$OD/CDCl$_3$): δ 8.99 (dd, J=4.4, 1.6 Hz, 1 H), 8.31 (dd, J=8.4, 1.6 Hz, 1 H), 7.52 (dd, J=8.4, 4.4 Hz, 1 H), 7.24 (m, 2 H), 6.91 (m, 2 H), 4.08 (s, 2 H), 3.85 (m, 4 H), 3.25 (m, 4 H); MS m/z 455 (M+1).

EXAMPLE 50

7-[5-(4-Fluorobenzyl)-4H-1,2,4-triazol-3-yl]-5-(4-hydroxypiperidin-1-yl)-1,6-naphthyridin-8-ol

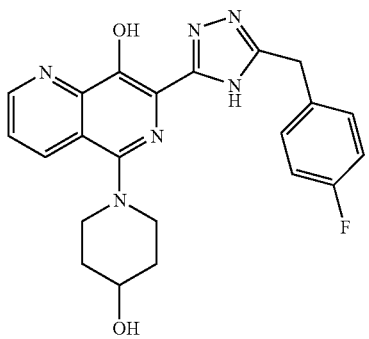

In a similar manner as described in example 17, 7-[5-(4-fluorobenzyl)-4H-1,2,4-triazol-3-yl]-5-(4-hydroxypiperidin-1-yl)-1,6-naphthyridin-8-ol (2 mg, 10%) was prepared as a yellow solid. $^1$H NMR (CD$_3$OD/CDCl$_3$): δ 9.01 (d, J=4.0 Hz, 1 H), 8.38 (d, J=8.4, 1 H), 7.51 (dd, J=8.4, 4.0 Hz, 1 H), 7.29 (m, 2 H), 6.95 (m, 2 H), 4.11 (s, 2 H), 3.89 (m, 2 H), 3.52 (m, 2 H), 3.07 (m, 1 H), 2.03 (m, 2 H), 1.81 (m, 2 H); MS m/z 421 (M+1).

EXAMPLE 51

7-[5-(4-Fluorobenzyl)-4H-1,2,4-triazol-3-yl]-5-(4-pyridin-2-ylpiperazin-1-yl)-1,6-naphthyridin-8-ol

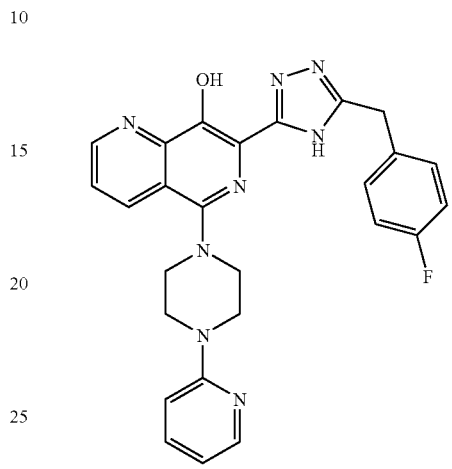

In a similar manner as described in example 17, 7-[5-(4-fluorobenzyl)-4H-1,2,4-triazol-3-yl]-5-(4-pyridin-2-ylpiperazin-1-yl)-1,6-naphthyridin-8-ol (15 mg) was prepared as a brown solid. $^1$H NMR (CDCl$_3$): δ 9.12 (d, J=4.0, 1.2 Hz, 1 H), 8.47(d, J=8.4, 1 H), 8.23 (d, J=4.0 Hz, 1 H), 7.55 (m, 2 H), 7.35 (m, 2 H), 6.99 (m, 2 H), 6.68 (m, 2 H), 4.18 (s, 2 H), 3.79(s, 4 H), 3.37 (s, 4 H); MS m/z 483 (M+1).

EXAMPLE 52

7-[5-(4-Fluorobenzyl)-4H-1,2,4-triazol-3-yl]-5-{4-[2-(2-hydroxyethoxy)ethyl]piperazin-1-yl}-1,6naphthyridin-8-ol

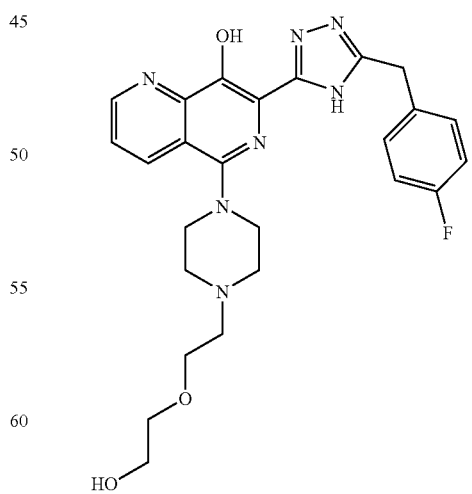

In a similar manner as described in example 17, 7-[5-(4-fluorobenzyl)-4H-1,2,4-triazol-3-yl]-5-{4-[2-(2-hydroxyethoxy)ethyl]piperazin-1-yl}-1,6-naphthyridin-8-ol (7 mg)

was prepared as formic acid salt. $^1$H NMR (CDCl$_3$): δ 9.10 (dd, J=4.0, 1.2 Hz, 1 H), 8.36 (dd, J=8.0, 1.2 Hz, 1 H), 7.52 (dd, J=8.4, 4.0 Hz, 1 H), 7.34 (m, 2 H), 6.98 (m, 2 H), 4.16 (s, 2 H), 3.79-3.76 (m, 2 H), 3.74-3.72 (m, 2 H), 3.65-3.62 (m, 2 H), 3.43-3.40 (m, 4 H), 3.03 (s, 4 H), 2.91-2.88 (m, 2 H); MS m/z 494 (M+1).

EXAMPLE 53

5-(4-Acetylpiperazin-1-yl)-7-[5-(4-fluorobenzyl)-4H-1,2,4-triazol-3-yl]-1,6-naphthyridin-8-ol

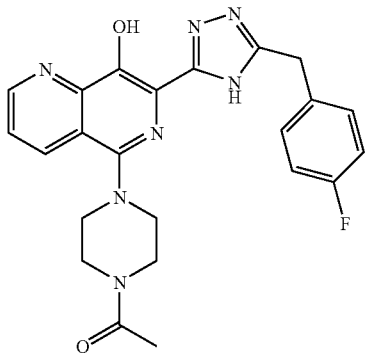

In a similar manner as described in example 17, 5-(4-acetylpiperazin-1-yl)-7-[5-(4-fluorobenzyl)-4H-1,2,4-triazol-3-yl]-1,6-naphthyridin-8-ol (38 mg, 57%) was prepared as a brown solid. $^1$H NMR (CDCl$_3$): δ 9.13 (d, J=4.4, 1.2 Hz, 1 H), 8.42 (d, J=8.4, 1.2 Hz, 1 H), 7.56 (dd, J=8.4, 4.4 Hz, 1 H), 7.34 (m, 2 H), 6.97 (m, 2 H), 4.17 (s, 2 H), 3.91 (s, 2 H), 3.71 (s, 2 H), 3.35 (s, 2 H), 3.30 (s, 2 H), 2.23 (s, 3 H); MS m/z 448 (M+1).

EXAMPLE 54

7-[5-(4-Fluorobenzyl)-4H-1,2,4-triazol-3-yl]-5-(4-pyrazin-2-ylpiperazin-1-yl)-1,6-naphthyridin-8-ol

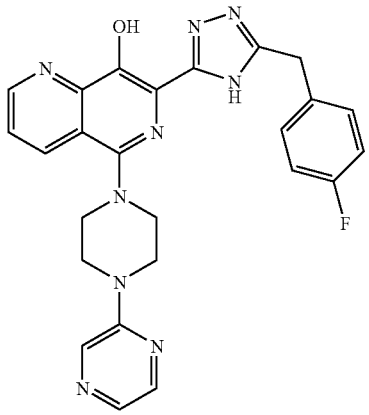

In a similar manner as described in example 17, 7-[5-(4-fluorobenzyl)-4H-1,2,4-triazol-3-yl]-5-(4-pyrazin-2-ylpiperazin-1-yl)-1,6-naphthyridin-8-ol (11 mg, 15%) was prepared as a yellow solid. $^1$H NMR (CDCl$_3$): δ 9.14 (d, J=2.4 Hz, 1 H), 8.48 (d, J=8.4 Hz, 1 H), 8.24 (s, 1 H), 8.13 (s, 1 H), 7.93 (d, J=2.4 Hz, 1 H), 7.58 (dd, J=8.4, 4.0 Hz, 1 H), 7.35 (m, 2 H), 7.00 (m, 2 H), 4.18 (s, 2 H), 3.86 (s, 4 H), 3.42 (s, 4 H); MS m/z 484 (M+1).

EXAMPLE 55

7-[5-(4-Fluorobenzyl)-4H-1,2,4-triazol-3-yl]-5-[4-(2-morpholin-4-yl-2-oxoethyl)piperazin-1-yl]-1,6naphthyridin-8-ol

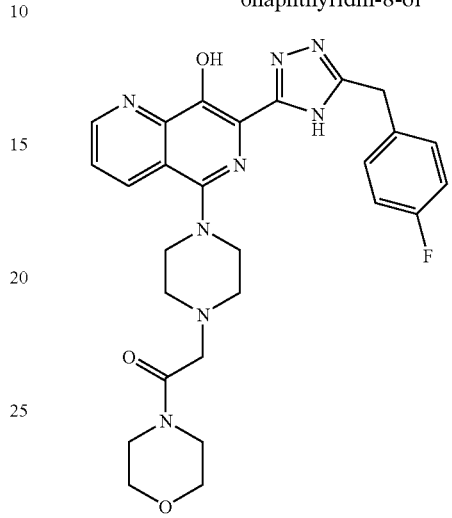

In a similar manner as described in example 17, 7-[5-(4-fluorobenzyl)-4H-1,2,4-triazol-3-yl]-5-[4-(2-morpholin-4-yl-2-oxoethyl)piperazin-1-yl]-1,6-naphthyridin-8-ol (54 mg, 66%) was prepared as the formic acid salt. $^1$H NMR (CDCl$_3$): δ 9.10 (d, J=2.4 Hz, 1 H), 8.48 (d, J=8.4 Hz, 1 H), 7.53 (dd, J=8.4, 4.4 Hz, 1 H), 7.34 (m, 2 H), 6.98 (m, 2 H), 4.17 (s, 2 H), 3.68-3.64 (m, 8 H), 3.34 (s, 6 H), 2.82 (s, 4 H); MS m/z 533 (M+1).

EXAMPLE 56

2-(4-{7-[5-(4-Fluorobenzyl)-4H-1,2,4-triazol-3-yl]-hydroxy-1,6-naphthyridin-5-yl}piperazin-1-yl)-N-isopropylacetamide

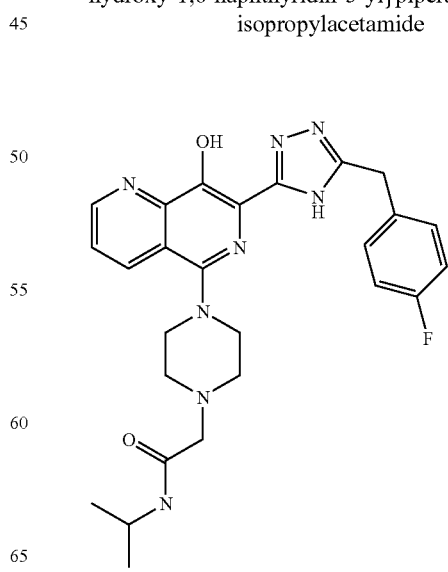

In a similar manner as described in example 17, 2-(4-{7-[5-(4-fluorobenzyl)-4H-1,2,4-triazol-3-yl]-8-hydroxy-1,6-naphthyridin-5-yl}piperazin-1-yl)-N-isopropylacetamide (31 mg, 38%) was prepared as the formic acid. $^1$H NMR (CDCl$_3$): δ 9.13 (d, J=4.0 Hz, 1 H), 8.42 (d, J=8.4 Hz, 1 H), 7.56(dd, J=8.4, 4.0 Hz, 1 H), 7.36 (m, 2 H), 7.02 (m, 2 H), 4.19 (s, 2 H), 4.17-4.13 (m, 1 H), 3.37 (s, 4 H), 3.13 (s, 2 H), 2.82 (s, 4 H), 1.20 (d, J=6.4 Hz, 6 H); MS m/z 505 (M+1).

Examples 57-184 may be prepared by methods described above.

| Example | Name | Structure | Mwt |
|---|---|---|---|
| 57 | 4-[7-(5-Benzyl-1,3,4-oxadiazol-2-yl)-8-hydroxy-1,6-naphthyridin-5-yl]piperazin-2-one | 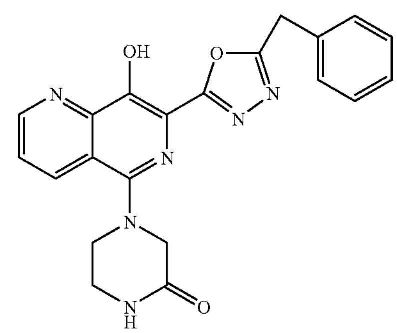 | 402.4 |
| 58 | 5-(4-Acetylpiperazin-1-yl)-7-(5-benzyl-1,3,4-oxadiazol-2-yl)-1,6-naphthyridin-8-ol | 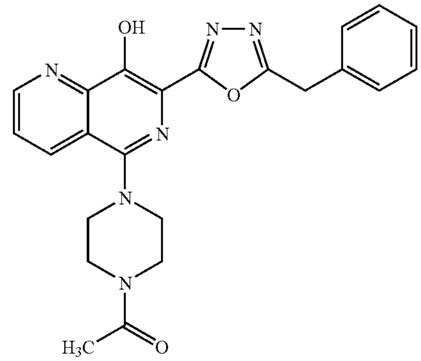 | 430.4 |
| 59 | 7-(5-Benzyl-1,3,4-oxadiazol-2-yl)-5-[4-(2-furoyl)piperazin-1-yl]-1,6-naphthyridin-8-ol | 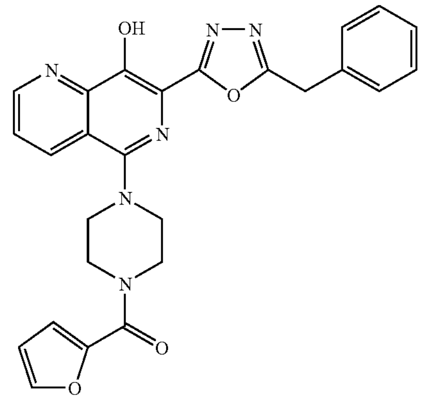 | 482.5 |

| Example | Name | Structure | Mwt |
|---|---|---|---|
| 60 | 7-(5-Benzyl-1,3,4-oxadiazol-2-yl)-5-[4-(2-morpholin-4-yl-2-oxoethyl)piperszin-1-yl]-1,6-naphthyridin-8-ol | 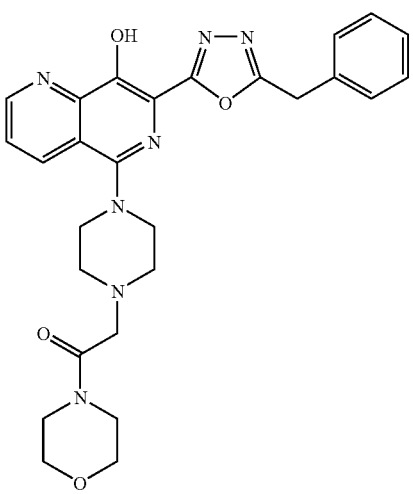 | 515.5 |
| 61 | 2-{4-[7-(5-Benzyl-1,3,4-oxadiazol-2-yl)-8-hydroxy-1,6-naphthyridin-5-yl]piperazin-1-yl}-N-isopropylacetamide | 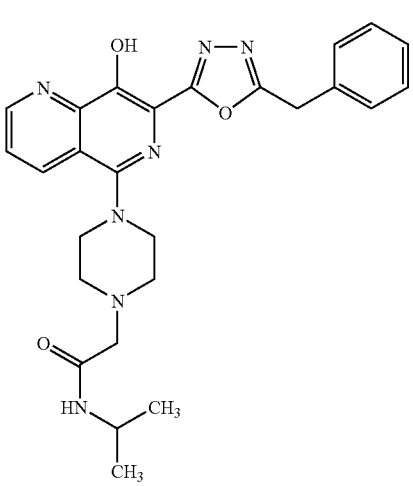 | 487.5 |
| 62 | 2-{4-[7-(5-Anilino-1,3,4-oxadiazol-2-yl)-8-hydroxy-1,6-napthyridin-5-yl]piperazin-1-yl}-N,N-dimethylacetamide | 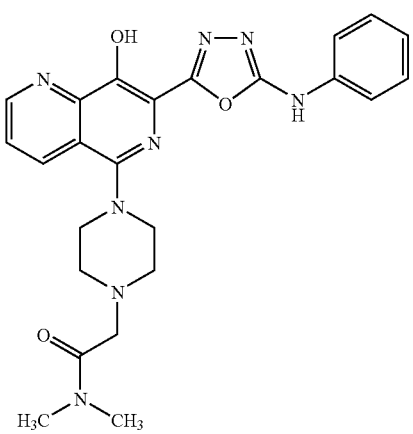 | 474.5 |

-continued

| Example | Name | Structure | Mwt |
|---|---|---|---|
| 63 | 5-{4-[2-(Dimethylamino)ethyl]piperazin-1-yl}-7-[5-(4-fluorobenzyl)-4H-1,2,4-triazol-3-yl]-1,6-naphthyridin-8-ol | 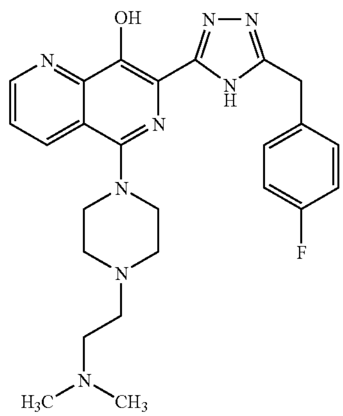 | 522.5 |
| 64 | 2-(4-{7-[5-(4-Fluorobenzyl)-4H-1,2,4-triazol-3-yl]-8-hydroxy-1,6-naphthyridin-5-yl}piperazin-1-yl)-N,N-dimethylacetamide | 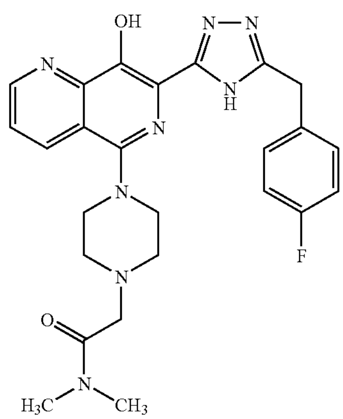 | 490.5 |
| 65 | 4-[7-(5-Anilino-1,3,4-oxadiazol-2-yl)-8-hydroxy-1,6-naphthyridin-5-yl]piperazin-2-one | 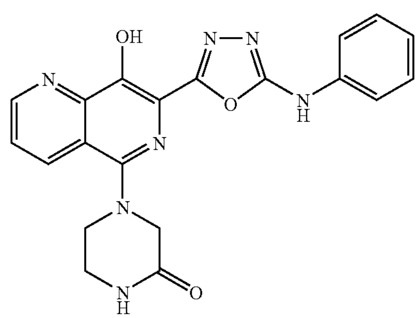 | 403.4 |
| 66 | 7-[3-(4-Fluorobenzyl)-1-methyl-1H-1,2,4-triazol-5-yl]-1,6-naphthyridin-8-ol | 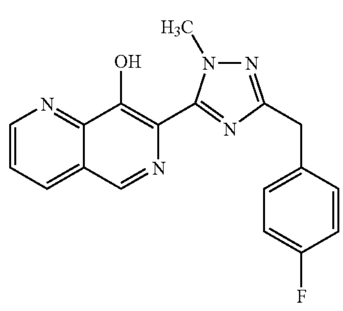 | 335.3 |

-continued

| Example | Name | Structure | Mwt |
|---|---|---|---|
| 67 | 7-[5-(4-Fluorobenzyl)-1-methyl-1H-1,2,4-triazol-3-yl]-1,6-naphthyridin-8-ol | 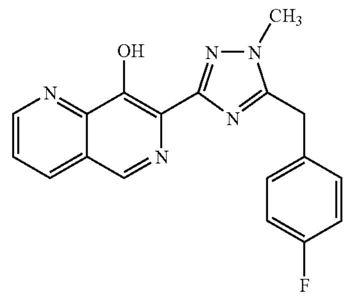 | 335.3 |
| 68 | 7-(5-Benzyl-1,3,4-oxadiazol-2-yl)-5-[4-(2-methoxyethyl)piperazin-1-yl]-1,6-naphthyridin-8-ol | 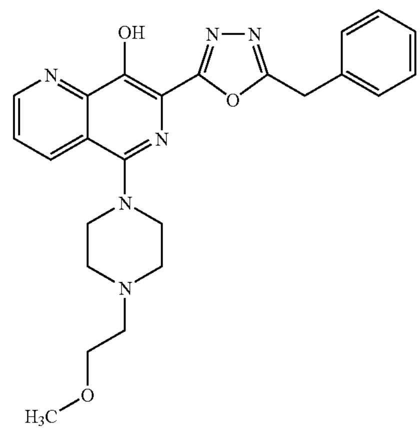 | 446.5 |
| 69 | 2-(4-{7-[5-(4-Fluorobenzyl)-1,3,4-oxadiazol-2-yl]-8-hydroxy-1,6-napthyridin-5-yl}piperazin-1-yl)-N,N-dimethylacetamide | 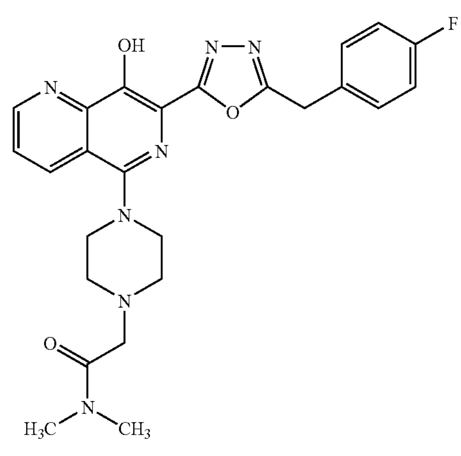 | 491.5 |
| 70 | 7-[5-(4-Fluorobenzyl)-1,3,4-oxadiazol-2-yl]-5-[4-(methylsulfonyl)piperazin-1-yl]-1,6-naphthyridin-8-ol | 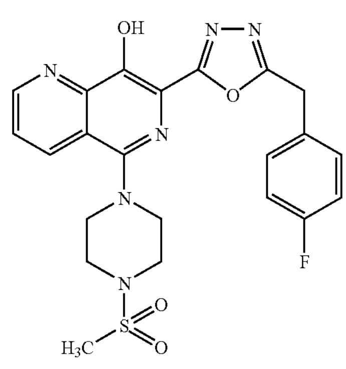 | 484.5 |

-continued

| Example | Name | Structure | Mwt |
|---|---|---|---|
| 71 | 7-[5-(4-Fluorobenzyl)-1,3,4-oxadiazol-2-yl]-5-{4-[(4-methylphenyl)sulfonyl]piperazin-1-yl}-1,6-naphthyridin-8-ol | 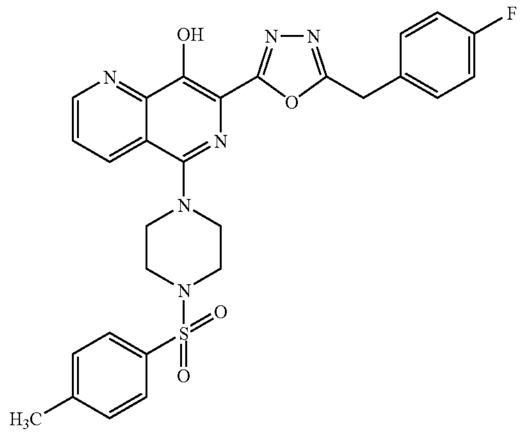 | 560.6 |
| 72 | 7-[5-(4-Fluorobenzyl)-1,3,4-oxadiazol-2-yl]-8-hydroxy-1,6-naphthyridine-5-carbonitrile | 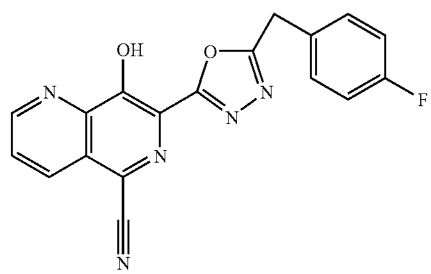 | 347.3 |
| 73 | 4-{7-[5-(4-Fluorobenzyl)-1,3,4-oxadiazol-2-yl]-8-hydroxy-1,6-naphthyridin-5-yl}piperazin-2-one | 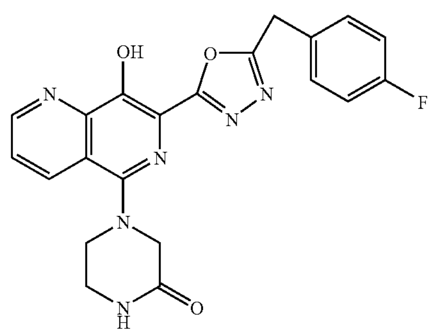 | 420.4 |
| 74 | N-Benzyl-4-{7-[5-(4-fluorobenzyl)-1,3,4-oxadiazol-2-yl]-8-hydroxy-1,6-naphthyridin-5-yl}piperazine-1-carboxamide | 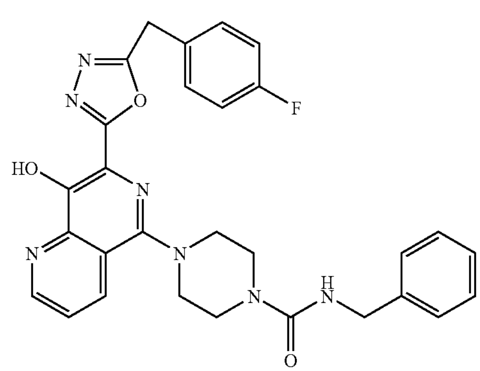 | 539.5 |

-continued

| Example | Name | Structure | Mwt |
|---|---|---|---|
| 75 | 1-{7-[5-(4-Fluorobenzyl)-1,3,4-oxadiazol-2-yl]-8-hydroxy-1,6-naphthyridin-5-yl}piperidin-2-one | 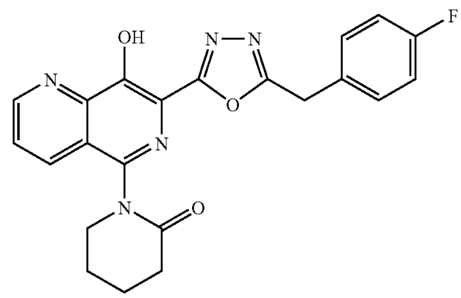 | 419.4 |
| 76 | 1-{7-[5-(4-Fluorobenzyl)-1,3,4-oxadiazol-2-yl]-8-hydroxy-1,6-naphthyridin-5-yl}pyrrolidin-2-one | 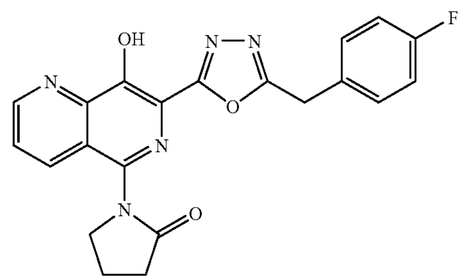 | 405.3 |
| 77 | 7-[5-(4-Fluorobenzyl)-1,3,4-oxadiazol-2-yl]-5-phenyl-1,6-naphthyridin-8-ol | 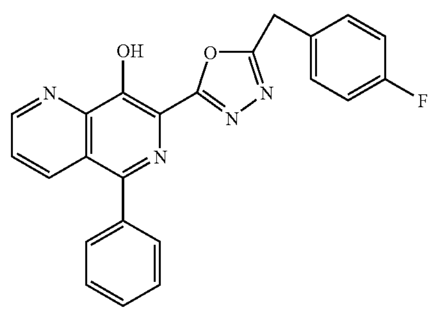 | 398.3 |
| 78 | 1-Ethyl-4-{7-[5-(4-fluorobenzyl)-1,3,4-oxadiazol-2-yl]-8-hydroxy-1,6-naphthyridin-5-yl}piperazine-2,3-dione | 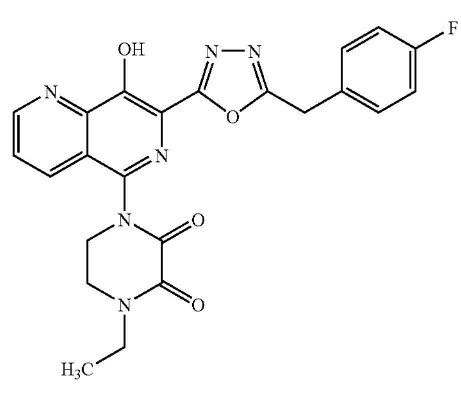 | 462.4 |

-continued

| Example | Name | Structure | Mwt |
|---|---|---|---|
| 79 | N-{7-(5-(4-Fluorobenzyl)-1,3,4-oxadiazol-2-yl]-8-hydroxy-1,6-naphthyridin-5-yl}-4-methylbenzenesulfonamide | 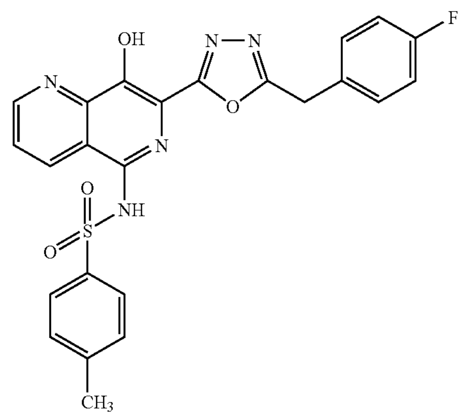 | 491.5 |
| 80 | N-{7-[5-(4-Fluorobenzyl)-1,3,4-oxadiazol-2-yl]-8-hydroxy-1,6-naphthyridin-5-yl)-N-(methylsulfonyl)methanesulfonamide | 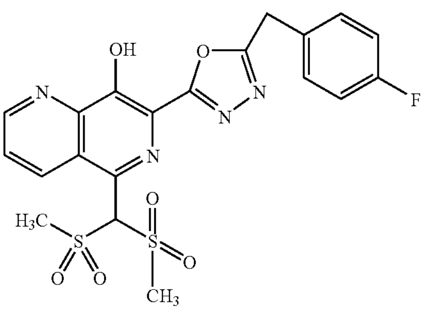 | 493.4 |
| 81 | Ethyl ({7-[5-(4-fluorobenzyl)-1,3,4-oxadiazol-2-yl]-8-hydroxy-1,6-naphthyridin-5-yl}amino)(oxo)acetate | 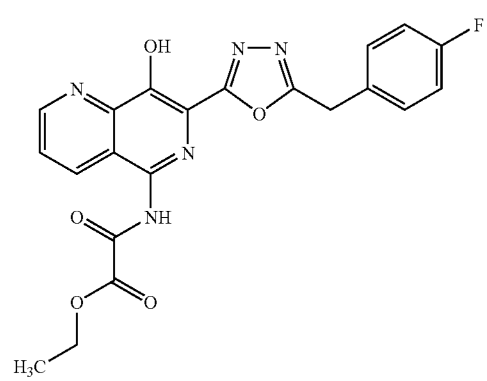 | 437.3 |
| 82 | 7-[5-(4-Fluorobenzyl)-1,3,4-oxadiazol-2-yl]-5-pyridin-3-yl-1,6-naphthyridin-8-ol | 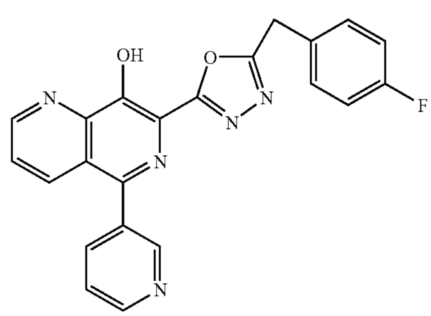 | 399.3 |

| Example | Name | Structure | Mwt |
|---|---|---|---|
| 83 | 7-[5-(4-Fluorobenzyl)-1,3,4-oxadiazol-2-yl]-5-pyridin-4-yl-1,6-naphthyridin-8-ol | 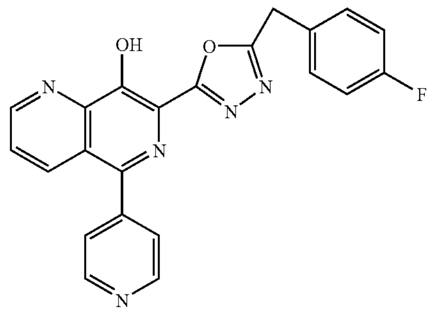 | 399.3 |
| 84 | N-{7-[5-(4-Fluorobenzyl)-1,3,4-oxadiazol-2-yl]-8-hydroxy-1,6-naphthyridin-5-yl}acetamide | 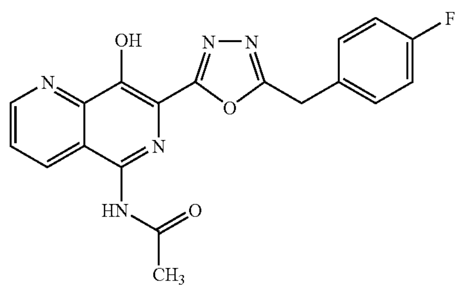 | 379.3 |
| 85 | Benzyl 4-{7-[5-(4-fluorobenzyl)-1,3,4-oxadiazol-2-yl]-8-hydroxy-1,6-naphthyridin-5-yl}-3-oxopiperazine-1-carboxylate | 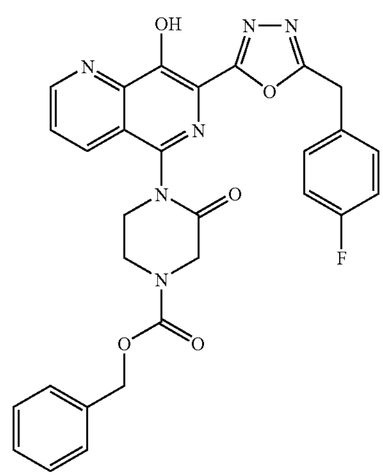 | 554.5 |
| 86 | N-{7-[5-(4-Fluorobenzyl)-1,3,4-oxadiazol-2-yl]-8-hydroxy-1,6-naphthyridin-5-yl}methanesulfonamide | 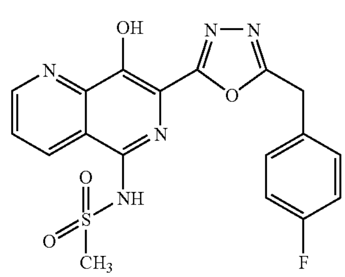 | 415.4 |

-continued

| Example | Name | Structure | Mwt |
|---|---|---|---|
| 87 | 7-[5-(4-Fluorobenzyl)-1,3,4-oxadiazol-2-yl]-8-hydroxy-1,6-naphthyridine-5-carboxylic acid | 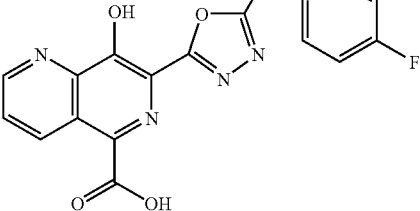 | 366.3 |
| 88 | 1-{7-[5-(4-Fluorobenzyl)-1,3,4-oxadiazol-2-yl]-8-hydroxy-1,6-naphthyridin-5-yl}azepan-2-one | 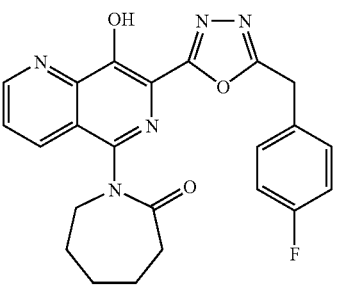 | 433.4 |
| 89 | 3-{7-[5-(4-Fluorobenzyl)-1,3,4-oxadiazol-2-yl]-8-hydroxy-1,6-naphthyridin-5-yl}benzoic acid | 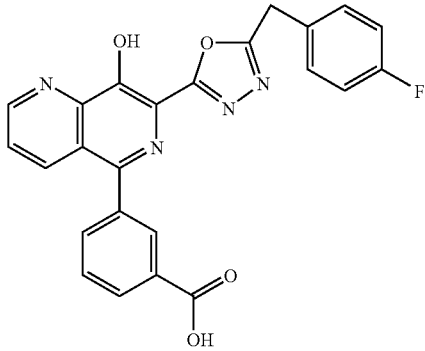 | 442.4 |
| 90 | 5-(1,1-Dioxidoisothiazolidin-2-yl)-7-[5-(4-fluorobenzyl)-1,3,4-oxadiazol-2-yl]-1,6-naphthyridin-8-ol | 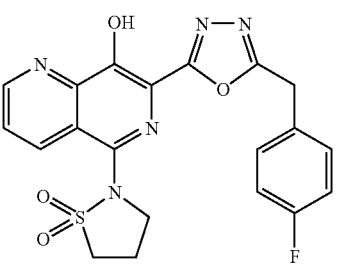 | 441.4 |
| 91 | 2-(4-{7-[5-(4-Fluorobenzyl)-1,3,4-oxadiazol-2-yl]-8-hydroxy-1,6-naphthyridin-5-yl}-3-oxopiperazin-1-yl)-N,N-dimethylacetamide | 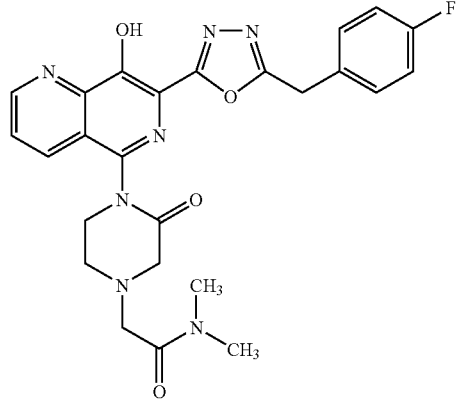 | 505.5 |

| Example | Name | Structure | Mwt |
|---|---|---|---|
| 92 | 1-{7-[5-(4-Fluorobenzyl)-1,3,4-oxadiazol-2-yl]-8-hydroxy-1,6-naphthyridin-5-yl}-3-methylimidazolidin-2-one | 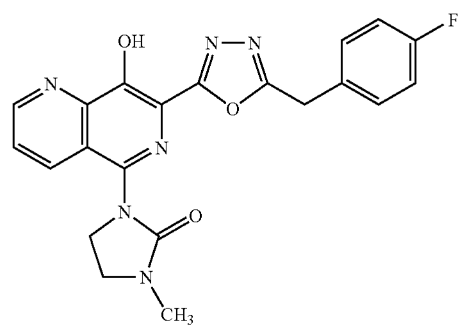 | 420.4 |
| 93 | 5-(3-Aminophenyl)-7-[5-(4-fluorobenzyl)-1,3,4-oxadiazol-2-yl]-1,6-naphthyrldin-8-ol | 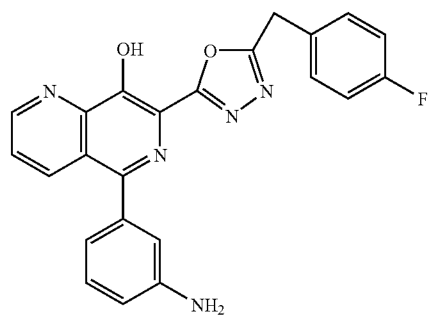 | 413.4 |
| 94 | 3-{7-[5-(4-Fluorobenzyl)-1,3,4-oxadiazol-2-yl]-8-hydroxy-1,6-naphthyridin-5-yl}-N-isopropylbenzamide | 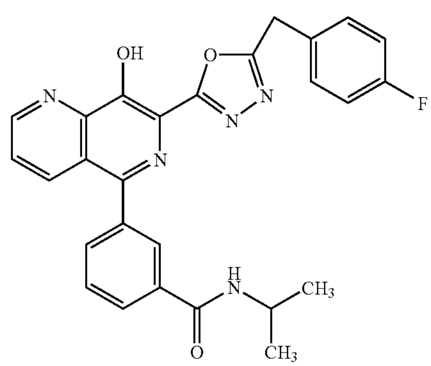 | 483.5 |
| 95 | N-(3-{7-[5-(4-Fluorobenzyl)-1,3,4-oxadiazol-2-yl]-8-hydroxy-1,6-naphthyridin-5-yl}phenyl)acetamide | 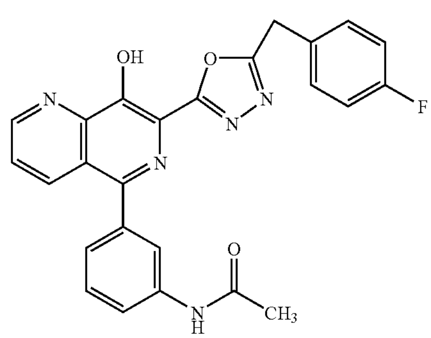 | 455.4 |

-continued

| Example | Name | Structure | Mwt |
|---|---|---|---|
| 96 | 4-{7-[5-(4-fluorobenzyl)-1,3,4-oxadiazol-2-yl]-8-hydroxy-1,6-naphthyridin-5-yl}benzoic acid | 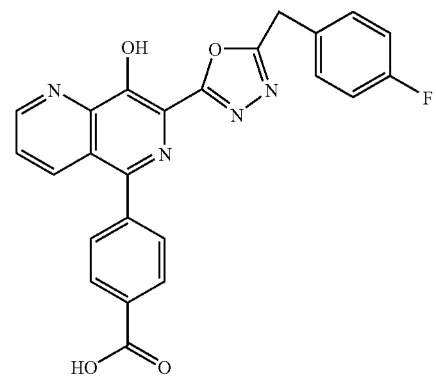 | 442.41 |
| 97 | 3-{7-[5-(4-fluorobenzyl)-1,3,4-oxadiazol-2-yl]-8-hydroxy-1,6-naphthyridin-5-yl}-1,3-oxazolidin-2-one | 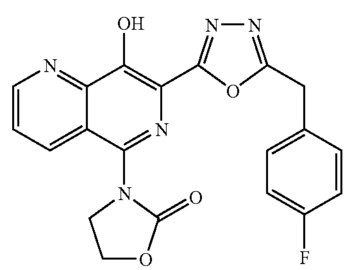 | 407.364 |
| 98 | N-{7-[5-(4-fluorobenzyl)-1,3,4-oxadiazol-2-yl]-8-hydroxy-1,6-naphthyridin-5-yl}-5-methylpyridine-2-sulfonamide | 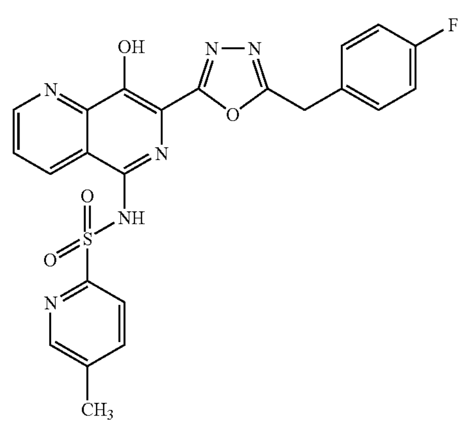 | 492.492 |
| 99 | 7-[5-(4-fluorobenzyl)-1,3,4-oxadiazol-2-yl]-5-(3-furyl)-1,6-naphthyridin-8-ol | 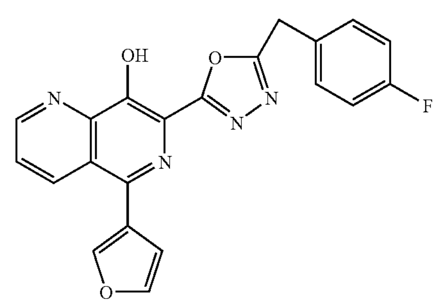 | 388.361 |

-continued

| Example | Name | Structure | Mwt |
|---|---|---|---|
| 100 | 4-{7-[5-(4-fluorobenzyl)-1,3,4-oxadiazol-2-yl]-8-hydroxy-1,6-naphthyridin-5-yl}-N,N-dimethylbenzamide | 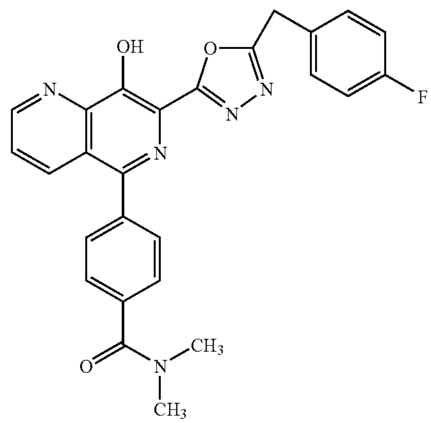 | 469.479 |
| 101 | 4-{7-[5-(4-fluorobenzyl)-1,3,4-oxadiazol-2-yl]-4-hydroxy-1,6-naphthyridin-5-yl}-N,N-dimethyl-3-oxopiperazine-1-carboxamide | 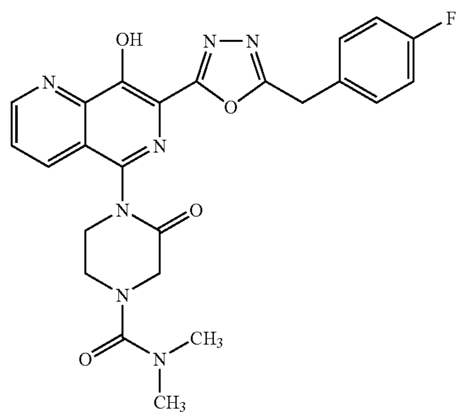 | 491.486 |
| 102 | 4-{7-[5-(4-fluorobenzyl)-1,3,4-oxadiazol-2-yl]-8-hydroxy-1,6-naphthyridin-5-yl}-N-isopropylbenzamide | 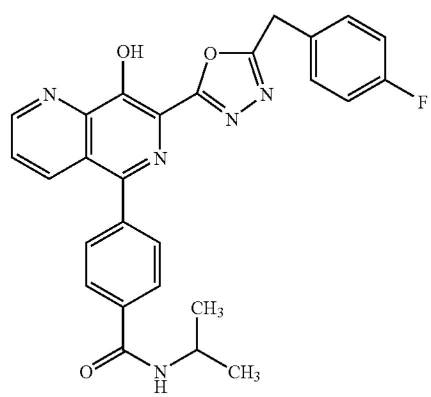 | 483.506 |
| 103 | 4-acetyl-1-{7-[5-(4-fluorobenzyl)-1,3,4-oxadiazol-2-yl]-8-hydroxy-1,6-naphthyridin-5-yl}piperazin-2-one | 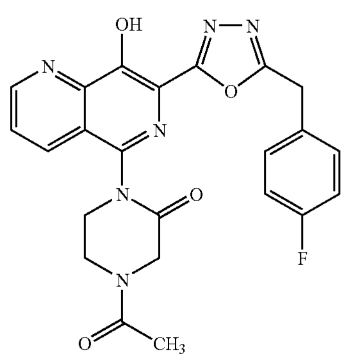 | 462.444 |

-continued

| Example | Name | Structure | Mwt |
|---|---|---|---|
| 104 | 7-[5-(4-fluorobenzyl)-1,3,4-oxadiazol-2-yl]-5-(1H-pyrazol-4-yl)-1,6-naphthyridin-8-ol | 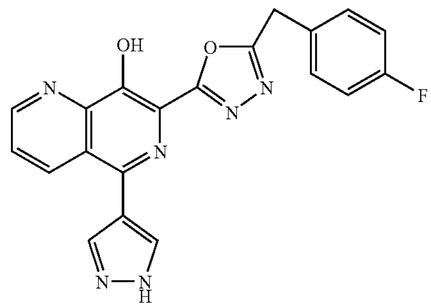 | 388.364 |
| 105 | 5-(3,5-dimethylisoxazol-4-yl)-7-[5-(4-fluorobenzyl)-1,3,4-oxadiazol-2-yl]-1,6-naphthyridin-8-ol | 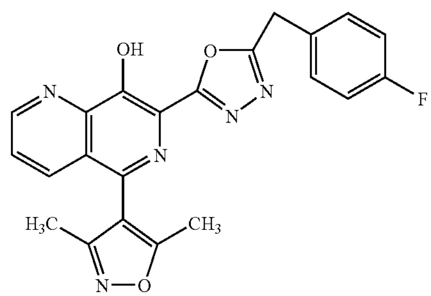 | 417.403 |
| 106 | 7-[5-(4-fluorobenzyl)-1,3,4-oxadiazol-2-yl]-5-pyridin-2-yl-1,6-naphthyridin-8-ol | 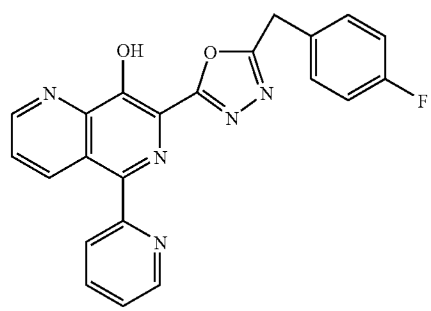 | 399.388 |
| 107 | 1-{7-[5-(4-fluorobenzyl)-1,3,4-oxadiazol-2-yl]-8-hydroxy-1,6-naphthyridin-5-yl}piperazin-2-one | 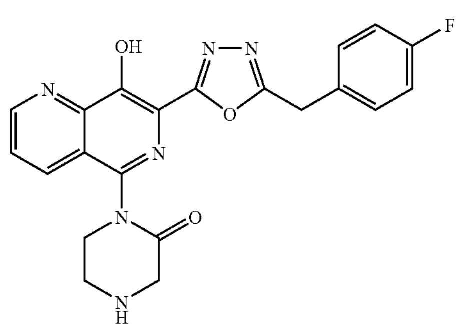 | 420.406 |
| 108 | N-(3-{7-[5-(4-fluorobenzyl)-1,3,4-oxadiazol-2-yl]-8-hydroxy-1,6-naphthyridin-5-yl}phenyl)methanesulfonamide | 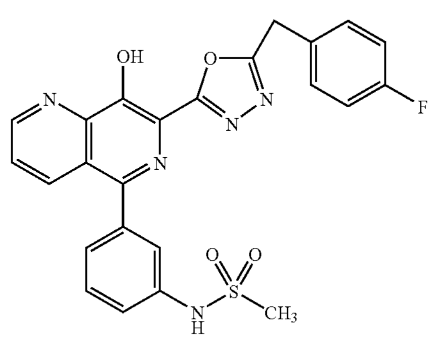 | 491.504 |

-continued

| Example | Name | Structure | Mwt |
|---|---|---|---|
| 109 | N-(3-{7-[5-(4-fluorobenzyl)-1,3,4-oxadiazol-2-yl]-8-hydroxy-1,6-naphthyridin-5-yl}phenyl)urea | 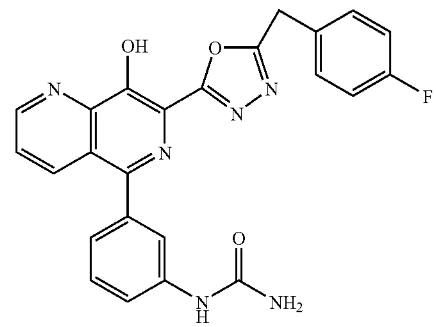 | 456.44 |
| 110 | N-{7-[5-(4-fluorobenzyl)-1,3,4-oxadiazol-2-yl]-8-hydroxy-1,6-naphthyridin-5-yl}pentanamide | 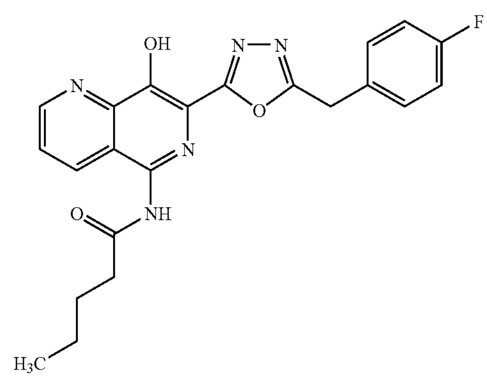 | 421.435 |
| 111 | 7-[5-(4-fluorobenzyl)-1,3,4-oxadiazol-2-yl]-5-(1H-pyrrol-2-yl)-1,6-naphthyridin-8-ol | 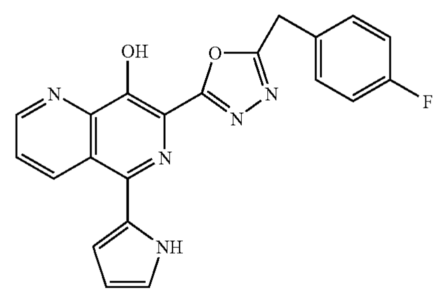 | 387.376 |
| 112 | 1-{7-[5-(4-fluorobenzyl)-1,3,4-oxadiazol-2-yl]-8-hydroxy-1,6-naphthyridin-5-yl}-4-(methylsulfonyl)piperazin-2-one | 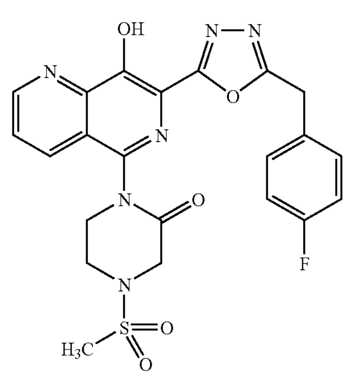 | 498.496 |

-continued

| Example | Name | Structure | Mwt |
|---|---|---|---|
| 113 | 7-[5-(4-fluorobenzyl)-1,3,4-oxadiazol-2-yl]-5-pyrazin-2-yl-1,6-naphthyridin-8-ol | 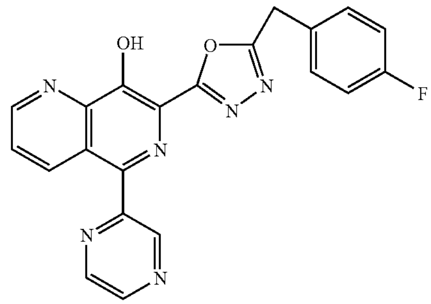 | 400.375 |
| 114 | 7-[5-(4-fluorobenzyl)-1,3,4-oxadiazol-2-yl]-5-(1,3-thiazol-2-yl)-1,6-naphthyridin-8-ol | 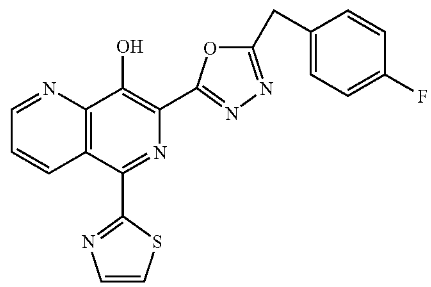 | 405.413 |
| 115 | N-(3-{7-[5-(4-fluorobenzyl)-1,3,4-oxadiazol-2-yl]-8-hydroxy-1,6-naphthyridin-5-yl}phenyl)-N'-isopropylurea | 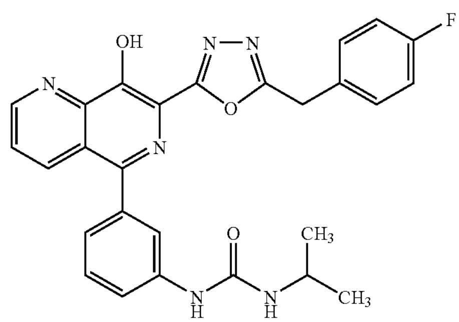 | 498.521 |
| 116 | N-(4-{7-[5-(4-fluorobenzyl)-1,3,4-oxadiazol-2-yl]-8-hydroxy-1,6-naphthyridin-5-yl}phenyl)acetamide | 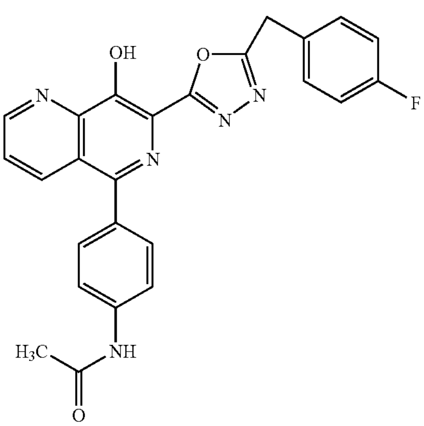 | 455.452 |

| Example | Name | Structure | Mwt |
|---|---|---|---|
| 117 | N~2~-acetyl-N~1~-(1-(N-acetylglycyl)-4-{7-[5-(4-fluorobenzyl)-1,3,4-oxadiazol-2-yl]-8-hydroxy-1,6-naphthyridin-5-yl}-3-oxopiperazin-2-yl)-N~1~-(1-(N-acetylglycyl)-4-{7-[5-(4-fluorobenzyl)-1,3,4-oxadiazol-2-yl]-8-hydroxy-1,6-naphthyridin-5-yl}-5-oxopiperazin-2-yl)glycinamide | 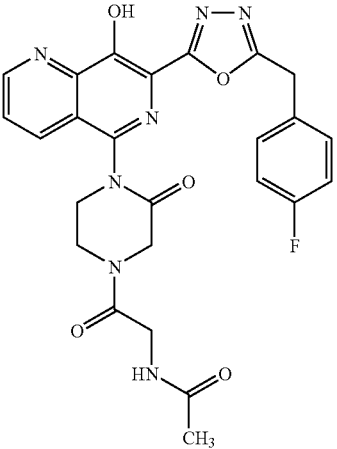 | 519.496 |
| 118 | methyl 3-(acetylamino)-5-{7-[5-(4-fluorobenzyl)-1,3,4-oxadiazol-2-yl]-8-hydroxy-1,6-naphthyridin-5-yl}benzoate | 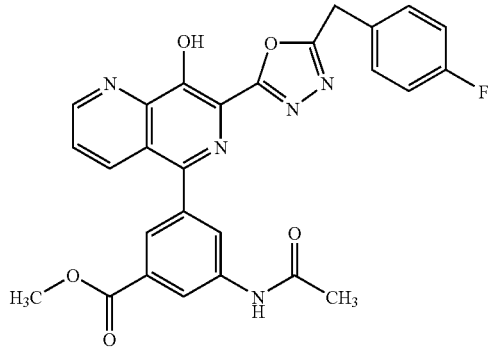 | 513.489 |
| 119 | 1-{7-[5-(4-fluxorobenzyl)-1,3,4-oxadiazol-2-yl]-8-hydroxy-1,6-naphthyridin-5-yl}tetrahydropyrimidin-2(1H)-one | 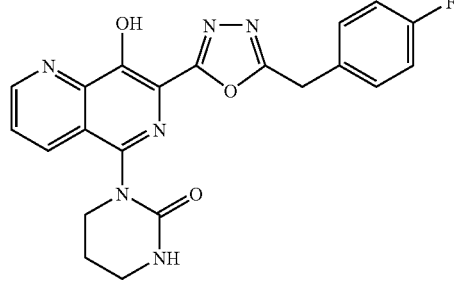 | 420.406 |
| 120 | N'-{7-[5-(4-fluorobenzyl)-1,3,4-oxadiazol-2-yl]-8-hydroxy-1,6-naphthyridin-5-yl}-N,N-dimethylsulfamide | 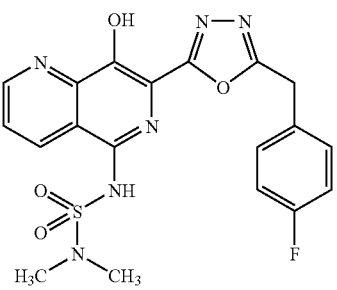 | 444.448 |

-continued

| Example | Name | Structure | Mwt |
|---|---|---|---|
| 121 | 1-{7-[5-(4-fluorobenzyl)-1,3,4-oxadiazol-2-yl]-8-hydroxy-1,6-naphthyridin-5-yl}imidazolidin-2-one | 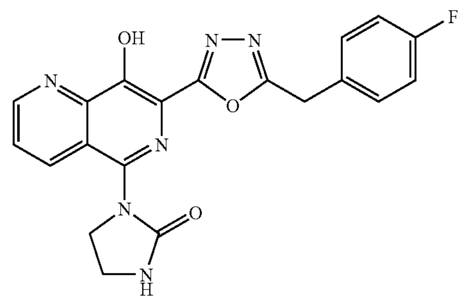 | 406.379 |
| 122 | 1-(3-{7-[5-(4-fluorobenzyl)-1,3,4-oxadiazol-2-yl]-8-hydroxy-1,6-naphthyridin-5-yl}phenyl)ethanone | 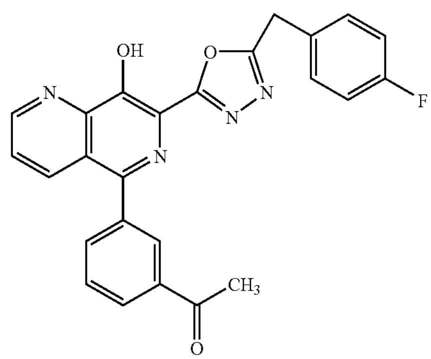 | 440.438 |
| 123 | 7-[5-(4-fluorobenzyl)-1,3,4-oxadiazol-2-yl]-5-(6-methyl-1,1-dioxido-1,2,6-thiadiazinan-2-yl)-1,6-naphthyridin-8-ol | 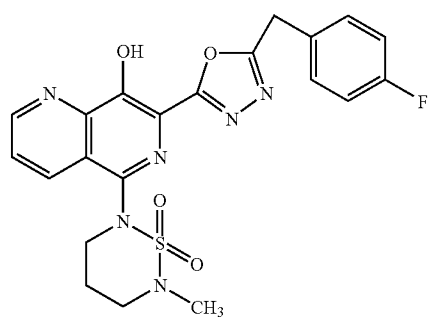 | 470.486 |
| 124 | 7-[5-(4-fluorobenzyl)-1,3,4-oxadiazol-2-yl]-5-(5-methyl-1,1-1,6-naphthyridin-8-ol | 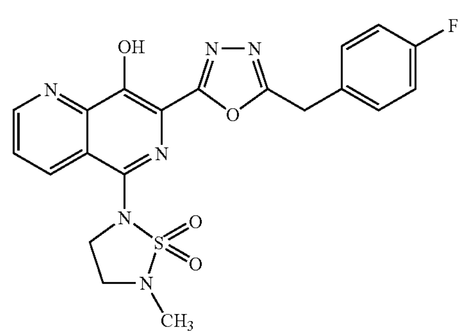 | 456.459 |

-continued

| Example | Name | Structure | Mwt |
|---|---|---|---|
| 125 | 7-[5-(4-fluorobenzyl)-1,3,4-oxadiazol-2-yl]-5-[4-(methylthio)phenyl]-1,6-naphthyridln-8-ol | 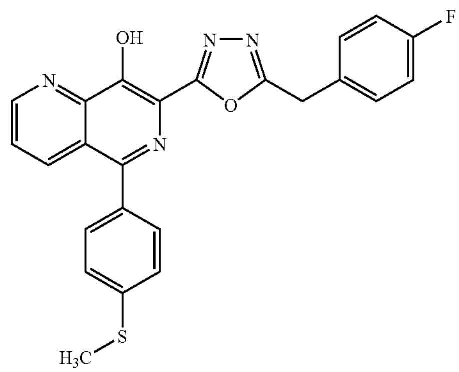 | 444.491 |
| 126 | 7-[5-(4-fluorobenzyl)-1,3,4-oxadiazol-2-yl]-5-[2-(methylsulfonyl)phenyl]-1,6-naphthyridin-8-ol | 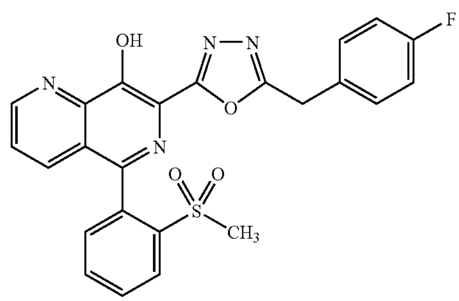 | 476.49 |
| 127 | 7-[5-(4-fluorobenzyl)-1,3,4-oxadiazol-2-yl]-5-[3-(methylsulfonyl)phenyl]-1,6-naphthyridin-8-ol | 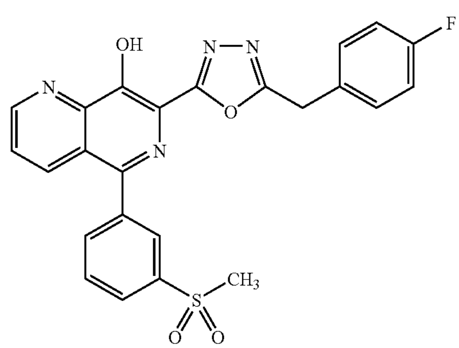 | 476.49 |
| 128 | 7-[5-(4-fluorobenzyl)-1,3,4-oxadiazol-2-yl]-5-[4-(methylsulfonyl)phenyl]-1,6-naphthyridin-8-ol | 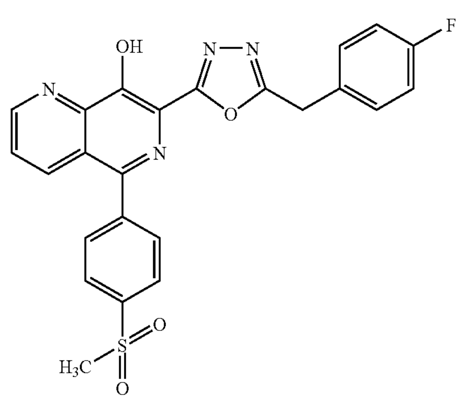 | 476.49 |

| Example | Name | Structure | Mwt |
|---|---|---|---|
| 129 | 1-{7-[5-(4-fluorobenzyl)-1,3,4-oxadiazol-2-yl]-8-hydroxy-1,6-naphthyridin-5-yl}-3-(2-hydroxyethyl)imidazolidin-2-one | 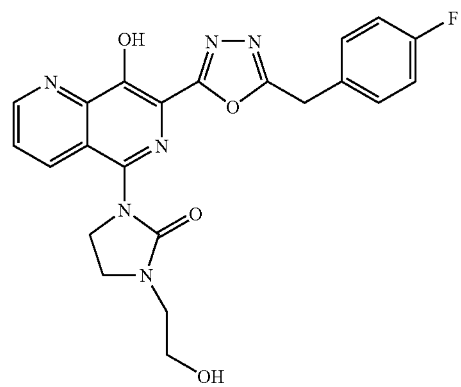 | 450.433 |
| 130 | 7-[5-(4-fluorobenzyl)-1,3,4-oxadiazol-2-yl]-5-[3-(methylthio)phenyl]-1,6-naphthyridin-8-ol | 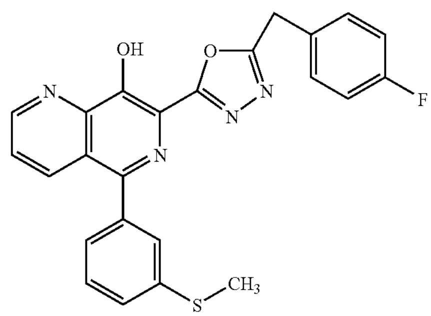 | 444.491 |
| 131 | 7-[5-(4-fluorobenzyl)-1,3,4-oxadiazol-2-yl]-5-[2-(methylthio)phenyl]-1,6-naphthyridin-8-ol | 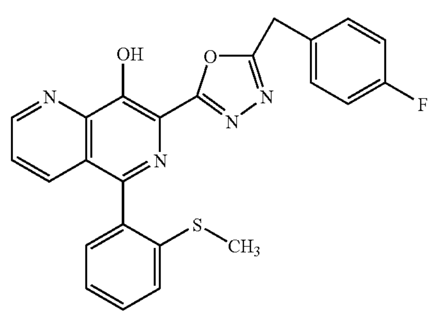 | 444.491 |
| 132 | 7-[5-(4-fluorobenzyl)-1,3,4-oxadiazol-2-yl]-5-(1H-pyrrol-1-yl)-1,6-napbthyridin-8-ol | 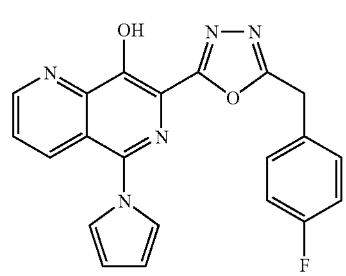 | 387.376 |

-continued

| Example | Name | Structure | Mwt |
|---|---|---|---|
| 133 | N-(4-{7-[5-(4-fluorobenzyl)-1,3,4-oxadiazol-2-yl]-8-hydroxy-1,6-naphthyridin-5-yl}phenyl)methanesulfonamide | 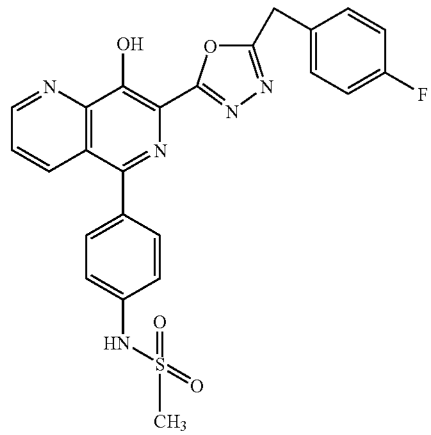 | 491.504 |
| 134 | 4-{7-[5-(4-fluorobenzyl)-1,3,4-oxadiazol-2-yl]-8-hydroxy-1,6-naphthyridin-5-yl}-N,N-dimethylbenzenesulfonamide | 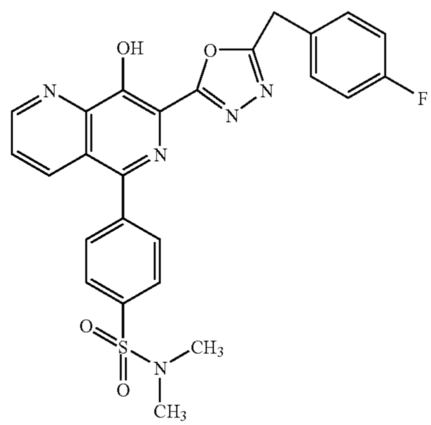 | 505.531 |
| 135 | 2-{7-[5-(4-fluorobenzyl)-1,3,4-oxadiazol-2-yl]-8-hydroxy-1,6-naphthyridin-5-yl}-N-isopropylbenzenesulfonamide | 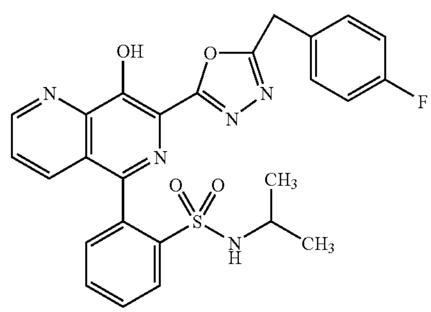 | 519.559 |
| 136 | 4-{7-[5-(4-fluorobenzyl)-1,3,4-oxadiazol-2-yl]-8-hydroxy-1,6-naphthyridin-5-yl}benzonitrile | 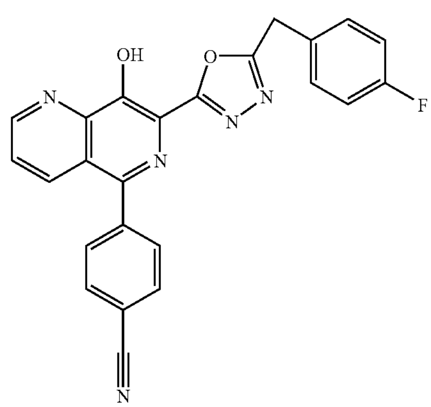 | 423.41 |

-continued

| Example | Name | Structure | Mwt |
|---|---|---|---|
| 137 | 4-{7-[5-(4-fluorobenzyl)-1,3,4-oxadiazol-2-yl]-8-hydroxy-1,6-naphthyridin-5-yl}-N-isopropylbenzenesulfonamide | 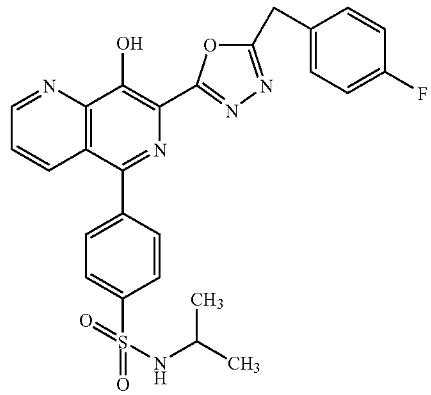 | 519.559 |
| 138 | 2-{7-[5-(4-fluorobenzyl)-1,3,4-oxadiazol-2-yl]-8-hydroxy-1,6-naphthyridin-5-yl}-N,N-dimethylbeuzenesulfonamide | 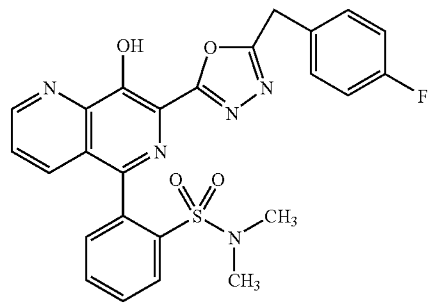 | 505.531 |
| 139 | N-(4-{7-[5-(4-fluorobenzyl)-1,3,4-oxadiazol-2-yl]-8-hydroxy-1,6-naphthyridin-5-yl}phenyl)cyclopropanecarboxamide | 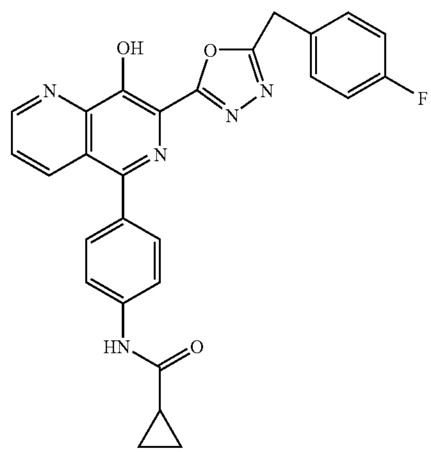 | 481.49 |
| 140 | 7-[5-(4-fluorobenzyl)-1,3,4-oxadiazol-2-yl]-5-(3-methyl-1H-pyrazol-1-yl)-1,6-naphthyridin-8-ol | 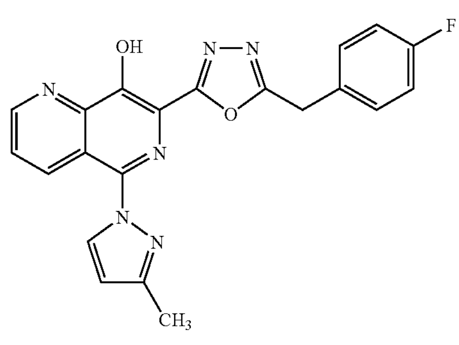 | 402.391 |

-continued

| Example | Name | Structure | Mwt |
|---|---|---|---|
| 141 | N-(4-{7-[5-(4-fluorobenzyl)-1,3,4-oxadiazol-2-yl]-8-hydroxy-1,6-naphthyridin-5-yl}phenyl)propanamide | 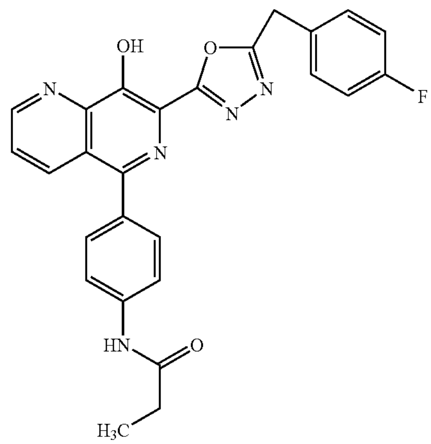 | 469.479 |
| 142 | 4-{7-[5-(4-fluorobenzyl)-1,3,4-oxadiazol-2-yl]-8-hydroxy-1,6-naphthyridin-5-yl}-N-methylbenzamide | 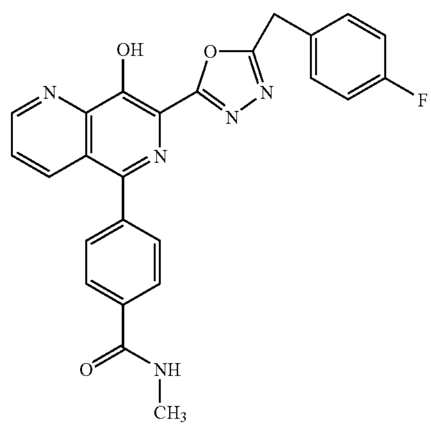 | 455.452 |
| 143 | N-cyclopropyl-4-{7-[5-(4-fluorobenzyl)-1,3,4-oxadiazol-2-yl]-8-hydroxy-1,6-naphthyridin-5-yl}benzamide | 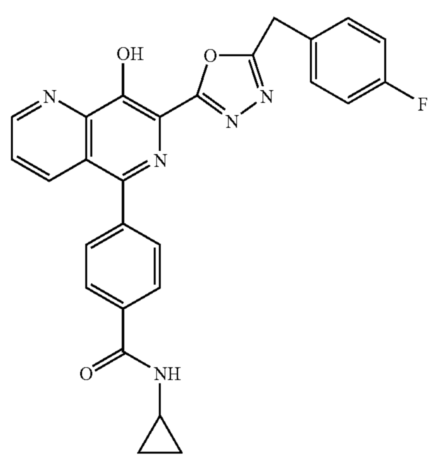 | 481.49 |

-continued
| Example | Name | Structure | Mwt |
|---|---|---|---|
| 145 | 3-(4-fluorobenzyl)-7-[5-(4-fluorobenzyl)-1,3,4-oxadiazol-2-yl]-1,6-naphthyridin-8-ol | 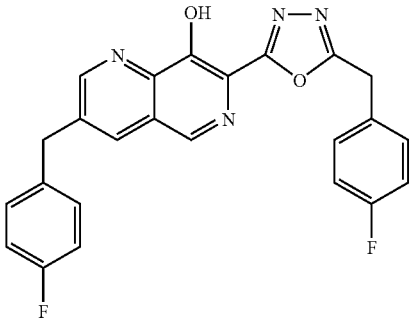 | 430.417 |
| 146 | N-(4-{7-[5-(4-fluorobenzyl)-1,3,4-naphthyridin-5-yl}phenyl)-N'-methylurea | 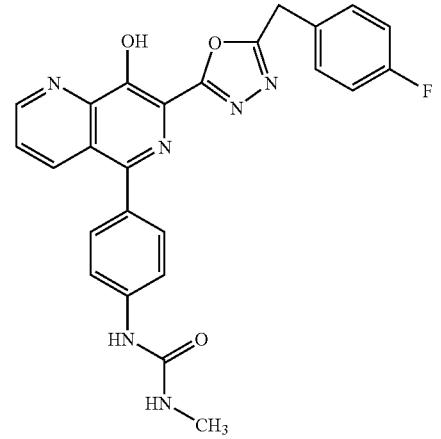 | 470.467 |
| 147 | N'-(4-{7-[5-(4-fluorobenzyl)-1,3,4-oxadiazol-2-yl]-8-hydroxy-1,6-naphthyridin-5-yl}phenyl)-N,N-dimethylurea | 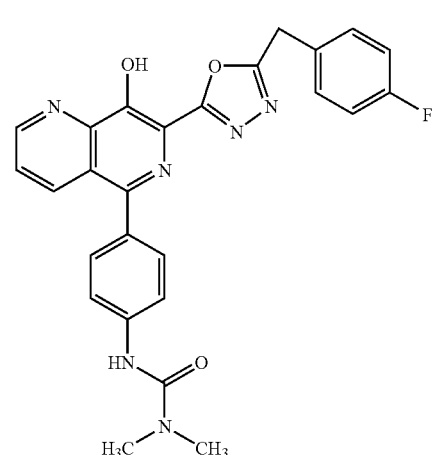 | 484.494 |

-continued

| Example | Name | Structure | Mwt |
|---|---|---|---|
| 148 | 3-{7-[5-(4-fluorobenzyl)-1,3,4-oxadiazol-2-yl]-8-hydroxy-1,6-naphthyridin-5-yl}-N-methylbenzenesulfonamide | 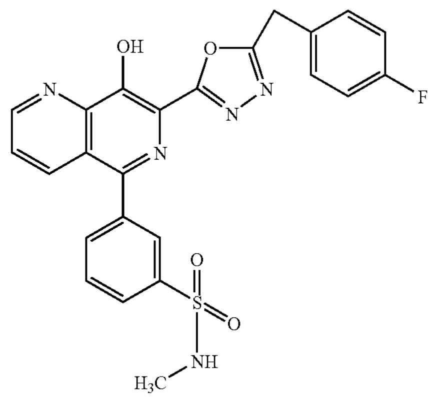 | 491.504 |
| 149 | 4-{7-[5-(4-fluorobenzyl)-1,3,4-oxadiazol-2-yl]-8-hydroxy-1,6-naphthyridin-5-yl}benzamide | 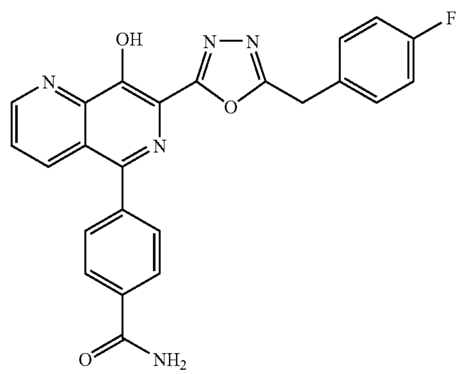 | 441.425 |
| 150 | N-(4-{7-[5-(4-fluorobenzyl)-1,3,4-oxadiazol-2-yl]-8-hydroxy-1,6-naphthyridin-5-yl}phenyl)urea | 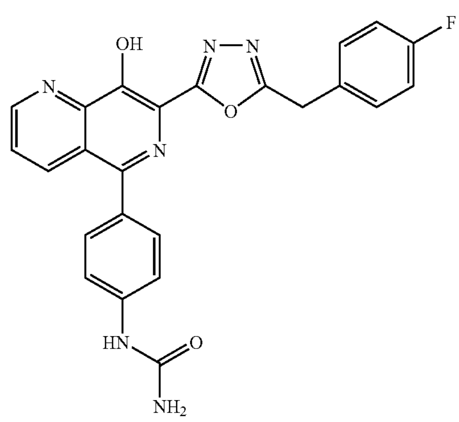 | 456.44 |
| 151 | N-{7-[5-(4-fluorobenzyl)-1,3,4-oxadiazol-2-yl]-8-hydroxy-1,6-naphthyridin-5-yl}cyclopropanecarboxamide | 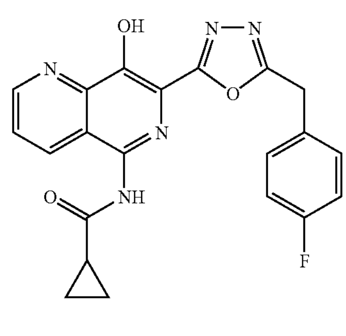 | 405.392 |

| Example | Name | Structure | Mwt |
|---|---|---|---|
| 152 | 7-[5-(4-fluorobenzyl)-1,3,4-oxadiazol-2-yl]-8-hydroxy-1,6-naphthyridine-5-carboxamide | 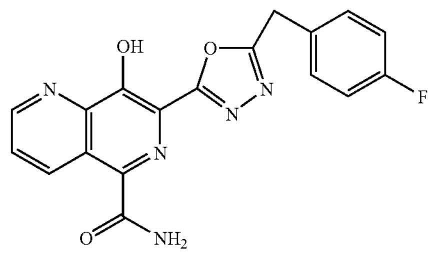 | 365.326 |
| 153 | N-{7-[5-(4-fluorobenzyl)-1,3,4-oxadiazol-2-yl]-8-hydroxy-1,6-naphthyridin-5-yl}-N-methylacetamide | 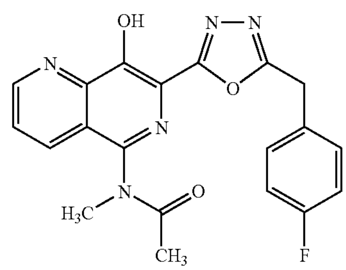 | 393.381 |
| 154 | N-{7-[5-(4-fluorobenzyl)-1,3,4-oxadiazol-2-yl]-8-hydroxy-1,6-naphthyridin-5-yl}-N-methylacetamide | 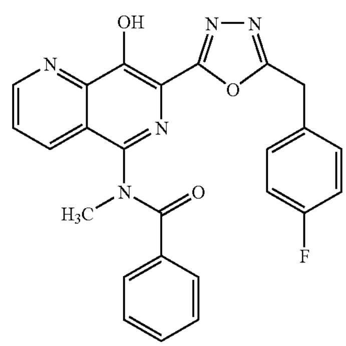 | 455.452 |
| 155 | N-{7-[5-(4-fluorobenzyl)-1,3,4-oxadiazol-2-yl]-8-hydroxy-1,6-naphthyridin-5-yl}butanamide | 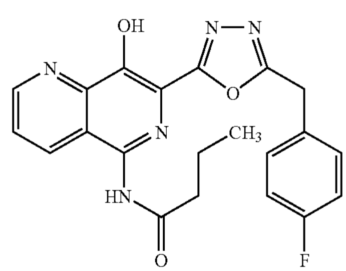 | 407.408 |
| 156 | N-{7-[5-(4-fluorobenzyl)-1,3,4-oxadiazol-2-yl]-8-hydroxy-1,6-naphthyridin-5-yl}propanamide | 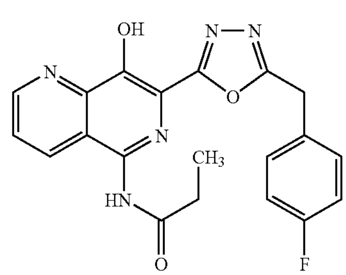 | 393.38 |

-continued

| Example | Name | Structure | Mwt |
|---|---|---|---|
| 157 | 5-[3,5-bis(trifluoromethyl)phenyl]-7-[5-(4-fluorobenzyl)-1,3,4-oxadiazol-2-yl]-1,6-naphthyridin-8-ol | 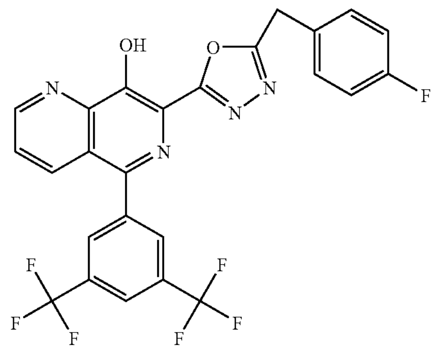 | 534.397 |
| 158 | 5-(4-chlorophenyl)-7-[5-(4-fluorobenzyl)-1,3,4-oxadiazol-2-yl]-1,6-naphthyridin-8-ol | 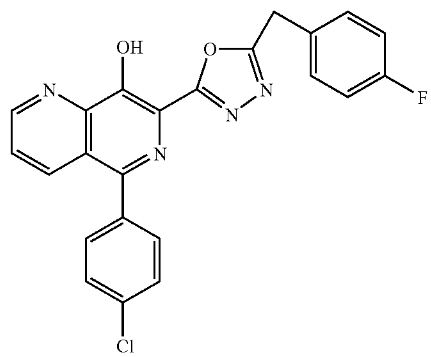 | 432.845 |
| 159 | 7-[5-(4-fluorobenzyl)-1,3,4-oxadiazol-2-yl]-5-[4-(trifluoromethoxy)phenyl]-1,6-naphthyridin-8-ol | 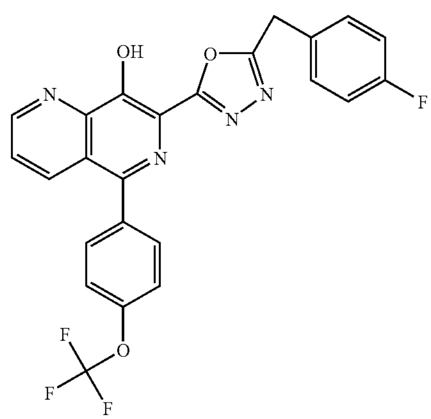 | 482.398 |
| 160 | N-{7-[5-(4-fluorobenzyl)-1,3,4-oxadiazol-2-yl]-8-hydroxy-1,6-naphthyridin-5-yl}-3-methylbutanamide | 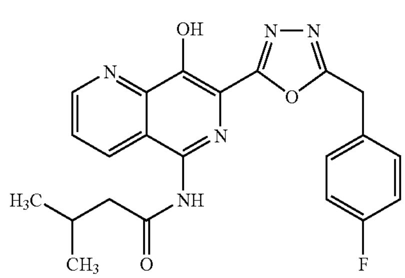 | 421.435 |

-continued

| Example | Name | Structure | Mwt |
|---|---|---|---|
| 161 | N-{7-[5-(4-fluorobenzyl)-1,3,4-oxadiazol-2-yl]-8-hydroxy-1,6-naphthyridin-5-yl)-2-propylpentanamide | 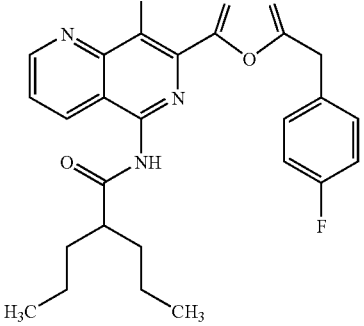 | 463.516 |
| 162 | 7-[5-(4-fluorobenzyl)-1,3,4-oxadiazol-2-yl]-8-hydroxy-N-methyl-1,6-naphthyridine-5-carboxamide | 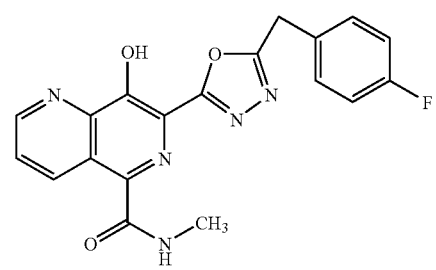 | 379.353 |
| 163 | 7-[5-(4-fluorobenzyl)-1,3,4-oxadiazol-4-yl]-5-(morpholin-4-ylcarbonyl)-1,6-naphthyridin-8-ol | 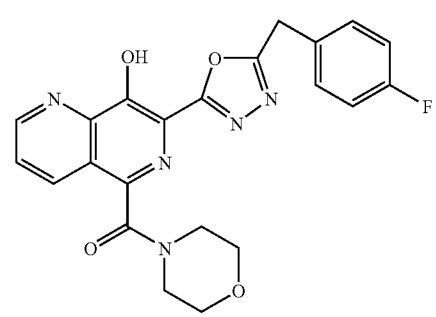 | 435.418 |
| 164 | N'-acetyl-7-[5-(4-fluorobenzyl)-1,3,4-oxadiazol-2-yl]-8-hydroxy-1,6-naphthyridine-5-carbohydrazide | 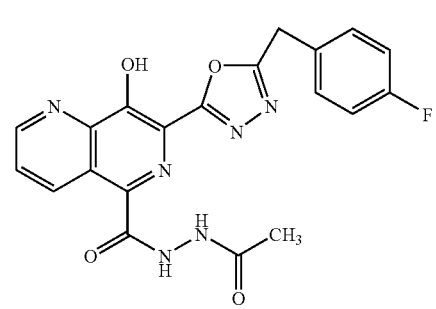 | 422.379 |
| 165 | N-{7-[5-(4-fluorobenzyl)-1,3,4-oxadiazol-2-yl]-8-hydroxy-1,6-naphthyridin-5-yl}-2-(2-oxopyrrolidin-1-yl)acetamide | 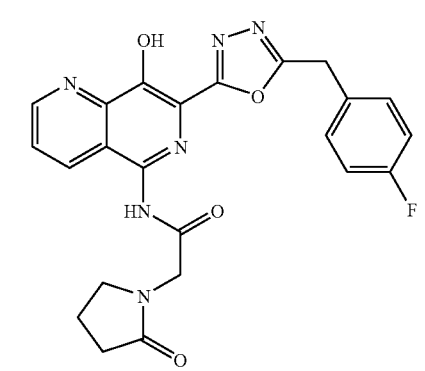 | 462.444 |

-continued

| Example | Name | Structure | Mwt |
|---------|------|-----------|-----|
| 166 | 7-[5-(4-fluorobenzyl)-1,3,4-oxadiazol-2-yl]-8-hydroxy-N-morpholin-4-yl-1,6-naphthyridine-5-carboxamide | 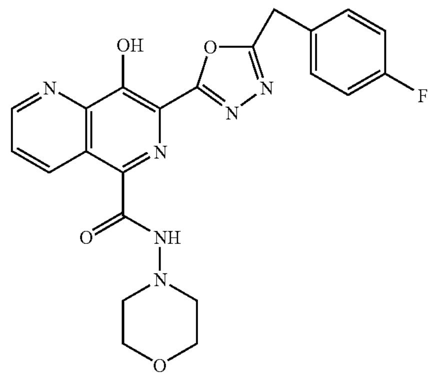 | 450.433 |
| 167 | ethyl 1-{7-[5-(4-fluorobenzyl)-1,3,4-oxadiazol-2-yl]-8-hydroxy-1,6-naphthyridin-5-yl}-2-oxopiperidine-3-carboxylate | 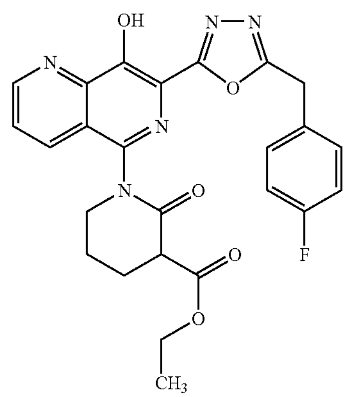 | 491.483 |
| 168 | 7-[5-(4-fluorobenzyl)-1,3,4-oxadiazol-2-yl]-8-hydroxy-N'-(methoxyacetyl)-1,6-naphthyridine-5-carbohydrazide | 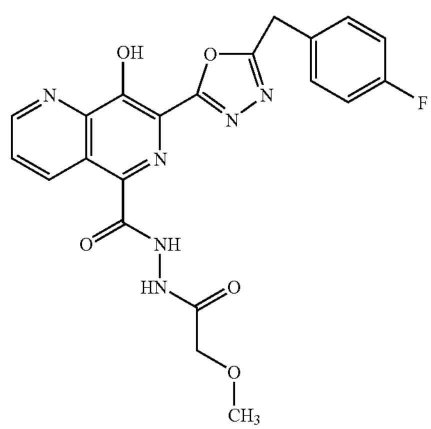 | 452.405 |
| 169 | 7-[5-(4-fluorobenzyl)-1,3,4-oxadiazol-2-yl]-8-hydroxy-N-methoxy-1,6-naphthyridine-5-carboxamide | 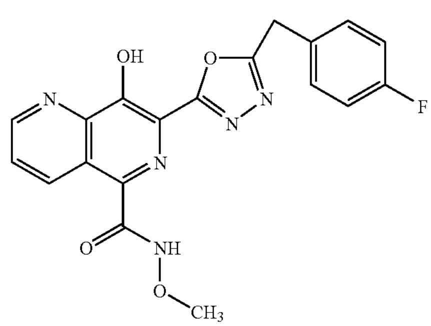 | 395.353 |

-continued

| Example | Name | Structure | Mwt |
|---|---|---|---|
| 170 | 7-[5-(4-fluorobenzyl)-1,3,4-oxadiazol-2-yl]-8-hydroxy-N-(2-methoxyethyl)-1,6-naphthyridine-5-carboxamide | 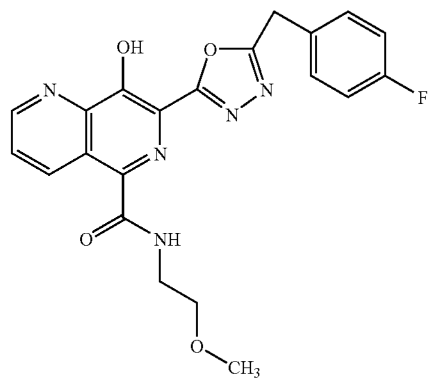 | 423.407 |
| 171 | 1-benzyl-N-{7-[5-(4-fluorobenzyl)-1,3,4-oxadiazol-2-yl]-8-hydroxy-1,6-naphthyridin-5-yl}-5-oxopyrrolidine-3-carboxamide | 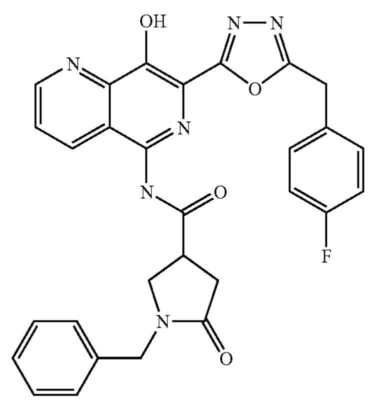 | 538.543 |
| 172 | 7-[5-(4-fluorobenzyl)-1,3,4-oxadiazol-2-yl]-5-[(4-hydroxypiperidin-1-yl)carbonyl]-1,6-naphthyridin-8-ol | 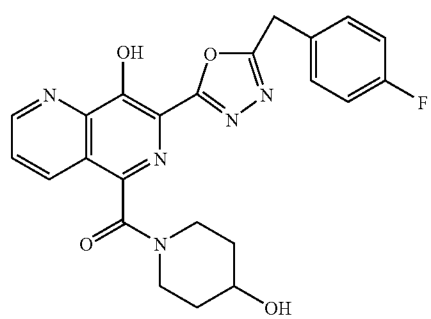 | 449.445 |
| 173 | N~1~-{7-[5-(4-fluorobenzyl)-1,3,4-oxadiazol-2-yl]-8-hydroxy-1,6-naphthyridin-5-yl)-N~1~,N~2~,N~2~-trimethylethanediamide | 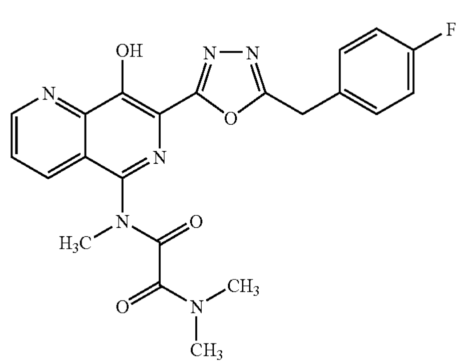 | 450.433 |

-continued

| Example | Name | Structure | Mwt |
|---|---|---|---|
| 174 | 7-[5-(4-fluorobenzyl)-1,3,4-oxadiazol-2-yl]-5-(methylamino)-1,6-naphthyridin-8-ol | 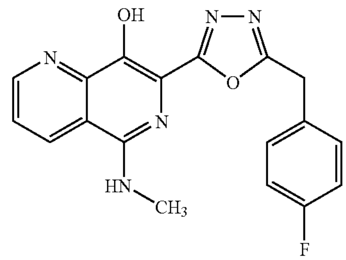 | 351.343 |
| 175 | 5-chloro-7-[5-(4-fluorobenzyl)-1,3-oxazol-2-yl]-1,6-naphthyridin-8-ol | 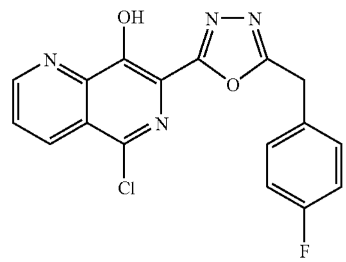 | 355.759 |
| 176 | 1-{7-[5-(4-fluorobenzyl)-1,3-oxazol-2-yl]-8-hydroxy-1,6-naphthyridin-5-yl}-3-methylimidazolidin-2-one | 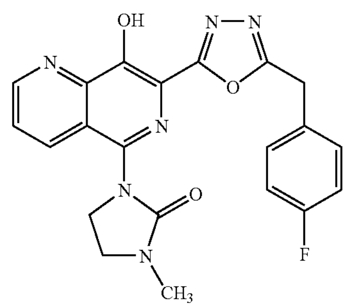 | 419.419 |
| 177 | 7-[5-(4-fluorobenzyl)-1,3,4-oxadiazol-2-yl]-8-hydroxy-N-(3-hydroxypropyl)-1,6-naphthyridine-5-carboxamide | 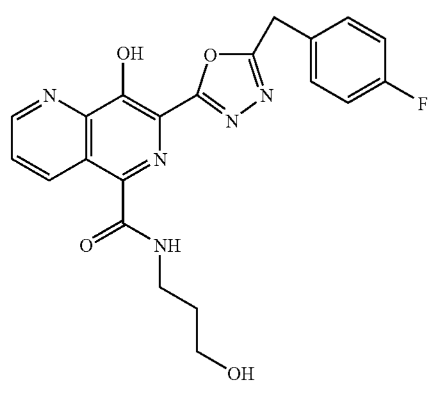 | 423.407 |
| 178 | 4-({7-[5-(4-fluorobenzyl)-1,3,4-oxadiazol-2-yl]-8-hydroxy-1,6-naphthyridin-5-yl}carbonyl)piperazin-2-one | 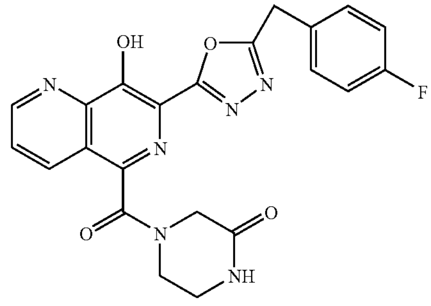 | 448.417 |

| Example | Name | Structure | Mwt |
|---|---|---|---|
| 179 | 7-[5-(4-fluorobenzyl)-1,3,4-oxadiazol-2-yl]-5-[(4-methylpiperazin-1-yl)carbonyl]-1,6-naphthyridin-8-ol | 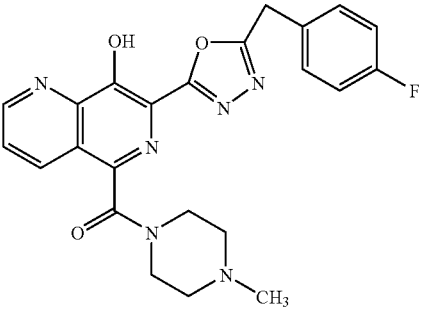 | 448.461 |
| 180 | methyl N-({7-[5-(4-fluorobenzyl)-1,3,4-oxadiazol-2-yl]-8-hydroxy-1,6-naphthyridin-5-yl}carbonyl)glycinate | 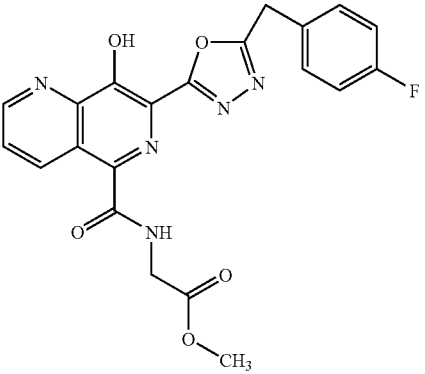 | 437.391 |
| 181 | 7-[5-(4-fluorobenzyl)-1,3,4-oxadiazol-2-yl]-8-hydroxy-N-(1,3-thiazol-2-yl)-1,6-naphthyridine-5-carboxamide | 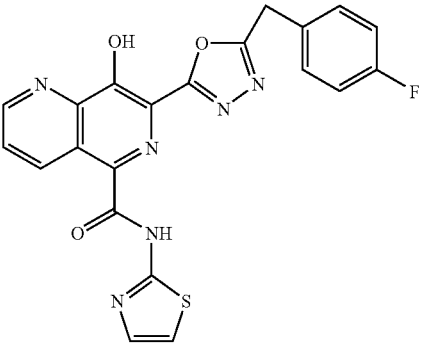 | 448.438 |
| 182 | 7-[5-(4-fluorobenzyl)-1,3,4-oxadiazol-2-yl]-8-hydroxy-N-isopropyl-1,6-naphthyridine-5-carboxamide | 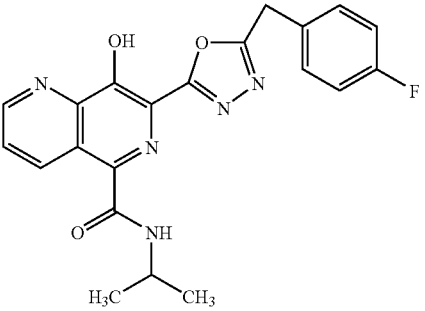 | 407.408 |

-continued

| Example | Name | Structure | Mwt |
|---|---|---|---|
| 183 | N-(4-{7-[5-(4-fluorobenzyl)-1,3-oxazol-2-yl]-8-hydroxy-1,6-naphthyridin-5-yl}phenyl)methanesulfonamide | 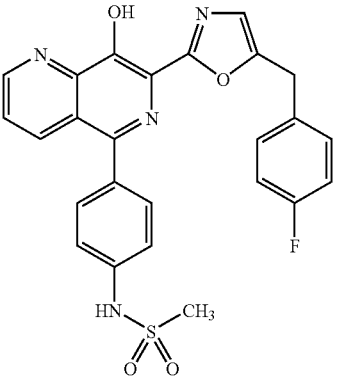 | 490.517 |
| 184 | 7-[5-(4-fluorobenzyl)-1,3,4-oxadiazol-2-yl]-8-hydroxy-N-(2-hydroxyethyl)-1,6-naphthyridine-5-carboxamide | 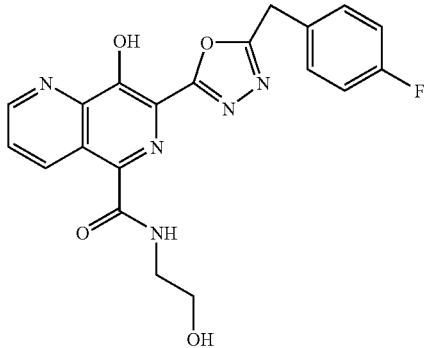 | 409.38 |

EXAMPLE 96

Biological Activity

MT4 Cell Assay

A. Experimental Procedure

Antiviral HIV activity and compound-induced cytotoxicity were measured in parallel by means of a propidium iodide based procedure in the human T-cell lymphotropic virus transformed cell line MT4. Aliquots of the test compounds were serially diluted in medium (RPMI 1640, 10% fetal calf serum (FCS), and gentamycin) in 96-well plates (Costar 3598) using a Cetus Pro/Pette. Exponentially growing MT4 cells were harvested and centrifuged at 1000 rpm for 10 min in a Jouan centrifuge (model CR 4 12). Cell pellets were resuspended in fresh medium (RPMI 1640, 20% FCS, 20% IL-2, and gentamycin) to a density of 5×105 cells/ml. Cell aliquots were infected by the addition of HIV-1 (strain IIIB) diluted to give a viral multiplicity of infection of 100× TCID50. A similar cell aliquot was diluted with medium to provide a mock-infected control. Cell infection was allowed to proceed for 1 hr at 37° C. in a tissue culture incubator with humidified 5% $CO_2$ atmosphere. After the 1 hr incubation the virus/cell suspensions were diluted 6-fold with fresh medium, and 125 µl of the cell suspension was added to each well of the plate containing pre-diluted compound. Plates were then placed in a tissue culture incubator with humidified 5% $CO_2$ for 5 days. At the end of the incubation period, cell number and hence HIV-induced cytopathy was estimated by either (A) propidium iodide staining, or by an (B) MTS tetrazolium staining method (ref. 5).

A. For propidium iodide readout, 27 µl of 5% Nonidet40 was added to each well of the incubation plate. After thorough mixing with a Costar multitip pipetter, 60 µl of the mixture was transferred to filter-bottomed 96-well plates. The plates were analyzed in an automated assay instrument (Screen Machine, Idexx Laboratories). The control and standard used was 3'-azido-3'-deoxythymidine tested over a concentration range of 0.01 to 1 µM in every assay. The expected range of $IC_{50}$ values for 3'-azido-3'-deoxythymidine is 0.04 to 0.12 µM. The assay makes use of a propidium iodide dye to estimate the DNA content of each well.

B. For MTS readout, 20 µl CellTiter 96 AQ One Solution reagent (Promega #G3582) was added to each well. At 75 minutes following the addition of MTS reagent, absobance was read at 492 nM using a Tecan Sunrise 96-well plate reader.

B. Analysis

The antiviral effect of a test compound is reported as an $IC_{50}$, i.e. the inhibitory concentration that would produce a 50% decrease in the HIV-induced cytopathic effect. This effect is measured by the amount of test compound required to restore 50% of the cell growth of HIV-infected MT4 cells, compared to uninfected MT4 cell controls. $IC_{50}$ was calculated by RoboSage, Automated Curve Fitting Program, version 5.00, 10 Jul. 1995.

For each assay plate, the results (relative fluorescence units, rfU, or OD values) of wells containing uninfected cells or infected cells with no compound were averaged, respectively. For measurements of compound-induced cytotoxicty, results from wells containing various compound concentrations and uninfected cells were compared to the average of uninfected cells without compound treatment. Percent of cells remaining is determined by the following formula:

Percent of cells remaining=(compound-treated uninfected cells, rfU, or OD values/untreated uninfected cells)×100.

A level of percent of cells remaining of 79% or less indicates a significant level of direct compound-induced cytotoxicity for the compound at that concentration. When this condition occurs the results from the compound-treated infected wells at this concentration are not included in the calculation of $IC_{50}$.

For measurements of compound antiviral activity, results from wells containing various compound concentrations and infected cells are compared to the average of uninfected and infected cells without compound treatment. Percent inhibition of virus is determined by the following formula:

Percent inhibition of virus=(1−((ave. untreated uninfected cells−treated infected cells)/(ave. untreated uninfected cells−ave. untreated infected cells)))×100

REFERENCES

1. Averett, D. R., Anti-HIV compound assessment by two novel high capacity assays, *J. Virol. Methods* 23: 263-276, 1989.
2. Schwartz, O., et al,. A rapid and simple colorimetric test for the study of anti-HIV agents, *AIDS Res. and Human Retroviruses* 4 (6): 441-447, 1988.
3. Daluge, S. M., et al., 5-chloro-2'3'-deoxy-3'fluorouridine (935U83), a selective anti-human immunodeficiency virus agent with an improved metabolic and toxicological profile. *Antimicro. Agents and Chemother.* 38 (7): 1590-1603, 1994.
4. Dornsife, R. E., et al., Anti-human immunodeficiency virus synergism by zidovudine(3'-azidothymidine) and didanosine(dideoxyinosine) contrasts with the additive inhibition of normal human marrow progenitor cells, *Antimicro. Agents and Chemother.* 35 (2): 322-328, 1991.
1. Promega Technical Bulletin #TB245. CellTiter 96 AQ One Solution Cell Proliferation Assay.

Compounds of the present invention have anti-HIV activity in the range $IC_{50}$=1-1000 nM.

The invention claimed is:
1. A compound of formula (I)

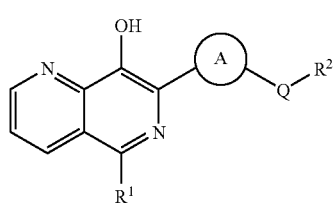

(I)

wherein $R^1$ is selected from 1,2-thiazinan-2-yl optionally substituted with one or more substituents independently selected from group consisting of halogen, hydroxy, $C_{1-8}$alkyl, $C_{1-8}$haloalkyl, —$OR^3$, —$SR^3$, —CN, hydroxy, oxo, —$R^3C(O)N(R^4)_2$, —$C(O)N(R^4)_2$, —$R^3C(O)R^4$, —$R^3OR^3OH$, —$C(O)R^4$, —$N(R^4)C(O)R^4$, —$N(R^4)C(O)R^4$, —$R^3N(R^4)C(O)R^4$, —$N(R^4)_2$, —$R^3N(R^4)_2$, $C_{6-14}$aryl, $C_{6-14}$aryloxy, and $R^3$ optionally substituted with $C_{6-14}$aryl;

$R^2$ is $C_{3-6}$cycloalkyl, or $C_{6-14}$aryl optionally substituted with one or more substituents independently selected from the group consisting of hydrogen, halogen, hydroxy, $C_{1-8}$alkyl, —$OR^5$, and $NR^5R^6$;

$R^3$ is $C_{1-8}$alkyl, $C_{3-6}$cycloalkyl, halo$C_{1-8}$alkyl, $C_{2-6}$alkenyl, $C_{3-6}$cycloalkenyl, or $C_{3-6}$alkenyl;

$R^4$ is hydrogen, $C_{1-8}$alkyl, $C_{3-8}$cycloalkyl, $C_{1-6}$haloalkyl, $C_{6-14}$aryl, $C_{6-14}$aralkyl, $C_{2-6}$alkenyl, or $C_{3-6}$cycloalkenyl, $C_{3-6}$alkynyl;

$R^5$ and $R^6$ are independently selected from the group consisting of hydrogen, $C_{1-8}$haloalkyl, $C_{1-8}$alkyl$C_{3-6}$cycloalkyl, $C_{6-14}$aryl, $C_{6-14}$aralkyl, —$C(O)_mR^7$, —$C(O)C(O)_mR^7$, and Y optionally substituted with one or more —$OR^7$, —$C(O)_mR^7$, —$S(O)_nR^7$, —$S(O)_nR^7$, —$C(O)C(O)_mR^7$, $R^7$ is hydrogen, $C_{1-8}$alkyl, $C_{3-6}$cycloalkyl, —Ycycloalkyl, —YOH, —Y(OY)$_w$ where w is 1-10;

m is 1 or 2;
n is 0, 1, or 2;
p is 0, or 1;
A is 1,3,4-oxadiazolyl;
Q is $C_{1-3}$alkyl, —$NR^4$, —O—, —C(O), —C($OR^4$)—, S(O)$_2$, or —$CF_2$;
Y is a $C_{1-5}$ alkylene chain, wherein said $C_{1-5}$ alkylene chain is optionally subsituted by one or more groups independently selected from =O, =S, and halo, and wherein said $C_{1-5}$ alkylene chain optionally contains 1-3 heteroatoms selected from oxygen, sulfur, and nitrogen;

or pharmaceutically acceptable salt thereof.

2. 5-(1,1-Dioxido-1,2-thiazinan-2-yl)-7[5-(4-fluorobenzyl)-1,3,4-oxadiazol-2-yl]-1,6-naphthyridin-8-ol or pharmaceutically acceptable salt thereof.

3. A pharmaceutical composition comprising an effective amount of a compound according to claim 1 together with a pharmaceutically acceptable carrier.

4. A pharmaceutical composition according to claim 3 in the form of a tablet or capsule.

5. A pharmaceutical composition according to claim 3 in the form of a liquid or suspension.

6. A pharmaceutical composition comprising an effective amount of a compound according to claim 2 together with a pharmaceutically acceptable carrier.

7. A pharmaceutical composition according to claim 6 in the form of a tablet or capsule.

8. A pharmaceutical composition according to claim 6 in the form of a liquid or suspension.

9. A method of treatment of an HIV infection in a human comprising administering to said human an antiviral effective amount of a compound according to claim 2.

10. A method of treatment of an HIV infection in a human comprising administering to said human an antiviral effective amount of a compound according to claim 1.

* * * * *